United States Patent
Iwata et al.

(10) Patent No.: US 11,178,872 B2
(45) Date of Patent: Nov. 23, 2021

(54) CYCLIC AMINE COMPOUND AND PEST CONTROL AGENT

(71) Applicant: Nippon Soda Co., Ltd., Tokyo (JP)

(72) Inventors: Jun Iwata, Odawara (JP); Fumiya Nishio, Odawara (JP); Takao Iwasa, Odawara (JP); Satoshi Makino, Odawara (JP); Koichi Hirata, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 16/098,986

(22) PCT Filed: May 2, 2017

(86) PCT No.: PCT/JP2017/017241
§ 371 (c)(1),
(2) Date: Nov. 5, 2018

(87) PCT Pub. No.: WO2017/195703
PCT Pub. Date: Nov. 16, 2017

(65) Prior Publication Data
US 2019/0191702 A1    Jun. 27, 2019

(30) Foreign Application Priority Data

May 9, 2016 (JP) .............................. JP2016-094063
Nov. 9, 2016 (JP) .............................. JP2016-219103

(51) Int. Cl.
| | | |
|---|---|---|
| C07D 413/14 | (2006.01) |
| A01N 43/90 | (2006.01) |
| A01N 43/42 | (2006.01) |
| C07D 401/06 | (2006.01) |
| C07D 491/107 | (2006.01) |
| A01N 47/02 | (2006.01) |
| A01N 43/54 | (2006.01) |
| A01N 43/40 | (2006.01) |
| A01N 43/52 | (2006.01) |
| A01N 43/56 | (2006.01) |
| A01N 43/82 | (2006.01) |
| C07D 401/14 | (2006.01) |
| C07D 491/056 | (2006.01) |

(52) U.S. Cl.
CPC ............ *A01N 43/90* (2013.01); *A01N 43/40* (2013.01); *A01N 43/42* (2013.01); *A01N 43/52* (2013.01); *A01N 43/54* (2013.01); *A01N 43/56* (2013.01); *A01N 43/82* (2013.01); *A01N 47/02* (2013.01); *C07D 401/06* (2013.01); *C07D 401/14* (2013.01); *C07D 413/14* (2013.01); *C07D 491/056* (2013.01); *C07D 491/107* (2013.01)

(58) Field of Classification Search
CPC .................................................. C07D 413/14

USPC .......................................... 546/194; 514/318
See application file for complete search history.

(56) References Cited

U.S. PATENT DOCUMENTS

| | | |
|---|---|---|
| 2006/0189664 A1 | 8/2006 | Barth et al. |
| 2020/0163336 A1 | 5/2020 | Nishio et al. |

FOREIGN PATENT DOCUMENTS

| | | |
|---|---|---|
| CN | 106467537 A | 3/2017 |
| EP | 2955179 A1 | 12/2015 |
| JP | 2003-206230 A | 7/2003 |
| JP | 2003-531193 A | 10/2003 |
| JP | 2007-514638 A | 6/2007 |
| JP | 2007-515468 A | 6/2007 |
| JP | 2010-090075 A | 4/2010 |
| JP | 2010-535733 A | 11/2010 |

(Continued)

OTHER PUBLICATIONS

International Search Report dated Aug. 1, 2017, in PCT/JP2017/017241.

(Continued)

*Primary Examiner* — Patricia L Morris
(74) *Attorney, Agent, or Firm* — Foley & Lardner LLP

(57) ABSTRACT

A compound represented by a formula (I), or a salt thereof:

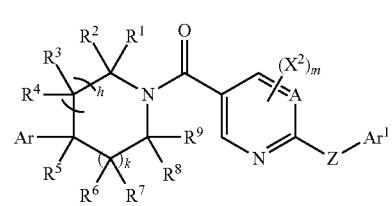

(I)

wherein
$Ar^1$ is a substituted or unsubstituted $C_{6-10}$ aryl group, or the like; the number of $X^1$ groups that can be substituted on $Ar^1$ is 5 or less; $X^1$ is a halogeno group, a substituted or unsubstituted $C_{1-6}$ alkyl group, or the like; Z is a single bond, a sulfur atom, or an oxygen atom; A is a nitrogen atom or a carbon atom; $X^2$ is a halogeno group, a substituted or unsubstituted $C_{1-6}$ alkyl group, or the like; m is an integer of 0 to 2 when A is a nitrogen atom and is an integer of 0 to 3 when A is a carbon atom; $R^1$ to $R^4$ and $R^6$ to $R^9$ each independently represent a hydrogen atom, a substituted or unsubstituted $C_{1-6}$ alkyl group, or the like; $R^5$ is a hydrogen atom, a substituted or unsubstituted $C_{1-6}$ alkyl group, or the like; k represents the number of $CR^6R^7$ moieties in a parenthesis and is 0 or 1; h represents the number of $CR^3R^4$ moieties in a parenthesis and is 0 or 1; and Ar is a substituted or unsubstituted $C_{6-10}$ aryl group, or the like.

8 Claims, No Drawings

(56) References Cited

FOREIGN PATENT DOCUMENTS

| | | |
|---|---|---|
| JP | 2011-524400 A | 9/2011 |
| JP | 2011-527677 A | 11/2011 |
| JP | 2012-512877 A | 6/2012 |
| JP | 2012-520270 A | 9/2012 |
| WO | WO 01/81310 A1 | 11/2001 |
| WO | WO 2005/063754 A1 | 7/2005 |
| WO | WO 2008/126866 A1 | 10/2008 |
| WO | WO 2008/126886 A1 | 10/2008 |
| WO | WO 2009/019163 A1 | 2/2009 |
| WO | WO-2009/153182 A1 | 12/2009 |
| WO | WO 2009/153569 A2 | 12/2009 |
| WO | WO 2010/005783 A1 | 1/2010 |
| WO | WO 2010/080357 A1 | 7/2010 |
| WO | WO 2010/106081 A1 | 9/2010 |
| WO | WO 2011/150457 A2 | 12/2011 |
| WO | WO 2014/123206 A1 | 8/2014 |
| WO | WO 2015/032280 A1 | 3/2015 |
| WO | WO-2016/096942 A1 | 6/2016 |

OTHER PUBLICATIONS

Moss et al., "A new class of 5-HT2B antagonists possesses favorable potency, selectivity, and rat pharmacokinetic properties," Bioorganic & Medicinal Chemistry Letters, 2009, 19(8):2206-2210.

International Search Report dated Nov. 13, 2018, in PCT/JP2018/030637.

U.S. Office Action in U.S. Appl. No. 16/636,223 dated May 18, 2021.

J. G. Cannon, "Analog Design", Chapter Nineteen in Burger's Medicinal Chemistry and Drug Discovery, Fifth Edition, vol. 1: Principles and Practice, Wiley-Interscience, 1995, pp. 783-802.

F. A. Dorwald, "Side Reactions in Organic Synthesis", Wiley: VCH Verlag GmbH & Co. KGaA, Weinheim, 2005, p. IX of Preface p. 1-15.

Sundaresan, et al., "Towards a general model for protein-substrate stereoselectivity" Protein Science (2002), 11: 1330-1339. Published by Cold Spring Harbor Laboratory Press. 2002.

Wikipedia, "Suzuki Reaction", retrieved Oct. 13, 2021 https://en.wikipedia.org/wiki/Suzuki_reaction.

Final Office Action on U.S. Appl. No. 16/636,223 dated Oct. 12, 2021.

CYCLIC AMINE COMPOUND AND PEST CONTROL AGENT

TECHNICAL FIELD

The present invention relates to a cyclic amine compound and a pest control agent. More specifically, the present invention relates to a cyclic amine compound which has excellent insecticidal activity and/or acaricidal activity, is excellent in safety and can be synthesized in an industrially favorable manner, and a pest control agent containing this agent as an active ingredient.

This application is a National Stage application of PCT/JP/2017/017241, filed May 2, 2017, which claims priority to Japanese Patent Application No. 2016-94063, filed May 9, 2016, and Japanese Patent Application No. 2016-219103, filed Nov. 9, 2016, the contents of which are incorporated herein by reference.

BACKGROUND ART

As compounds structurally related to the cyclic amine compounds of the present invention, Patent Document 1 discloses compounds represented by formulas (A), (B) and the like. It has been shown that the compounds are used as insecticides and acaricides.

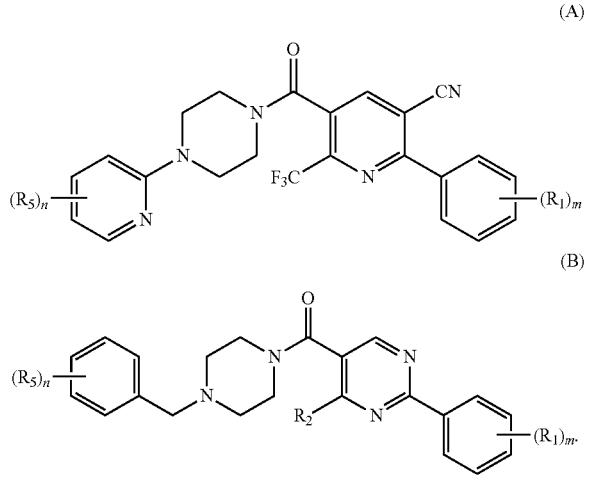

CITATION LIST

Patent Document

[Patent Document 1] PCT International Publication No. WO2015/032280A1

SUMMARY OF INVENTION

Technical Problem

An object of the present invention is to provide a cyclic amine compound which is excellent in pest control activity, in particular, insecticidal activity and/or acaricidal activity, excellent in safety and can be synthesized in an industrially favorable manner, and a pest control agent containing this agent as an active ingredient.

Solution to Problem

As a result of intensive studies in order to solve the above problems, the present invention including the following embodiments has been completed.

[1] A compound represented by a formula (I), or a salt thereof.

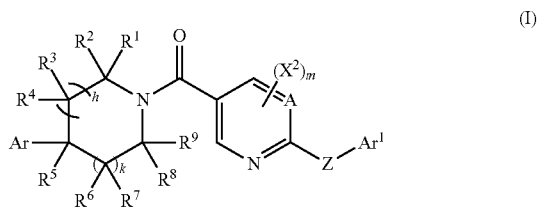

In the formula (I), $Ar^1$ is a substituted or unsubstituted $C_{6-10}$ aryl group or a substituted or unsubstituted 5- to 6-membered heteroaryl group.

Z is a single bond, a sulfur atom, or an oxygen atom.

A is a nitrogen atom or a carbon atom.

$X^2$ represents a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, an imino (substituted or unsubstituted $C_{1-6}$ alkylthio) methyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, a cyano group, or a group represented by the formula: "$R^cO—N=CR^d—$" (wherein $R^c$ is a hydrogen atom, a substituted or unsubstituted $C_{1-6}$ alkyl group, or a substituted or unsubstituted $C_{1-6}$ alkylcarbonyl group, $R^d$ is a hydrogen atom, a substituted or unsubstituted $C_{1-6}$ alkyl group, or an amino group). When there are 2 or more $X^2$ groups, $X^2$ groups may be the same as or different from each other.

m is an integer of 0 to 2 when A is a nitrogen atom and is an integer of 0 to 3 when A is a carbon atom.

$R^1$ to $R^4$ and $R^6$ to $R^9$ each independently represent a hydrogen atom, a substituted or unsubstituted $C_{1-6}$ alkyl group, a substituted or unsubstituted $C_{1-6}$ alkoxy group, a substituted or unsubstituted $C_{1-6}$ alkoxycarbonyl group, a hydroxyl group, or a halogeno group. $R^1$ and $R^9$ may form a $C_{2-6}$ alkylene group together, $R^3$ and $R^6$ may form a $C_{2-6}$ alkylene group together, and $R^2$ and $R^3$ may form a $C_{3-6}$ alkylene group together.

R⁵ represents a hydrogen atom, a substituted or unsubstituted $C_{1-6}$ alkyl group, a substituted or unsubstituted $C_{1-6}$ alkoxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylaminocarbonyl group, a substituted or unsubstituted $C_{1-6}$ alkylcarbonyloxy group, a substituted or unsubstituted $C_{1-6}$ alkoxycarbonyloxy group, a substituted or unsubstituted phenyl group, a hydroxyl group, a halogeno group, or a cyano group. One of the atoms constituting R⁵ and one of the atoms constituting Ar may be bonded to form a ring together with the carbon atom to which R⁵ and Ar are bonded, and R³ and R⁵ may form a $C_{1-6}$ alkylenedioxy group together.

k represents the number of $CR^6R^7$ moieties in a parenthesis and is 0 or 1.

h represents the number of $CR^3R^4$ moieties in a parenthesis and is 0 or 1.

Ar is a dihydrooxazolyl group, a substituted or unsubstituted $C_{6-10}$ aryl group or a substituted or unsubstituted heteroaryl group.

[2] The compound according to the above [1] represented by a formula (II), or a salt thereof.

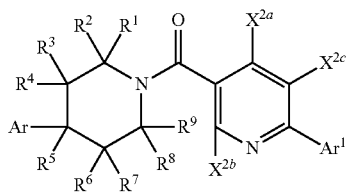

(II)

In formula (II), $Ar^1$, $R^1$ to $R^4$, $R^6$ to $R^9$, $R^5$, and Ar are the same as those defined in the formula (I).

$X^{2a}$ represents a hydrogen atom, or is the same as $X^2$ defined in formula (I).

$X^{2b}$ represents a hydrogen atom, or is the same as $X^2$ defined in formula (I).

$X^{2c}$ is the same as $X^2$ defined in formula (I).

[3] The compound according to [1] or [2], or a salt thereof, wherein a group that can be substituted on a $C_{6-10}$ aryl group or a 5- or 6-membered heteroaryl group represented by $Ar^1$ (a substitutable group is referred to as "$X^1$", the number of the $X^1$ group is 5 or less, and when the number of the $X^1$ group is 2 or more, the $X^1$ groups may be the same as or different from each other, and two $X^1$ groups may form a divalent organic group together) is a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, a cyano group, a pentafluorosulfanyl group, or a group represented by the formula: "$R^aO-N=CR^b-$" (wherein $R^a$ is a hydrogen atom or a substituted or unsubstituted $C_{1-6}$ alkyl group, $R^b$ is a hydrogen atom or a substituted or unsubstituted $C_{1-6}$ alkyl group).

[4] The compound according to the above [1] represented by a formula (III), or a salt thereof.

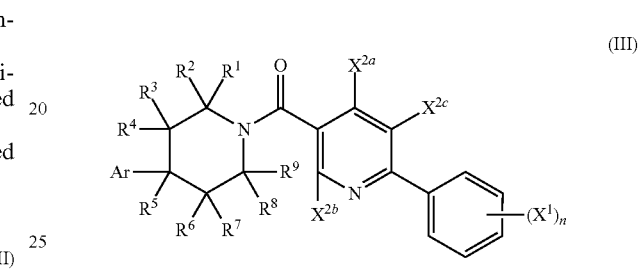

(III)

In formula (III), $R^1$ to $R^4$, $R^6$ to $R^9$, $R^5$ and Ar are the same as those defined in formula (I).

$X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, a cyano group, a pentafluorosulfanyl group, or a group represented by the formula: "$R^aO-N=CR^b-$" (In the formulas, $R^a$ represents a hydrogen atom or a substituted or unsubstituted $C_{1-6}$ alkyl group. $R^b$ represents a hydrogen atom, or a substituted or unsubstituted $C_{1-6}$ alkyl group.)

n represents an integer of 0 to 5. When there are 2 or more $X^1$ groups, $X^1$ groups may be the same as or different from each other. Two $X^1$ groups may form a divalent organic group together.

$X^{2a}$ represents a hydrogen atom, or is the same as $X^2$ defined in formula (I).

$X^{2b}$ represents a hydrogen atom, or is the same as $X^2$ defined in formula (I).

$X^{2c}$ is the same as $X^2$ defined in formula (I).

[5] A pest control agent containing at least one selected from the group consisting of the compounds according to any one of the above [1] to [4] and salts thereof as an active ingredient.

[6] An insecticidal or acaricidal agent containing at least one selected from the group consisting of the compounds according to any one of the above [1] to [4] and salts thereof as an active ingredient.

[7] An ectoparasite controlling agent or eliminator containing at least one selected from the group consisting of the compounds according to any one of the above [1] to [4] and salts thereof as an active ingredient.

[8] A pharmaceutical product for treating a disease or condition to which a sodium channel inhibitor is applied, the pharmaceutical product including at least one selected from the group consisting of the compounds according to any one of the above [1] to [4] and salts thereof as an active ingredient.

Advantageous Effects of Invention

The cyclic amine compound of the present invention can control pests which are problematic in terms of agricultural crops and hygiene. In particular, agricultural pests and mites and ticks can be effectively controlled at lower concentrations. Furthermore, it is possible to effectively control ectoparasites which harm humans and animals.

DESCRIPTION OF EMBODIMENTS

[Compound Represented by Formula (I)]

The cyclic amine compound of the present invention is a compound represented by a formula (I) (hereinafter sometimes referred to as a compound (I)) or a salt of the compound (I).

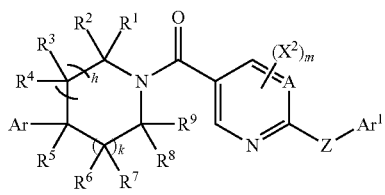

In the present invention, the term "unsubstituted" means that it is composed only of a group which becomes a mother nucleus. When it is described only by the name of the group which becomes the mother nucleus, it means "unsubstituted" unless otherwise stated.

On the other hand, the term "substituted" means that any hydrogen atom of the group which is to become the mother nucleus is substituted with a group having the same or different structure as that of the mother nucleus. Therefore, a "substituent" is another group bonded to a group which becomes a mother nucleus. The number of substituents may be one, or two or more. Two or more substituents may be the same or different.

A "substituent" is chemically acceptable and is not particularly limited as long as it has the effects of the present invention.

Specific examples of groups that may become the "substituent" include the following groups.

Halogeno groups such as a fluoro group, a chloro group, a bromo group, and an iodo group;

$C_{1-6}$ alkyl groups such as a methyl group, an ethyl group, an n-propyl group, an i-propyl group, an n-butyl group, an s-butyl group, an i-butyl group, a t-butyl group, an n-pentyl group, and an n-hexyl group;

$C_{2-6}$ alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group;

$C_{2-6}$ alkynyl groups such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group;

$C_{3-8}$ cycloalkyl groups such as a cyclopropyl group, a cyclobutyl group, a cyclopentyl group, a cyclohexyl group, a cycloheptyl group and a cubanyl group;

$C_{3-8}$ cycloalkenyl groups such as a 2-cyclopropenyl group, a 2-cyclopentenyl group, a 3-cyclohexenyl group and a 4-cyclooctenyl group;

$C_{6-10}$ aryl groups such as a phenyl group and a naphthyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group;

6-membered heteroaryl groups such as a pyridyl group, a pyrazinyl group, a pyrimidinyl group, a pyridazinyl group, and a triazinyl group;

condensed heteroaryl groups such as an indolyl group, a benzofuryl group, a benzothienyl group, a benzimidazolyl group, a benzoxazolyl group, a benzisoxazolyl group, a benzothiazolyl group, a quinolyl group, an isoquinolyl group and quinoxalinyl group;

cyclic ether groups such as an oxiranyl group, a tetrahydrofuryl group, a dioxolanyl group and a dioxanyl group;

cyclic amino groups such as an aziridinyl group, a pyrrolidinyl group, a piperidyl group, a piperazinyl group and a morpholinyl group;

a hydroxyl group; an oxo group;

$C_{1-6}$ alkoxy groups such as a methoxy group, an ethoxy group, an n-propoxy group, an i-propoxy group, an n-butoxy group, an s-butoxy group, an i-butoxy group, and a t-butoxy group;

$C_{2-6}$ alkynyloxy groups such as a vinyloxy group, an allyloxy group, a propenyloxy group, and a butenyloxy group;

$C_{2-6}$ alkynyloxy groups such as an ethynyloxy group and a propargyloxy group;

$C_{6-10}$ aryloxy groups such as a phenoxy group and a naphthoxy group;

5- to 6-membered heteroaryloxy groups such as a thiazolyloxy group and a pyridyloxy group;

hydroxy $C_{1-6}$ alkyl groups such as a hydroxymethyl group and a hydroxyethyl group;

$C_{1-6}$ alkoxyalkyl groups such as a methoxymethyl group and an ethoxymethyl group;

$C_{1-6}$ alkoxy $C_{1-6}$ alkoxy groups such as a methoxymethoxy group and an ethoxymethoxy group;

a carboxyl group;

a formyl group; $C_{1-6}$ alkylcarbonyl groups such as an acetyl group and a propionyl group;

a formyloxy group; $C_{1-6}$ alkylcarbonyloxy groups such as an acetyloxy group, a propionyloxy group, an n-propylcarbonyloxy group and an i-propylcarbonyloxy group;

$C_{1-6}$ alkoxycarbonyl groups such as a methoxycarbonyl group, an ethoxycarbonyl group, an n-propoxycarbonyl group, an i-propoxycarbonyl group, an n-butoxycarbonyl group and a t-butoxycarbonyl group;

$C_{1-6}$ haloalkyl groups such as a chloromethyl group, a chloroethyl group, a difluoromethyl group, a trifluoromethyl group, a 2,2,2-trifluoroethyl group, a perfluoroethyl group, a 1,2-dichloro-n-propyl group, a perfluoropropan-2-yl group, a 1-fluoro-n-butyl group and a perfluoro-n-pentyl group;

$C_{1-6}$ alkoxy $C_{1-6}$ haloalkyl groups such as a 1,1,1,3,3,3-hexafluoro-2-methoxypropan-2-yl group and the like;

$C_{2-6}$ haloalkenyl groups such as a 2-chloro-1-propenyl group and a 2-fluoro-1-butenyl group;

$C_{2-6}$ haloalkynyl groups such as a 4,4-dichloro-1-butynyl group, a 4-fluoro-1-pentynyl group, and a 5-bromo-2-pentynyl group;

$C_{3-6}$ halocycloalkyl groups such as a 3,3-difluorocyclobutyl group;

$C_{1-6}$ haloalkoxy groups such as a 2-chloro-n-propoxy group, a 2,3-dichlorobutoxy group, a difluoromethoxy group, a trifluoromethoxy group, a 2,2,2-trifluoroethoxy group, a 1,1,2,2-tetrafluoroethoxy group, a 2,2,3,3,3-pentafluoropropoxy group, a 4,4,4-trifluorobutoxy group and a (1,1,1,3,3,3-hexafluoropropan-2-yl)oxy group;

$C_{2-6}$ haloalkenyloxy groups such as a 2-chloropropenyloxy group and a 3-bromobutenyloxy group;

$C_{1-6}$ haloalkylcarbonyl groups such as a chloroacetyl group, a trifluoroacetyl group and a trichloroacetyl group;

a cyano group; a nitro group; an amino group;

$C_{1-6}$ alkylamino groups such as a methylamino group, a dimethylamino group and a diethylamino group;

$C_{6-10}$ acylamino groups such as an anilino group and a naphthylamino group;

a formylamino group; $C_{1-6}$ alkylcarbonylamino groups such as an acetylamino group, a propanoylamino group, a butyrylamino group and an i-propylcarbonylamino group;

$C_{1-6}$ alkoxycarbonylamino groups such as a methoxycarbonylamino group, an ethoxycarbonylamino group, an n-propoxycarbonylamino group and an i-prop oxycarbonylamino group;

$C_{1-6}$ alkylsulfoxyimino groups such as an S,S-dimethylsulfoxyimino group and the like;

a carbamoyl group; an N'-hydroxycarbamimidoyl group;

$C_{1-6}$ alkylaminocarbonyl groups such as a methylaminocarbonyl group, a dimethylaminocarbonyl group, an ethylaminocarbonyl group and an i-propylaminocarbonyl group;

imino $C_{1-6}$ alkyl groups such as an iminomethyl group, a (1-imino) ethyl group and a (1-imino)-n-propyl group;

hydroxyimino $C_{1-6}$ alkyl groups such as a hydroxyiminomethyl group, a (1-hydroxyimino) ethyl group and a (1-hydroxyimino) propyl group;

$C_{1-6}$ alkoxyimino (which may be substituted with a halogeno group) $C_{1-6}$ alkyl groups such as a methoxyiminomethyl group and a (1-methoxyimino)ethyl group;

$C_{1-6}$ alkylcarbonyloxyimino $C_{1-6}$ alkyl groups such as an acetoxyiminomethyl group;

a mercapto group;

$C_{1-6}$ alkylthio groups such as a methylthio group, an ethylthio group, an n-propylthio group, an i-propylthio group, an n-butylthio group, an i-butylthio group, an s-butylthio group and a t-butylthio group;

$C_{1-6}$ haloalkylthio groups such as a trifluoromethylthio group and a 2,2,2-trifluoroethylthio group;

$C_{2-6}$ alkenylthio groups such as a vinylthio group and an allylthio group;

$C_{2-6}$ alkynylthio groups such as an ethynylthio group and a propargylthio group;

$C_{1-6}$ alkylsulfinyl groups such as a methylsulfinyl group, an ethylsulfinyl group and a t-butylsulfinyl group;

$C_{1-6}$ haloalkylsulfinyl groups such as a trifluoromethylsulfinyl group and a 2,2,2-trifluoroethylsulfinyl group;

$C_{2-6}$ alkenylsulfinyl groups such as an allylsulfinyl group;

$C_{2-6}$ alkynylsulfinyl groups such as a propargylsulfinyl group;

$C_{1-6}$ alkylsulfonyl groups such as a methylsulfonyl group, an ethylsulfonyl group and a t-butylsulfonyl group;

$C_{1-6}$ haloalkylsulfonyl groups such as a trifluoromethylsulfonyl group and a 2,2,2-trifluoroethylsulfonyl group;

$C_{2-6}$ alkenylsulfonyl groups such as an allylsulfonyl group;

$C_{2-6}$ alkynylsulfonyl groups such as a propargylsulfonyl group;

a thiocarbamoyl group;

imino ($C_{1-6}$ alkylthio) methyl groups such as an imino (methylthio) methyl group;

a pentafluorosulfanyl group;

tri $C_{1-6}$ alkylsilyl groups such as a trimethylsilyl group, a triethylsilyl group and a t-butyldimethylsilyl group; and tri $C_{6-10}$ arylsilyl groups such as a triphenylsilyl group.

Further, in these "substituents", any hydrogen atom in the substituent may be substituted with a group having a different structure.

The terms "$C_{1-6}$" and the like mean that the number of carbon atoms in the group serving as a mother nucleus is 1 to 6, and so on. The number of carbon atoms does not include the number of carbon atoms present in the substituent. For example, an ethoxybutyl group is classified as a $C_2$ alkoxy $C_4$ alkyl group because the group serving as a mother nucleus is a butyl group and the substituent is an ethoxy group.

In the formula (I), $Ar^1$ is a substituted or unsubstituted $C_{6-10}$ aryl group or a substituted or unsubstituted 5 to 6 membered heteroaryl group.

The $C_{6-10}$ aryl group is a group formed by eliminating one hydrogen on the ring of a monocyclic or polycyclic aromatic hydrocarbon. As the $C_{6-10}$ aryl group, a phenyl group, a naphthyl group and the like can be mentioned.

Examples of the 5- to 6-membered heteroaryl groups include 5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group; and 6-membered heteroaryl groups such as a pyridyl group, a pyrazinyl group, a pyrimidinyl group, a pyridazinyl group, and a triazinyl group.

$Ar^1$ is preferably a phenyl group, a naphthyl group, a thienyl group, a pyrazolyl group, a pyridyl group, or a pyrimidinyl group.

In the formula (I), Z represents a single bond, a sulfur atom or an oxygen atom.

Z is preferably a single bond.

In the formula (I), A is a nitrogen atom or a carbon atom.

A is preferably a carbon atom.

In the formula (I), $X^2$ represents a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, an imino (substituted or unsubstituted $C_{1-6}$ alkylthio) methyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, a cyano group, or a group represented by the formula: "$R^cO-N=CR^d-$" (wherein $R^c$ represents a hydrogen atom, a substituted or unsubstituted $C_{1-6}$ alkyl group, or a substituted or unsubstituted $C_{1-6}$ alkylcarbonyl group, $R^d$ represents a hydrogen atom, a substituted or unsubstituted $C_{1-6}$ alkyl group, or an amino group). When there are 2 or more $X^2$ groups, $X^2$ groups may be the same as or different from each other.

As the "halogeno group" represented by $X^2$, a fluoro group, a chloro group, a bromo group, an iodo group and the like can be mentioned.

The "$C_{1-6}$ alkyl group" represented by $X^2$ may be linear or branched. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Examples of the "$C_{2-6}$ alkenyl group" represented by $X^2$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "$C_{2-6}$ alkenyloxy group" represented by $X^2$ include a vinyloxy group, an allyloxy group, a propenyloxy group and a butenyloxy group.

Examples of the "$C_{2-6}$ alkynyl group" represented by $X^2$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group.

Examples of the "$C_{1-6}$ alkoxy group" represented by $X^2$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group and an i-hexyloxy group.

Examples of the "$C_{1-6}$ alkylamino group" represented by $X^2$ include a methylamino group, a dimethylamino group and a diethylamino group.

Examples of the "$C_{1-6}$ alkylcarbonyl group" represented by $X^2$ include an acetyl group, a propionyl group and the like.

Examples of the "$C_{1-6}$ alkylcarbonylamino group" represented by $X^2$ include an acetylamino group, a propionylamino group and the like.

Examples of the "$C_{1-6}$ alkoxycarbonyl group" represented by $X^2$ include a methoxycarbonyl group, an ethoxycarbonyl group, an n-propoxycarbonyl group, an i-propoxycarbonyl group and a t-butoxycarbonyl group.

Examples of the "$C_{1-6}$ alkylaminocarbonyl group" represented by $X^2$ include a methylaminocarbonyl group, a dimethylaminocarbonyl group, an ethylaminocarbonyl group, a diethylaminocarbonyl group and an i-propylaminocarbonyl group.

Examples of the "$C_{1-6}$ alkylaminocarbonyloxy group" represented by $X^2$ include a methylaminocarbonyloxy group, a dimethylaminocarbonyloxy group, an ethylaminocarbonyloxy group, a diethylaminocarbonyloxy group and an i-propylaminocarbonyloxy group.

Examples of the "$C_{1-6}$ alkylcarbonyloxy group" represented by $X^2$ include an acetyloxy group, a propionyloxy group, an n-butyryloxy group and an i-butyryloxy group.

Examples of the "$C_{1-6}$ alkylthio group" represented by $X^2$ include a methylthio group, an ethylthio group, an n-propylthio group, an n-butylthio group, an n-pentylthio group, an n-hexylthio group and an i-propylthio group.

Examples of the "$C_{1-6}$ alkylsulfinyl group" represented by $X^2$ include a methylsulfinyl group, an ethylsulfinyl group and a t-butylsulfinyl group.

Examples of the "$C_{1-6}$ alkylsulfonyl group" represented by $X^2$ include a methylsulfonyl group, an ethylsulfonyl group and a t-butylsulfonyl group.

Examples of the "$C_{1-6}$ alkoxysulfonyl group" represented by $X^2$ include a methoxysulfonyl group, an ethoxysulfonyl group and a t-butoxysulfonyl group.

Examples of the "$C_{1-6}$ alkylaminothiocarbonyl group" represented by $X^2$ include a methylaminothiocarbonyl group, a dimethylaminothiocarbonyl group, an ethylaminothiocarbonyl group, a methylaminothiocarbonyl group and an i-propylaminothiocarbonyl group.

Examples of the "imino ($C_{1-6}$ alkylthio) methyl group" represented by $X^2$ include an imino (methylthio) methyl group, an imino (ethylthio) methyl group and the like.

Examples of the "$C_{1-6}$ alkylaminosulfonyl group" represented by $X^2$ include a methylaminosulfonyl group, a dimethylaminosulfonyl group, an ethylaminosulfonyl group, a diethylaminosulfonyl group and an i-propylaminosulfonyl group.

Preferred examples of the substituents on the "$C_{1-6}$ alkyl group", "$C_{2-6}$ alkenyl group", "$C_{2-6}$ alkenyloxy group", "$C_{2-6}$ alkynyl group", "$C_{1-6}$ alkoxy group", "$C_{1-6}$ alkylamino group, "$C_{1-6}$ alkylcarbonyl group", "$C_{1-6}$ alkylcarbonylamino group", "$C_{1-6}$ alkoxycarbonyl group", "$C_{1-6}$ alkylaminocarbonyl group", "$C_{1-6}$ alkylaminocarbonyloxy group", "$C_{1-6}$ alkylcarbonyloxy group", "$C_{1-6}$ alkylthio group", "$C_{1-6}$ alkylsulfinyl group", "$C_{1-6}$ alkylsulfonyl group", "$C_{1-6}$ alkoxysulfonyl group", "$C_{1-6}$ alkylaminothiocarbonyl group", "imino ($C_{1-6}$ alkylthio) methyl group" or "$C_{1-6}$ alkylaminosulfonyl group" represented by $X^2$ include a halogeno group such as a fluoro group, a chloro group, a bromo group or an iodo group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; and a cyano group.

Examples of the "$C_{3-8}$ cycloalkyl group" represented by $X^2$ include a cyclopropyl group, a cyclobutyl group, a cyclopentyl group, a cyclohexyl group and a cycloheptyl group.

Examples of the "$C_{6-10}$ aryl group" represented by $X^2$ include a phenyl group, a naphthyl group and the like.

Examples of the "heteroaryl group" represented by $X^2$ include 5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group; 6-membered heteroaryl groups such as a pyridyl group, a pyrazinyl group, a pyrimidinyl group, a pyridazinyl group and a triazinyl group; and condensed heteroaryl groups such as an indolyl group, a benzofuryl group, a benzo[1,3] dioxolyl group, a benzothienyl group, a benzoimidazolyl group, a benzoxazolyl group, a benzothiazolyl group, a quinolyl group, an isoquinolyl group and a quinoxalinyl group.

Examples of the "$C_{6-10}$ aryloxy group" represented by $X^2$ include a phenoxy group, a naphthoxy group and the like.

Examples of the "heteroaryloxy group" represented by $X^2$ include 5- to 6-membered heteroaryloxy groups such as a thiazolyloxy group, a pyridyloxy group and the like.

Preferred examples of the substituents on the "$C_{3-8}$ cycloalkyl group", "$C_{6-10}$ aryl group", "heteroaryl group", "$C_{6-10}$ aryloxy group", and "heteroaryloxy group" represented by $X^2$ include a halogeno group such as a fluoro group, a chloro group, a bromo group and an iodo group; $C_{1-6}$ alkyl groups such as a methyl group, an ethyl group, an n-propyl group, an i-propyl group, an n-butyl group, an s-butyl group, an i-butyl group, an t-butyl group, an n-pentyl group and an n-hexyl group; $C_{1-6}$ haloalkyl groups such as a chloromethyl group, a chloroethyl group, a trifluoromethyl group, a 1,2-dichloro-n-propyl group, a 1-fluoro-n-butyl group and a perfluoro-n-pentyl group; $C_{1-6}$ alkoxy groups such as a methoxy group, an ethoxy group, an n-propoxy group, an i-propoxy group, an n-butoxy group, an s-butoxy group, an i-butoxy group and a t-butoxy group; $C_{1-6}$ haloalkoxy groups such as a 2-chloro-n-propoxy group, a 2,3-dichlorobutoxy group and a trifluoromethoxy group; and a cyano group.

One of the substituents $X^2$ is a "group represented by the formula: "$R^cO-N=CR^d-$"".

In the formula, $R^c$ is a hydrogen atom, a substituted or unsubstituted $C_{1-6}$ alkyl group, or a substituted or unsubstituted $C_{1-6}$ alkylcarbonyl group. $R^b$ is a hydrogen atom, a substituted or unsubstituted $C_{1-6}$ alkyl group, or an amino group.

The "$C_{1-6}$ alkyl group" represented by $R^c$ and $R^d$ in the formula may be linear or branched. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Examples of the "$C_{1-6}$ alkylcarbonyl group" represented by $R^c$ in the formula include an acetyl group, a propionyl group and the like.

Preferred examples of the substituents on the "$C_{1-6}$ alkyl group" and "$C_{1-6}$ alkylcarbonyl group" include a halogeno group such as a fluoro group, a chloro group, a bromo group and an iodo group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; and a cyano group.

$X^2$ is preferably a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, a formyl group, a substituted or unsubstituted $C_{1-6}$ alkylcarbonyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a thiocarbonyl group, an imino (substituted or unsubstituted $C_{1-6}$ alkylthio) methyl group, a substituted or unsubstituted $C_{3-8}$ cycloalkyl group, a substituted or unsubstituted $C_{6-10}$ aryl group, a substituted or unsubstituted heteroaryl group, a cyano group, or a group represented by the formula: "$R^cO-N=CR^d-$" (in the formula, $R^c$ represents a hydrogen atom, a substituted or unsubstituted $C_{1-6}$ alkyl group, or a substituted or unsubstituted $C_{1-6}$ alkylcarbonyl group, and $R^d$ represents a hydrogen atom, a substituted or unsubstituted $C_{1-6}$ alkyl group, or an amino group).

As the "substituted or unsubstituted $C_{1-6}$ alkyl group", a halogeno-substituted, $C_{1-6}$ alkoxy-substituted or unsubstituted $C_{1-6}$ alkyl group is preferable.

As the "substituted or unsubstituted $C_{1-6}$ alkoxy group", a halogeno-substituted or unsubstituted $C_{1-6}$ alkoxy group is preferable.

As the "substituted or unsubstituted $C_{1-6}$ alkylthio group", a halogeno-substituted or unsubstituted $C_{1-6}$ alkylthio group is preferable.

As the "substituted or unsubstituted $C_{1-6}$ alkylsulfinyl group", a halogeno-substituted or unsubstituted $C_{1-6}$ alkylsulfinyl group is preferable.

As the "substituted or unsubstituted $C_{1-6}$ alkylsulfonyl group", a halogeno-substituted or unsubstituted $C_{1-6}$ alkylsulfonyl group is preferable.

As the "imino (substituted or unsubstituted $C_{1-6}$ alkylthio) methyl group", an imino (halogeno-substituted or unsubstituted $C_{1-6}$ alkylthio) methyl group is preferable.

As the "group represented by the formula: "$R^cO-N=CR^d-$", a group in which $R^c$ is a halogeno-substituted or unsubstituted $C_{1-6}$ alkyl group and $R^d$ is a hydrogen atom is preferable.

In the formula (I), m represents the number of substitutions of $X^2$, and it is an integer of 0 to 2 when A is a nitrogen atom, and it is an integer of 0 to 3 when A is a carbon atom. When m is 2 or more, $X^2$ groups may be the same as or different from each other.

In the formula (I), $R^1$ to $R^4$ and $R^6$ to $R^9$ each independently represent a hydrogen atom, a substituted or unsubstituted $C_{1-6}$ alkyl group, a substituted or unsubstituted $C_{1-6}$ alkoxy group, a substituted or unsubstituted $C_{1-6}$ alkoxycarbonyl group, a hydroxyl group, or a halogeno group.

$R^1$ and $R^9$ may form a $C_{2-6}$ alkylene group together, $R^3$ and $R^6$ may form a $C_{2-6}$ alkylene group together, and $R^2$ and $R^3$ may form a $C_{3-6}$ alkylene group together.

As the "substituted or unsubstituted $C_{1-6}$ alkyl group", "substituted or unsubstituted $C_{1-6}$ alkoxy group", "substituted or unsubstituted $C_{1-6}$ alkoxycarbonyl group" and "halogeno group" represented by $R^1$ to $R^4$ and $R^6$ to $R^9$, the same as those specifically exemplified for $X^2$ can be mentioned.

As the "$C_{2-6}$ alkylene group", an ethylene group, a trimethylene group, a tetramethylene group, a pentamethylene group and the like can be exemplified.

As the "$C_{3-6}$ alkylene group", a trimethylene group, a tetramethylene group, a pentamethylene group and the like can be exemplified.

In the formula (I), $R^5$ represents a hydrogen atom, a substituted or unsubstituted $C_{1-6}$ alkyl group, a substituted or unsubstituted $C_{1-6}$ alkoxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylaminocarbonyl group, a substituted or unsubstituted $C_{1-6}$ alkylcarbonyloxy group, a substituted or unsubstituted $C_{1-6}$ alkoxycarbonyloxy group, a substituted or unsubstituted phenyl group, a hydroxyl group, a halogeno group, or a cyano group. One of the atoms constituting R5 and one of the atoms constituting Ar may be bonded to form a ring together with the carbon atom to which $R^5$ and Ar are bonded. Further, $R^3$ and $R^5$ may form a $C_{1-6}$ alkylenedioxy group together.

As the "substituted or unsubstituted $C_{1-6}$ alkyl group", "substituted or unsubstituted $C_{1-6}$ alkoxy group", "substituted or unsubstituted $C_{1-6}$ alkylcarbonyl group", "substituted or unsubstituted $C_{1-6}$ alkoxycarbonyl group", "substituted or unsubstituted $C_{1-6}$ alkylaminocarbonyl group", "substituted or unsubstituted $C_{1-6}$ alkylcarbonyloxy group" and "halogeno group" represented by $R^5$, the same as those specifically exemplified for $X^2$ can be mentioned.

Examples of the "$C_{1-6}$ alkoxycarbonyloxy group" represented by $R^5$ include a methoxycarbonyloxy group, an ethoxycarbonyloxy group, an n-propoxycarbonyloxy group, an i-propoxycarbonyloxy group, an n-butoxycarbonyloxy group and a t-butoxycarbonyloxy group.

Preferable examples of the substituent on the "$C_{1-6}$ alkoxycarbonyloxy group" represented by $R^5$ include a halogeno group, a $C_{1-6}$ alkoxy group, a $C_{1-6}$ haloalkoxy group and a cyano group.

Examples of the "$C_{1-6}$ alkylenedioxy group" formed by $R^3$ and $R^5$ together include a methylenedioxy group, an ethylenedioxy group and the like.

In the formula (I), k represents the number of $CR^6R^7$ moieties in a parenthesis and is 0 or 1.

In the formula (I), h represents the number of $CR^3R^4$ moieties in a parenthesis and is 0 or 1.

In the formula (I), Ar is a dihydrooxazolyl group, a substituted or unsubstituted $C_{6-10}$ aryl group or a substituted or unsubstituted heteroaryl group.

Examples of the "$C_{6-10}$ aryl group" include a phenyl group, a naphthyl group and the like.

Examples of the "heteroaryl group" include 5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group; and 6-membered heteroaryl groups such as a pyridyl group, a pyrazinyl group, a pyrimidinyl group, a pyridazinyl group, and a triazinyl group.

Further, as the "heteroaryl group", 9-membered heteroaryl groups such as an indolyl group, an isoindolyl group, a benzofuranyl group, a benzothienyl group, an indazolyl group, a benzimidazolyl group, a benzoxazolyl group, a benzoisoxazolyl group, a benzothiazolyl group and a benzoisothiazolyl group; and 10-membered heteroaryl groups such as a quinolinyl group, an isoquinolinyl group, a cinnolinyl group, a phthalazinyl group, a quinazolinyl group and a quinoxanyl group; and the like can be mentioned.

As the substituent on the "$C_{6-10}$ aryl group" and the "heteroaryl group" represented by Ar, a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a substituted or unsubstituted $C_{1-6}$ alkylcarbonylamino group, a formyl group, a substituted or unsubstituted $C_{1-6}$ alkylcarbonyl group, a carboxyl group, a substituted or unsubstituted $C_{1-6}$ alkoxycarbonyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a substituted or unsubstituted $C_{1-6}$ alkylaminothiocarbonyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, or a cyano group can be mentioned.

Specific examples of these substituents include the same as those exemplified for $X^2$.

The number of substituents is 5 or less, and when there are two or more substituents, the respective substituents may be the same or different from each other. Further, two substituents may form a divalent organic group together. Examples of the divalent organic group formed by the two substituents together include $C_{3-6}$ alkylene groups such as a trimethylene group, a tetramethylene group and a pentamethylene group; $C_{1-6}$ alkylenedioxy groups such as a methylenedioxy group and an ethylenedioxy group; $C_{1-6}$ haloalkylenedioxy groups such as a difluoromethylenedioxy group and a tetrafluoroethylenedioxy group; and the like.

As the substituent on the "$C_{6-10}$ aryl group" and the "heteroaryl group" represented by Ar, a halogeno group, a substituted or unsubstituted $C_{1-6}$ alkyl group, a hydroxyl group, a substituted or unsubstituted $C_{1-6}$ alkoxy group, a substituted or unsubstituted $C_{1-6}$ alkoxycarbonyl group, a substituted or unsubstituted $C_{3-8}$ cycloalkyl group, a substituted or unsubstituted $C_{6-10}$ aryl group, a cyano group or an oxy $C_{1-6}$ haloalkyleneoxy group is preferable.

As the "substituted or unsubstituted $C_{1-6}$ alkyl group", a halogeno-substituted, $C_{1-6}$ alkoxy-substituted or unsubstituted $C_{1-6}$ alkyl group is preferable.

As the "substituted or unsubstituted $C_{1-6}$ alkoxy group", a halogeno-substituted or unsubstituted $C_{1-6}$ alkoxy group is preferable.

The salt of compound (I) is not particularly limited as long as it is agriculturally and horticulturally acceptable salt. Examples thereof include salts of inorganic acids such as hydrochloric acid and sulfuric acid; salts of organic acids such as acetic acid and lactic acid; salts of alkali metals such as lithium, sodium and potassium; salts of alkaline earth metals such as calcium and magnesium; salts of transition metals such as iron and copper; salts of organic bases such as ammonia, triethylamine, tributylamine, pyridine and hydrazine, and the like.

The compound (I) or the salt of the compound (I) is not particularly limited by the production method thereof. Further, the salt of the compound (I) can be obtained from the compound (I) by a known method. For example, the compound (I) or the salt of the compound (I) of the present invention can be obtained by a known production method described in Examples and the like.

[Compound Represented by Formula (II)]

The cyclic compound of the present invention is preferably a compound represented by a formula (II).

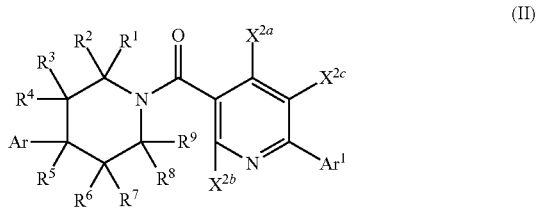

(II)

In the formula (II), $Ar^1$, $R^1$ to $R^4$, $R^6$ to $R^9$, $R^5$, and Ar are the same as those defined in the formula (I). $X^{2a}$ represents a hydrogen atom, or is the same as $X^2$ defined in the formula (I). $X^{2b}$ represents a hydrogen atom, or is the same as $X^2$ defined in the formula (I). $X^{2c}$ is the same as $X^2$ defined in the formula (I).

$X^{2b}$ is preferably $X^2$.

[$X^1$]

A group that can be substituted on a $C_{6-10}$ aryl group or a 5- or 6-membered heteroaryl group represented by $Ar^1$ is referred to as $X^1$. The number of the $X^1$ group is 5 or less, and when there are 2 or more $X^1$ groups, $X^1$ groups may be the same as or different from each other. Further, two $X^1$ groups may form a divalent organic group together.

$X^1$ represents a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted heteroaryl group, a substituted or unsubstituted $C_{6-10}$ aryloxy group, a substituted or unsubstituted heteroaryloxy group, a nitro group, a cyano group, a pentafluorosulfanyl group, or a group represented by the formula: "$R^aO—N=CR^b—$" (in the formula, $R^a$ represents a hydrogen atom or a substituted or unsubstituted $C_{1-6}$ alkyl group. $R^b$ represents a hydrogen atom, or a substituted or unsubstituted $C_{1-6}$ alkyl group.)

As the "halogeno group", "substituted or unsubstituted $C_{1-6}$ alkyl group", "substituted or unsubstituted $C_{2-6}$ alkenyl group", "substituted or unsubstituted $C_{2-6}$ alkenyloxy group", "substituted or unsubstituted $C_{2-6}$ alkynyl group", "substituted or unsubstituted $C_{1-6}$ alkoxy group", "substituted or unsubstituted $C_{1-6}$ alkylamino group", "substituted or unsubstituted $C_{1-6}$ alkylcarbonyl group", "substituted or unsubstituted $C_{1-6}$ alkylcarbonylamino group", "substituted or unsubstituted $C_{1-6}$ alkoxycarbonyl group", "substituted or unsubstituted $C_{1-6}$ alkylaminocarbonyl group", "substituted or unsubstituted $C_{1-6}$ alkylaminocarbonyloxy group", "substituted or unsubstituted $C_{1-6}$ alkylcarbonyloxy group", "substituted or unsubstituted $C_{1-6}$ alkylthio group", "substituted or unsubstituted $C_{1-6}$ alkylsulfinyl group", "substituted or unsubstituted $C_{1-6}$ alkylsulfonyl group", "substituted or unsubstituted $C_{1-6}$ alkoxysulfonyl group", "substituted or unsubstituted $C_{1-6}$ alkylaminothiocarbonyl group", "substituted or unsubstituted $C_{1-6}$ alkylaminosulfonyl group", "substituted or unsubstituted $C_{3-8}$ cycloalkyl group", "substituted or unsubstituted $C_{6-10}$ aryl group", "substituted or unsubstituted heteroaryl group", "substituted or unsubstituted $C_{6-10}$ aryloxy group", and "substituted or unsubstituted heteroaryloxy group" represented by $X^1$, the same as those specifically exemplified for $X^2$ can be mentioned.

One of the substituents $X^1$ is a "group represented by the formula: "$R^aO—N=CR^b—$"".

In the formula, $R^a$ is a hydrogen atom, or a substituted or unsubstituted $C_{1-6}$ alkyl group. $R^b$ is a hydrogen atom, or a substituted or unsubstituted $C_{1-6}$ alkyl group.

The "$C_{1-6}$ alkyl group" represented by $R^a$ and $R^b$ in the formula may be linear or branched. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group. Preferred examples of the substituents on the "$C_{1-6}$ alkyl group" include a halogeno group such as a fluoro group, a chloro group, a bromo group and an iodo group; a $C_{1-6}$ alkoxy group such as a methoxy group, an ethoxy group, an n-propoxy group, an i-propoxy group, an n-butoxy group, an s-butoxy group, an i-butoxy group and a t-butoxy group; a $C_{1-6}$ haloalkoxy group such as a 2-chloro-n-propoxy group, a 2,3-dichlorobutoxy group and a trifluoromethoxy group; and a cyano group.

$X^1$ is preferably a halogeno group, a substituted or unsubstituted $C_{1-6}$ alkyl group, a substituted or unsubstituted $C_{1-6}$ alkoxy group, a formyl group, a substituted or unsubstituted $C_{1-6}$ alkoxycarbonyl group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{6-10}$ aryl group, a substituted or unsubstituted heteroaryl group, a substituted or unsubstituted $C_{6-10}$ aryloxy group, a nitro group, a cyano group, pentafluorosulfanyl, or a group represented by the formula: "$R^aO—N=CR^b—$" (in the formula, $R^a$ represents a hydrogen atom, or a substituted or unsubstituted $C_{1-6}$ alkyl group, and $R^b$ represents a hydrogen atom, or a substituted or unsubstituted $C_{1-6}$ alkyl group).

As the "substituted or unsubstituted $C_{1-6}$ alkyl group", a halogeno-substituted, $C_{1-6}$ alkoxy-substituted or unsubstituted $C_{1-6}$ alkyl group is preferable.

As the "substituted or unsubstituted $C_{1-6}$ alkoxy group", a halogeno-substituted or unsubstituted $C_{1-6}$ alkoxy group is preferable.

As the "substituted or unsubstituted $C_{1-6}$ alkylthio group", a halogeno-substituted or unsubstituted $C_{1-6}$ alkylthio group is preferable.

As the "substituted or unsubstituted $C_{1-6}$ alkylsulfinyl group", a halogeno-substituted or unsubstituted $C_{1-6}$ alkylsulfinyl group is preferable.

As the "substituted or unsubstituted $C_{1-6}$ alkylsulfonyl group", a halogeno-substituted or unsubstituted $C_{1-6}$ alkylsulfonyl group is preferable.

As the "group represented by the formula: $R^aO—N=CR^b—$", a group in which $R^a$ is a halogeno-substituted or unsubstituted $C_{1-6}$ alkyl group and $R^b$ is a hydrogen atom is preferable.

Examples of the divalent organic group formed by the two $X^1$ groups together include $C_{3-6}$ alkylene groups such as a trimethylene group, a tetramethylene group and a pentamethylene group; $C_{1-6}$ alkylenedioxy groups such as a methylenedioxy group and an ethylenedioxy group; $C_{1-6}$ haloalkylenedioxy groups such as a difluoromethylenedioxy group and a tetrafluoroethylenedioxy group; and the like.

[Compound Represented by Formula (III)]

The cyclic compound of the present invention is more preferably a compound represented by a formula (III).

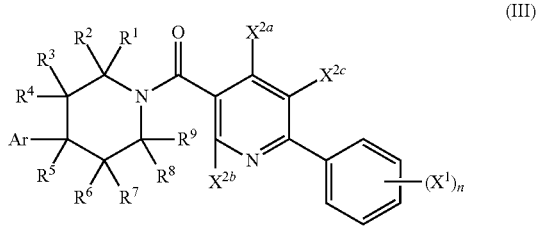

(III)

In the formula (III), $R^1$ to $R^4$, $R^6$ to $R^9$, $R^5$ and Ar are the same as those defined in the formula (I).

$X^1$ is the same as defined above n represents any one of integers 0 to 5. When there are 2 or more $X^1$ groups, $X^1$ groups may be the same as or different from each other.

$X^{2a}$ represents a hydrogen atom, or is the same as $X^2$ defined in the formula (I). $X^{2b}$ represents a hydrogen atom, or is the same as $X^2$ defined in the formula (I). $X^{2c}$ is the same as $X^2$ defined in the formula (I).

$X^{2b}$ is preferably $X^2$.

The cyclic amine compound of the present invention is excellent in the control effect of various agricultural pests and harmful organisms such as mites and ticks that adversely affect the growth of plants.

In addition, the cyclic amine compound of the present invention is a highly safe compound because it has no phytotoxicity to crops and has low toxicity to fishes and warm-blooded animals. Therefore, it is useful as an active ingredient of insecticides or acaricides.

Furthermore, in recent years, resistance to various existing drugs has developed in a number of insect pests such as diamondback moths, planthoppers, leafhoppers and aphids, causing problems of insufficient efficacy of these drugs, and drugs that are effective even against resistant strains of insect pests have been desired. The cyclic amine compound of the present invention has an excellent controlling effect not only on susceptible strains but also on various resistant strains of insect pests and acaricide-resistant strains of mites and ticks.

The cyclic amine compound of the present invention is excellent in controlling the ectoparasites which harm humans and animals. In addition, it is a highly safe compound because of its low toxicity to fishes and warm-blooded animals. Therefore, it is useful as an active ingredient of an ectoparasite controlling agent.

In addition, the cyclic amine compound of the present invention shows efficacy in all developmental stages of organisms to be controlled, and has an excellent control effect, for example, on eggs, nymphs, larvae, pupae and adults of mites and ticks, insects and the like.

[Pest Control Agent, Insecticidal or Acaricidal Agent]

The pest control agent or the insecticidal or acaricidal agent of the present invention contains at least one selected from cyclic amine compounds of the present invention as an active ingredient. The amount of the cyclic amine compound of the present invention contained in the pest control agent or the insecticidal or acaricidal agent of the present invention is not particularly limited as long as it shows the pest control effect.

The pest control agent or the insecticidal or acaricidal agent of the present invention is preferably used for grains; vegetables; root vegetables; potatoes; flowers and ornamental plants; fruit trees, foliage plants and trees of tea, coffee, cacao and the like; pasture grasses; turf grasses; and plants such as cotton.

In application to plants, the pest control agent or the insecticidal or acaricidal agent of the present invention may be used to any portions of leaves, stems, stalks, flowers, buds, fruits, seeds, sprouts, roots, tubers, tuberous roots, shoots, cuttings and the like. Further, the pest control agent or the insecticidal or acaricidal agent of the present invention is not particularly limited depending on the species of the plant to be applied. Examples of the plant species include an original species, a variant species, an improved variety, a cultivar, a mutant, a hybrid and a genetically modified organism (GMO).

The pest control agent of the present invention can be used for seed treatment, foliage application, soil application, water surface application and the like, in order to control various agricultural pests and mites and ticks.

Specific examples of various agricultural pests and mites and ticks which can be controlled by the pest control agent of the present invention are shown below.

(1) Butterflies or Moths of the Order Lepidoptera (a) Moths of the family Arctiidae such as *Hyphantria cunea* and *Lemyra imparilis*;

(b) moths of the family Bucculatricidae such as *Bucculatrix pyrivorella*;

(c) moths of the family Carposinidae such as *Carposina sasakii*;

(d) moths of the family Crambidae, for example, species belonging to the genus *Diaphania* (*Diaphania* spp.) such as *Diaphania indica* and *Diaphania nitidalis*; for example, species belonging to the genus *Ostrinia* (*Ostrinia* spp.) such as *Ostrinia furnacalis*, *Ostrinia nubilalis* and *Ostrinia scapulalis*; and others such as *Chilo suppressalis, Cnaphalocrocis medinalis, Conogethes punctiferalis, Diatraea grandiosella, Glyphodes pyloalis, Hellula undalis* and *Parapediasia teterrella*;

(e) moths of the family Gelechiidae such as *Helcystogramma triannulella, Pectinophora gossypiella, Phthorimaea operculella* and *Sitotroga cerealella*;

(f) moths of the family Geometridae such as *Ascotis selenaria*;

(g) moths of the family Gracillariidae such as *Caloptilia theivora, Phyllocnistis citrella* and *Phyllonorycter ringoniella*;

(h) butterflies of the family Hesperiidae such as *Parnara guttata*;

(i) moths of the family Lasiocampidae such as *Malacosoma neustria*;

(j) moths of the family Lymantriidae, for example, species belonging to the genus *Lymantria* (*Lymantria* spp.) such as *Lyinantria dispar* and *Lyinantria inonacha*; and others such as *Euproctis pseudoconspersa* and *Orgyia thyellina*;

(k) moths of the family Lyonetiidae, for example, species belonging to the genus *Lyonetia* (*Lyonetia* spp.) such as *Lyonetia clerkella* and *Lyonetia prunifoliella malinella*;

(l) moths of the family Noctuidae, for example, species belonging to the genus *Spodoptera* (*Spodoptera* spp.) such as *Spodoptera depravata, Spodoptera eridania, Spodoptera exigua, Spodoptera frugiperda, Spodoptera littoralis* and *Spodoptera litura*; for example, species belonging to the genus *Autographa* (*Autographa* spp.) such as *Autographa gamma* and *Autographa nigrisigna*; for example, species belonging to the genus *Agrotis* (*Agrotis* spp.) such as *Agrotis Ipsilon* and *Agrotis segetum*; for example, species belonging to the genus *Helicoverpa* (*Helicoverpa* spp.) such as *Helicoverpa armigera, Helicoverpa assulta* and *Helicoverpa zea*; for example, species belonging to the genus *Heliothis* (*Heliothis* spp.) such as *Heliothis armigera* and *Heliothis virescens*; and others such as *Aedia leucomelas, Ctenoplusia agnata, Eudocima tyrannus, Mamestra brassicae, Mythimna separata, Naranga aenescens, Panolis japonica, Peridroma saucier, Pseudoplusia includens* and *Tritoplusia ni*;

(m) moths of the family Nolidae such as *Earias insulana*;

(n) butterflies of the family Pieridae, for example, species belonging to the genus *Pieris* (*Pieris* spp.) such as *Pieris brassicae* and *Pieris rapae crucivora*;

(o) moths of the family Plutellidae, for example, species belonging to the genus *Acrolepiopsis* (*Acrolepiopsis* spp.) such as *Acrolepiopsis sapporensis* and *Acrolepiopsis suzukiella*; and others such as *Plutella xylostella*;

(p) moths of the family Pyralidae such as *Cadra cautella, Elasmopalpus lignosellus, Etiella zinckenella* and *Galleria mellonella*;

(q) moths of the family Sphingidae, for example, species belonging to the genus *Manduca* (*Manduca* spp.) such as *Manduca quinquemaculata* and *Manduca sexta*;

(r) moths of the family Stathmopodidae such as *Stathmopoda masinissa*;

(s) moths of the family Tineidae such as *Tinea translucens*;

(t) moths of the family Tortricidae, for example, species belonging to the genus *Adoxophyes* (*Adoxophyes* spp.) such as *Adoxophyes honmai* and *Adoxophyes orana*; for example, species belonging to the genus *Archips* (*Archips* spp.) such as *Archips breviplicanus* and *Archips fuscocupreanus*; and others such as *Choristoneura fumiferana, Cydia pomonella, Eupoecilia ambiguella, Grapholitha inolesta, Homona inagnanima, Leguminivora glycinivorella, Lobesia botrana, Matsumuraeses phaseoli, Pandetmis heparana* and *Sparganothis pilleriana*; and (u) moths of the family Yponomeutidae such as *Argyresthia conjugella*;

(2) Insect Pests of the Order Thysanoptera (a) pests of the family Phlaeothripidae such as *Ponticulothrips diospyrosi*; and (b) pests of the family Thripidae, for example, species belonging to the genus *Frankliniella* (*Frankliniella* spp.) such as *Frankliniella intonsa* and *Frankliniella occidentalis*; for example, species belonging to the genus *Thrips* (*Thrips* spp.) such as *Thrips palmi* and *Thrips tabaci*; and others such as *Heliothrips haemorrhoidalis* and *Scirtothrips dorsalis*.

(3) Insect Pests of the Order Hemiptera (A) Archaeorrhyncha (a) pests of the family Delphacidae such as *Laodelphax striatella, Nilaparvata lugens, Perkinsiella saccharicida* and *Sogatella furcifera*.

(B) Clypeorrhyncha (a) pests of the family Cicadellidae, for example, species belonging to the genus *Empoasca* (*Empoasca* spp.) such as *Empoasca fabae, Empoasca nipponica, Empoasca onukii* and *Empoasca sakaii*; and others such as *Arboridia apicalis, Balclutha saltuella, Epiacanthus stramineus, Macrosteles striifrons* and *Nephotettix cinctinceps*.

(C) Heteroptera (a) pests of the family Alydidae such as *Riptortus clavatus*;

(b) pests of the family Coreidae such as *Cletus punctiger* and *Leptocorisa chinensis*;

(c) pests of the family Lygaeidae such as *Blissus leucopterus, Cavelerius saccharivorus* and *Togo hemipterus*;

(d) pests of the family Miridae such as *Halticus insularis, Lygus lineolaris, Psuedatomoscelis seriatus, Stenodema sibiricum, Stenotus rubrovittatus* and *Trigonotylus caelestialium*;

(e) pests of the family Pentatomidae, for example, species belonging to the genus *Nezara* (*Nezara* spp.) such as *Nezara antennata* and *Nezara viridula*; for example, species belonging to the genus *Eysarcoris* (*Eysarcoris* spp.) such as *Eysarcoris aeneus, Eysarcoris lewisi* and *Eysarcoris ventralis*; and others such as *Dolycoris baccarum, Eurydema rugosum, Glaucias subpunctatus, Halyomorpha halys, Piezodorus hybneri, Plautia crossota* and *Scotinophora lurida*;

(f) pests of the family Pyrrhocoridae such as *Dysdercus cingulatus*;

(g) pests of the family Rhopalidae such as *Rhopalus msculatus*;

(h) pests of the family Scutelleridae such as *Eurygaster integriceps*; and (i) pests of the family Tingidae such as *Stephanitis nashi*.

(D) Sternorrhyncha (a) pests of the family Adelgidae such as *Adelges laricis*;

(b) pests of the family Aleyrodidae, for example, species belonging to the genus *Bemisia* (*Bemisia* spp.) such as *Bemisia argentifolii* and *Bemisia tabaci*; and others such as *Aleurocanthus spiniferus, Dialeurodes citri* and *Trialeurodes vaporariorum*;

(c) pests of the family Aphididae, for example, species belonging to the genus *Aphis* (*Aphis* spp.) such as *Aphis craccivora, Aphis fabae, Aphis forbesi, Aphis gossypii, Aphis pomi, Aphis sambuci* and *Aphis spiraecola*; for example, species belonging to the genus *Rhopalosiphum* (*Rhopalosiphum* spp.) such as *Rhopalosiphum maidis* and *Rhopalosiphum padi*; for example, species belonging to the genus *Dysaphis* (*Dysaphis* spp.) such as *Dysaphis plantaginea* and *Dysaphis radicola*; for example, species belonging to the genus *Macrosiphum* (*Macrosiphum* spp.) such as *Macrosiphum avenae* and *Macrosiphum euphorbiae*; for example, species belonging to the genus *Myzus* (*Myzus* spp.) such as *Myzus cerasi, Myzus persicae* and *Myzus varians*; and others such as *Acyrthosiphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodonhumuli, Schizaphis graminum, Sitobion avenae* and *Toxoptera aurantii*;

(d) pests of the family Coccidae, for example, species belonging to the genus *Ceroplastes* (*Ceroplastes* spp.) such as *Ceroplastes ceriferus* and *Ceroplastes rubens*;

(e) pests of the family Diaspididae, for example, species belonging to the genus *Pseudaulacaspis* (*Pseudaulacaspis* spp.) such as *Pseudaulacaspis pentagona* and *Pseudaulacaspis prunicola*; for example, species belonging to the genus *Unaspis* (*Unaspis* spp.) such as *Unaspis euonymi* and *Unaspis yanonensis*; and others such as *Aonidiella aurantii*, *Comstockaspis perniciosa*, *Fiorinia theae* and *Pseudaonidia paeoniae*;

(f) pests of the family Margarodidae such as *Drosicha corpulenta* and *Icerya purchasi*;

(g) pests of the family Phylloxeridae such as *Viteus vitifolii*;

(h) pests of the family Pseudococcidae, for example, species belonging to the genus *Planococcus* (*Planococcus* spp.) such as *Planococcus citri* and *Planococcus kuraunhiae*; and others such as *Phenacoccus solani* and *Pseudococcus comstocki*; and (i) pests of the family Psyllidae, for example, species belonging to the genus *Psylla* (*Psylla* spp.) such as *Psylla mali* and *Psylla pyrisuga*; and others such as *Diaphorina citri*.

(4) Insect Pests of the Suborder Polyphaga (a) pests of the family Anobiidae such as *Lasioderma serricorne*;

(b) pests of the family Attelabidae such as *Byctiscus betulae* and *Rhynchites heros*;

(c) pests of the family Bostrichidae such as *Lyctus brunneus*;

(d) pests of the family Brentidae such as *Cylas formicarius*;

(e) pests of the family Buprestidae such as *Agrilus sinuatus*;

(f) pests of the family Cerambycidae such as *Anoplophora malasiaca*, *Monochamus alternatus*, *Psacothea hilaris* and *Xylotrechus pyrrhoderus*;

(g) pests of the family Chrysomelidae, for example, species belonging to the genus *Bruchus* (*Bruchus* spp.) such as *Bruchus pisorum* and *Bruchus rufimanus*; for example, species belonging to the genus *Diabrotica* (*Diabrotica* spp.) such as *Diabrotica barberi*, *Diabrotica undecimpunctata* and *Diabrotica virgifera*; for example, species belonging to the genus *Phyllotreta* (*Phyllotreta* spp.) such as *Phyllotreta nemorum* and *Phyllotreta striolata*; and others such as *Aulacophora femoralis*, *Callosobruchus chinensis*, *Cassida nebulosa*, *Chaetocnema concinna*, *Leptinotarsa decemlineata*, *Oulema oryzae* and *Psylliodes angusticollis*;

(h) pests of the family Coccinellidae, for example, species belonging to the genus *Epilachna* (*Epilachna* spp.) such as *Epilachna varivestis* and *Epilachna vigintioctopunctata*;

(i) pests of the family Curculionidae, for example, species belonging to the genus *Anthonomus* (*Anthonomus* spp.) such as *Anthonomus grandis* and *Anthonomus pomorum*; for example, species belonging to the genus *Sitophilus* (*Sitophilus* spp.) such as *Sitophilus granarius* and *Sitophilus zeamais*; and others such as *Echinocnemus squameus*, *Euscepes postfasciatus*, *Hylobius abietis*, *Hypera postica*, *Lissohoptrus oryzophilus*, *Otiorhynchus sulcatus*, *Sitona lineatus* and *Sphenophorus venatus*;

(j) pests of the family Elateridae, for example, species belonging to the genus *Melanotus* (*Melanotus* spp.) such as *Melanotus fortnumi* and *Melanotus tamsuyensis*;

(k) pests of the family Nitidulidae such as *Epuraea domina*;

(l) pests of the family Scarabaeidae, for example, species belonging to the genus *Anomala* (*Anomala* spp.) such as *Anomala cuprea* and *Anomala rufocuprea*; and others such as *Cetonia aurata*, *Gametis jucunda*, *Heptophylla picea*, *Melolontha melolontha* and *Popillia japonica*;

(m) pests of the family Scolytidae such as *Ips typographus*;

(n) pests of the family Staphylinidae such as *Paederus fuscipes*;

(o) pests of the family Tenebrionidae such as *Tenebrio molitor* and *Tribolium castaneum*; and (p) pests of the family Trogossitidae such as *Tenebroides mauritanicus*.

(5) Insect Pests of the Order Diptera (A) Brachycera (a) pests of the family Agromyzidae, for example, species belonging to the genus *Liriomyza* (*Liriomyza* spp.) such as *Liriomyza bryoniae*, *Liriomyza chinensis*, *Liriomyza sativae* and *Liriomyza trifolii*; and others such as *Chromatomyia horticola* and *Agromyza oryzae*;

(b) pests of the family Anthomyiidae, for example, species belonging to the genus *Delia* (*Delia* spp.) such as *Delia platura* and *Delia radicum*; and others such as *Pegomya cunicularia*;

(c) pests of the family Drosophilidae, for example, species belonging to the genus *Drosophila* (*Drosophila* spp.) such as *Drosophila melanogaster* and *Drosophila suzukii*;

(d) pests of the family Ephydridae such as *Hydrellia griseola*;

(e) pests of the family Psilidae such as *Psila rosae*; and (f) pests of the family Tephritidae, for example, species belonging to the genus *Bactrocera* (*Bactrocera* spp.) such as *Bactrocera cucurbitae* and *Bactrocera dorsalis*; for example, species belonging to the genus *Rhagoletis* (*Rhagoletis* spp.) such as *Rhagoletis cerasi* and *Rhagoletis pomonella*; and others such as *Ceratitis capitata* and *Dacus oleae*.

(B) Nematocera (a) pests of the family Cecidomyiidae such as *Asphondylia yushimai*, *Contarinia sorghicola*, *Mayetiola destructor* and *Sitodiplosis mosellana*.

(6) Insect Pests of the Order Orthoptera (a) pests of the family Acrididae, for example, species belonging to the genus *Schistocerca* (*Schistocerca* spp.) such as *Schistocerca americana* and *Schistocerca gregaria*; and others such as *Chortoicetes terminifera*, *Dociostaurus maroccanus*, *Locusta migratoria*, *Locustana pardalina*, *Nomadacris septemfasciata* and *Oxya yezoensis*;

(b) pests of the family Gryllidae such as *Acheta domestica* and *Teleogryllus emma*;

(c) pests of the family Gryllotalpidae such as *Gryllotalpa orientalis*; and (d) pests of the family Tettigoniidae such as *Tachycines asynamorus*.

(7) Acari (A) Acaridida of the Order Astigmata (a) mites of the family Acaridae, for example, species belonging to the genus *Rhizoglyphus* (*Rhizoglyphus* spp.) such as *Rhizoglyphus echinopus* and *Rhizoglyphus robini*; for example, species belonging to the genus *Tyrophagus* (*Tyrophagus* spp.) such as *Tyrophagus neiswanderi*, *Tyrophagus perniciosus*, *Tyrophagus putrescentiae* and *Tyrophagus similis*; and others such as *Acarus siro*, *Aleuroglyphus ovatus* and *Mycetoglyphus fungivorus*;

(B) Actinedida of the Order Prostigmata (a) mites of the family Tetranychidae, for example, species belonging to the genus *Bryobia* (*Bryobia* spp.) such as *Bryobia praetiosa* and *Bryobia rubrioculus*; for example, species belonging to the genus *Eotetranychus* (*Eotetranychus* spp.) such as *Eotetranychus asiaticus*, *Eotetranychus boreus*, *Eotetranychus celtis*, *Eotetranychus geniculatus*,

*Eotetranychus kankitus, Eotetranychus pruni, Eotetranychus shii, Eotetranychus smithi, Eotetranychus suginamensis* and *Eotetranychus uncatus*; for example, species belonging to the genus *Oligonychus* (*Oligonychus* spp.) such as *Oligonychus hondoensis, Oligonychus ilicis, Oligonychus karatnatus, Oligonychus mangiferus, Oligonychus orthius, Oligonychus perseae, Oligonychus pustulosus, Oligonychus shinkajii* and *Oligonychus ununguis*; for example, species belonging to the genus *Panonychus* (*Panonychus* spp.) such as *Panonychus citri, Panonychus mori* and *Panonychus ulmi*; for example, species belonging to the genus *Tetranychus* (*Tetranychus* spp.) such as *Tetranychus cinnabarinus, Tetranychus kanzawai, Tetranychus ludeni, Tetranychus quercivorus, Tetranychus phaselus, Tetranychus urticae* and *Tetranychus viennensis*; for example, species belonging to the genus *Aponychus* (*Aponychus* spp.) such as *Aponychus corpuzae* and *Aponychus firmianae*; for example, species belonging to the genus *Sasanychus* (*Sasanychus* spp.) such as *Sasanychus akitanus* and *Sasanychus pusillus*; for example, species belonging to the genus *Shizotetranychus* (*Shizotetranychus* spp.) such as *Shizotetranychus celarius, Shizotetranychus longus, Shizotetranychus miscanthi, Shizotetranychus recki* and *Shizotetranychus schizopus*; and others such as *Tetranychina harti, Tuckerella pavoniformis* and *Yezonychus sapporensis;*

(b) mites of the family Tenuipalpidae, for example, species belonging to the genus *Brevipalpus* (*Brevipalpus* spp.) such as *Brevipalpus lewisi, Brevipalpus obovatus, Brevipalpus phoenicis, Brevipalpus russulus* and *Brevipalpus californicus*; for example, species belonging to the genus *Tenuipalpus* (*Tenuipalpus* spp.) such as *Tenuipalpus pacificus* and *Tenuipalpus zhizhilashviliae*; and others such as *Dolichotetranychus floridanus;*

(c) mites of the family Eriophyidae, for example, species belonging to the genus *Aceria* (*Aceria* spp.) such as *Aceria diospyri, Aceria ficus, Aceria japonica, Aceria kuko, Aceria paradianthi, Aceria tiyingi, Aceria tulipae* and *Aceria zoysiea*; for example, species belonging to the genus *Eriophyes* (*Eriophyes* spp.) such as *Eriophyes chibaensis* and *Eriophyes emarginatae*; for example, species belonging to the genus *Aculops* (*Aculops* spp.) such as *Aculops lycopersici* and *Aculops pelekassi*; for example, species belonging to the genus *Aculus* (*Aculus* spp.) such as *Aculus fockeui* and *Aculus schlechtendali*; and others such as *Acaphylla theavagrans, Calacarus carinatus, Colomerus vitis, Calepitrimerus vitis, Epitrimerus pyri, Paraphytoptus kikus, Paracalacarus podocarpi* and *Phyllocotruta citri;*

(d) mites of the family Transonemidae, for example, species belonging to the genus *Tarsonemus* (*Tarsonemus* spp.) such as *Tarsonemus bilobatus* and *Tarsonemus waitei*; and others such as *Phytonemus pallidus* and *Polyphagotarsonemus latus*; and (e) mites of the family Penthaleidae, for example, species belonging to the genus *Penthaleus* (*Penthaleus* spp.) such as *Penthaleus erythrocephalus* and *Penthaleus major.*

The pest control agent or the insecticidal or acaricidal agent of the present invention may contain components other than the cyclic amine compound of the present invention. As other components, known carriers used for formulation and the like can be mentioned. In addition, as other components, conventionally known fungicides, insecticidal/acaricidal agents, nematicides, soil pesticides, plant regulators, synergists, fertilizers, soil conditioners, animal feeds and the like can be mentioned. By including such other components, synergistic effects may be obtained.

Specific examples of insecticidal/acaricidal agents, nematicides, soil pesticides, anthelmintics and the like which can be mixed with or used in combination with the pest control agent of the present invention are shown below.

(1) Acetylcholinesterase inhibitor:

(a) carbamate-based inhibitors: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam sodium, promecarb;

(b) Organophosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion; bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, sulprofos.

(2) GABA-gated chloride ion channel antagonists: acetoprole, chlordane, endosulfan, ethiprole, fipronil, pyrafluprole, pyriprole; camphechlor, heptachlor, dienochlor.

(3) Sodium channel modulators: acrinathrin, d-cis/trans allethrin, d-trans-allethrin, bifenthrin, bioallethrin, bioallethrin S-cyclopentyl isomers, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomers], prallethrin, pyrethrum, resmethrin, silafluofen, tefluthrin, tetramethrin [(1R)-isomers], tralomethrin, transfluthrin, allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone.

(5) Nicotinic acetylcholine receptor allosteric modulators: spinetoram, spinosad.

(6) Chloride channel activators: abamectin, emamectin benzoate, lepimectin, milbemectin; ivermectin, selamectin, doramectin, eprinomectin, moxidectin, milbemycin, milbemycin oxime, nemadectin.

(7) Juvenile hormone analogues: hydroprene, kinoprene, methoprene, fenoxycarb, pyriproxyfen; diofenolan, epofenonane, triprene.

(8) Other nonspecific inhibitors: methyl bromide, chloropicrin, sulfuryl fluoride, borax, tartar emetic.

(9) Homoptera selective antifeedants: flonicamid, pymetrozine, pyrifluquinazone.

(10) Mite growth inhibitors: clofentezine, diflovidazin, hexythiazox, etoxazole.

(11) Insect midgut inner membrane disrupting agents derived from microorganisms: *Bacillus thuringiensis* subsp. *israelensi*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, Bt crop proteins: Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondrial ATP biosynthetic enzyme inhibitors: diafenthiuron, azocyclotin, cyhexatin, fenbutatin oxide, propargite, tetradifon.

(13) Oxidative phosphorylation uncouplers: chlorfenapyr, sulfluramid, DNOC; binapacryl, dinobuton, dinocap.

(14) Nicotinic acetylcholine receptor channel blockers: bensultap, cartap hydrochloride; nereistoxin; thiosultap monosodium salt, thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron.

(16) Diptera molting disrupting agents: cyromazine

(17) Molting hormone receptor agonists: chromafenozide, halofenozide, methoxyfenozide, tebufenozide.

(18) Octopamine receptor agonists: amitraz, demiditraz, chlordimeform.

(19) Mitochondrial electron transport system complex III inhibitors: acequinocyl, fluacrypyrim, hydramethylnon.

(20) Mitochondrial electron transport system complex I inhibitors: fenazaquin, fenpyroximate, pyrimidifen, pyridaben, tebufenpyrad, tolfenpyrad, rotenone.

(21) Voltage-dependent sodium channel blockers: indoxacarb, metaflumizone.

(22) Acetyl CoA carboxylase inhibitors: spirodiclofen, spiromesifen, spirotetramat.

(23) Mitochondrial electron transport system complex IV inhibitors: aluminum phosphide, calcium phosphide, phosphine, zinc phosphide, cyanide.

(24) Mitochondrial electron transport system complex II inhibitors: cyenopyrafen, cyflumetofen, pyflubumide.

(25) Ryanodine receptor modulators: chlorantraniliprole, cyantraniliprole, flubendiamide, cyclaniliprole, tetraniliprole.

(26) Mixed function oxidase inhibitor compounds: piperonyl butoxide.

(27) Latrophilin receptor agonists: depsipeptide, cyclic depsipeptide, 24-membered cyclic depsipeptide, emodepside.

(28) Other agents (with unknown action mechanisms): azadirachtin, benzoximate, bifenazate, bromopropylate, chinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure, japonilure, metoxadiazone, petroleum, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl) benzonitrile (CAS: 943137-49-3), broflanilide, other meta-diamides.

(29) Anthelmintics:

(a) benzimidazole-based: fenbendazole, albendazole, triclabendazole, oxybendazole, mebendazole, oxfendazole, parbendazole, flubendazole; febantel, netobimin, thiophanate; thiabendazole, cambendazole;

(b) salicylanilide-based: closantel, oxyclozanide, rafoxanide, niclosamide;

(c) substituted phenol-based: nitroxinil, nitroscanate;

(d) pyrimidine-based: pyrantel, morantel;

(e) imidazothiazole-based: levamisole, tetramisole;

(f) tetrahydropyrimidine-based: praziquantel, epsiprantel; and (g) other anthelmintics: cyclodien, ryania, clorsulon, metronidazole, demiditraz; piperazine, diethylcarbamazine, dichlorophen, monepantel, tribendimidine, amidantel; thiacetarsamide, melorsamine, arsenamide.

Specific examples of the fungicide which can be mixed with or used in combination with the pest control agent of the present invention are shown below.

(1) Nucleic acid biosynthesis inhibitors:

(a) RNA polymerase 1 inhibitors: benalaxyl, benalaxyl-M, furalaxyl, metalaxyl, metalaxyl-M; oxadixyl; clozylacon, ofurace;

(b) adenosine deaminase inhibitors: bupirimate, dimethirimol, ethirimol;

(c) DNA/RNA synthesis inhibitors: hymexazol, octhilinone;

(d) DNA topoisomerase 11 inhibitors: oxolinic acid.

(2) Mitotic inhibitors and cell division inhibitors:

(a) β-tubulin polymerization inhibitors: benomyl, carbendazim, chlorfenazole, fuberidazole, thiabendazole; thiophanate, thiophanate methyl; diethofencarb; zoxamide; ethaboxam;

(b) cell division inhibitors: pencycuron;

(c) delocalization inhibitors of spectrin-like protein: fluopicolide.

(3) Respiration inhibitors:

(a) complex I NADH oxidoreductase inhibitors: diflumetorim; tolfenpyrad;

(b) complex II succinate dehydrogenase inhibitors: benodanil, flutolanil, mepronil; isofetamid; fluopyram; fenfuram, furmecyclox; carboxin, oxycarboxin; thifluzamide; benzovindiflupyr, bixafen, fluxapyroxad, furametpyr, isopyrazam, penflufen, penthiopyrad, sedaxane; boscalid; pyraziflumid;

(c) complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoxim-methyl, trifloxystrobin; dimoxystrobin, fenaminstrobin, metominostrobin, orysastrobin; famoxadone; fluoxastrobin; fenamidone; pyribencarb; mandestrobin;

(d) complex III ubiquinol reductase Qi inhibitors: cyazofamid; amisulbrom;

(e) oxidative phosphorylation uncouplers: binapacryl, meptyldinocap, dinocap; fluazinam; ferimzone;

(f) oxidative phosphorylation inhibitors (ATP synthase inhibitors): fentin acetate, fentin chloride, fentin hydroxide;

(g) ATP production inhibitor: silthiofam;

(h) complex III: Qx (unknown) inhibitor of cytochrome bc1 (ubiquinone reductase): ametoctradin.

(4) Amino acid and protein synthesis inhibitors (a) methionine biosynthesis inhibitors: andoprim, cyprodinil, mepanipyrim, pyrimethanil;

(b) protein synthesis inhibitors: blasticidin S; kasugamycin, kasugamycin hydrochloride; streptomycin; oxytetracycline.

(5) Signal transduction inhibitors:
    (a) Signal transduction inhibitors: quinoxyfen, proquinazid;
    (b) MAP/histidine kinase inhibitors in osmotic signal transduction: fenpiclonil, fludioxonil; chlozolinate, iprodione, procymidone, vinclozolin.
(6) Lipid and cell membrane synthesis inhibitors:
    (a) phospholipid biosynthesis and methyltransferase inhibitors: edifenphos, iprobenfos, pyrazophos; isoprothiolane;
    (b) lipid peroxidation agents: biphenyl, chloroneb, dicloran, quintozene, tecnazene, tolclofos-methyl; etridiazole;
    (c) agents acting on cell membranes: iodocarb, propamocarb, propamocarb hydrochloride, propamocarb-fosetylate, prothiocarb;
    (d) microorganisms disturbing pathogenic cell membranes: *Bacillus subtilis, Bacillus subtilis* strain QST713, *Bacillus subtilis* strain FZB24, *Bacillus subtilis* strain MBI600, *Bacillus subtilis* strain D747;
    (e) agents disturbing cell membranes: extracts of Melaleuca alternifolia (tea tree).
(7) sterol biosynthesis inhibitors of cell membranes:
    (a) C14 position demethylation inhibitors in sterol biosynthesis: triforine; pyrifenox, pyrisoxazole; fenarimol, flurprimidol, nuarimol; imazalil, imazalil sulfate, oxpoconazole, pefurazoate, prochloraz, triflumizole, viniconazole; azaconazole, bitertanol, bromconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole; prothioconazole, voriconazole; mefentrifluconazole;
    (b) inhibitors of Δ14 reductase and Δ8→Δ7-isomerase in sterol biosynthesis: aldimorph, dodemorph, dodemorph acetate, fenpropimorph, tridemorph; fenpropidine, piperalin; spiroxamine;
    (c) 3-keto reductase inhibitors in C4 position demethylation in sterol biosynthesis system: fenhexamid; fenpyrazamine;
    (d) squalene epoxidase inhibitors in sterol biosynthesis system: pyributicarb; naftifine, terbinafine.
(8) Cell wall synthesis inhibitors
    (a) trehalase inhibitor: validamycin;
    (b) chitin synthetase inhibitors: polyoxins, polyoxorim;
    (c) cellulose synthetase inhibitors: dimethomorph, flumorph, pyrimorph; benthiavalicarb, iprovalicarb, tolprocarb, valifenalate; mandipropamid.
(9) Melanin biosynthesis inhibitors
    (a) reductase inhibitors in melanin biosynthesis: fthalide; pyroquilon; tricyclazole;
    (b) anhydrase inhibitors in melanin biosynthesis: carpropamid; diclocymet; fenoxanil;
    (c) other inhibitors: tolprocarb.
(10) Resistance inducers of host plants:
    (a) agents acting on salicylic acid synthetic pathway: acibenzolar-S-methyl;
    (b) other agents: probenazole; tiadinil; isotianil; laminarin; extraction liquid of Fallopia sachalinensis.
(11) agents with unknown actions: cymoxanil, fosetyl-aluminium, phosphoric acid (phosphates), tecloftalam, triazoxide, flusulfamide, diclomezine, methasulfocarb, cyflufenamid, metrafenone, pyrifenone, dodine, dodine free base, flutianil.

(12) agents having multiple points of action: copper (copper salts), Bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine acetates (iminoctadine triacetate), iminoctadine albesilates (iminoctadine trialbesilate); anilazine; dithianon; chinomethionate; fluoroimide.
(13) Other agents: DBEDC, fluor folpet, guazatine acetate, bis (8-quinolinolato) copper (II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophen, difenzoquat, difenzoquat methylsulfonate, flumetover, fosetyl calcium, fosetyl sodium, irumamycin, natamycin, nitrothal-isopropyl, oxamocarb, pyrrolnitrin, tebufloquin, tolnifanide, zarilamid, algophase, amicarthiazol, oxathiapiprolin, metiram zinc, benthiazole, trichlamide, uniconazole, mildiomycin, oxyfenthiin, picarbutrazox, fenpicoxamid, dichlobentiazox, quinofumelin.

Specific examples of plant regulators which can be mixed with or used in combination with the pest control agent of the present invention are shown below.

Abscisic acid, kinetin, benzylaminopurine, 1,3-diphenylurea, forchlorfenuron, thidiazuron, chlorphenuron, dihydroseatin, gibberellin A, gibberellin A4, gibberellin A7, gibberellin A3, 1-methylcyclopropane, N-acetyl aminoethoxyvinyl glycine (aka: abiglycine), aminooxyacetic acid, silver nitrate, cobalt chloride, IAA, 4-CPA, chloroprop, 2,4-D, MCPB, indole-3-butyric acid, dichlorprop, phenothiol, 1-naphthylacetamide, ethychlozate, croxyfonac, maleic hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl) amino butyric acid; ethephon, chlormequat, mepiquat chloride, benzyl adenine, 5-aminolevulinic acid.

[Ectoparasite Controlling Agent]

The ectoparasite controlling agent of the present invention contains at least one selected from cyclic amine compounds of the present invention as an active ingredient. The ectoparasite controlling agent of the present invention is excellent in controlling the ectoparasites which harm humans and animals.

Examples of ectoparasites include mites and ticks, lice, fleas, mosquitoes, stable flies, flesh flies and the like.

Examples of host animals to be treated with the ectoparasite controlling agent of the present invention include warm-blooded animals such as pet animals, for example, dogs, cats or the like; pet birds; domestic animals, for example, cattle, horses, pigs, sheep or the like; domestic fowls; and the like. In addition, honey bees, stag beetles and beetles can be exemplified.

The ectoparasites are parasitic in and on host animals, especially the warm-blooded animals. More specifically, the ectoparasites are parasitic in and on the back, armpit, lower abdomen, inner thigh and the like of the host animals and obtain nutritional sources such as blood and dandruff from the animals to live.

The ectoparasite controlling agent of the present invention can be applied by a known veterinary method (topical, oral, parenteral or subcutaneous administration). As a method therefor, a method of orally administering tablets, capsules, mixed feeds or the like to the animals; a method of administering to the animals by using an immersion liquid, suppository, injection (intramuscular, subcutaneous, intravenous, intraperitoneal or the like) or the like; a method of topically administering by spraying, pouring-on or spotting-on an oily or aqueous liquid preparation; a method of kneading an ectoparasite controlling agent in a resin, molding the kneaded product into an appropriate shape such as a collar, ear tag or the like, and attaching and topically administering the resultant to the animals; and the like can be mentioned.

Specific examples of the ectoparasites which can be controlled by the ectoparasite controlling agent of the present invention are shown below.

(1) Mites (Acari)

Mites belonging to the family Dermanyssidae, mites belonging to the family Macronyssidae, mites belonging to the family Laelapidae, mites belonging to the family Varroidae, mites belonging to the family Argasidae, mites belonging to the family Ixodidae, mites belonging to the family Psoroptidae, mites belonging to the family Sarcoptidae, mites belonging to the family Knemidokoptidae, mites belonging to the family Demodixidae, mites belonging to the family Trombiculidae, insect-parasitic mites such as *Coleopterophagus berlesei* or the like.

(2) Phthiraptera

Lice belonging to the family Haematopinidae, lice belonging to the family Linognathidae, chewing lice belonging to the family Menoponidae, chewing lice belonging to the family Philopteridae, chewing lice belonging to the family Trichodectidae;

(3) Siphonaptera

Fleas of the family Pulicidae, for example, species belonging to the genus *Ctenocephalides* (*Ctenocephalides* spp.) such as *Ctenocephalides canis* and *Ctenocephalides felis*; fleas belonging to the family Tungidae, fleas belonging to the family Ceratophyllidae, fleas belonging to the family Leptopsyllidae.

(4) Hemiptera.

(5) Insect Pests of the Order Diptera

Mosquitoes belonging to the family Culicidae, black flies belonging to the Simuliidae family, biting midges belonging to the family Ceratopogonidae, horseflies belonging to the family Tabanidae, flies belonging to the family Muscidae, tsetse flies belonging to the family Glossinidae; flesh flies belonging to the family Sarcophagidae, flies belonging to the family Hippoboscidae, flies belonging to the family Calliphoridae, flies belonging to the family Oestridae.

[Control Agents for Other Pests]

In addition, the ectoparasite controlling agent of the present invention is excellent in controlling insect pests having a stinger or venom which harm humans and animals, insect pests that mediate various pathogens/pathogenic microbes, and insect pests that cause discomfort to humans (such as toxic pests, hygiene pests and unpleasant pests).

Specific examples thereof are shown below.

(1) Insect Pests of the Order Hymenoptera

Bees belonging to the family Argidae, bees belonging to the family Cynipidae, bees belonging to the family Diprionidae, ants belonging to the family Formicidae, bees belonging to the family Mutillidae, bees belonging to the family Vespidae.

(2) Other Pests

Cockroaches (Blattodea), termites, spiders (Araneae), centipedes, millipedes, crustaceans, bedbugs (*Cimex lectularius*).

[Pharmaceutical Products for Treating Diseases or Conditions to Which Sodium Channel Inhibitors are Applied]

The cyclic amine compound of the present invention has an action as a sodium channel inhibitor.

The activity of sodium channels can be evaluated using various in vitro assays, including measurement of ion flows, measurement of membrane potential differences, and/or measurement of ionic currents. The measurement of ion flows can be made by measuring changes in the concentration of persistent species or by tracking the movement of a small amount of a suitable persistent radioactive tracer. The membrane potential difference can be measured with a voltage sensitive fluorescent dye, or more sensitively, by an electrophysiological method. In particular, changes in ion flows can be measured by determining the change in polarization (that is, electrical potential) of a cell, or of a membrane expressing a sodium channel. Preferred means for determining the polarization change of the cell are the voltage clamp method and the patch clamp method.

Sodium channel inhibitors have been reported to be effective in the treatment of various disease states and special uses have been found in the treatment of local anesthesia and cardiac asymmetry. Furthermore, it has also been reported that sodium channel inhibitors can be useful in the treatment of pain, including acute, chronic, inflammatory and neuropathic pain.

Therefore, the cyclic compound of the present invention serving as a sodium channel inhibitor is potentially useful for treating diseases of pain, especially neuropathic pain and inflammatory pain.

Examples of neuropathic pain include postherpetic neuralgia, trigeminal neuralgia, diabetic neuropathy, chronic low back pain, phantom limb pain, pain caused by cancer and chemotherapy, chronic pelvic pain, complex regional pain syndromes and related neuralgia. Further, it is also useful for treating epilepsy and cardiac arrhythmia in addition to neuropathic pain.

The present invention is also useful for a method of treating acute pain, chronic pain, visceral pain, inflammatory pain and neuropathic pain as well as CNS disorders, such as epilepsy, manic depression, depression, anxiety and bipolar disorder, which includes administering the cyclic compounds and pharmaceutical compositions of the present invention.

[Pharmaceutical Formulation]

Although some pharmaceutical formulations of the pest control agent, insecticide, acaricide and ectoparasite controlling agent of the present invention are shown, additives and the addition ratios should not be limited to these examples and can be modified over a wide range. The term "part" in the formulations indicates "part by weight".

The formulations for agricultural and horticultural use and for paddy rice are shown below.

(Formulation 1: Wettable Powder)

40 parts of the cyclic amine compound of the present invention, 53 parts of diatomaceous earth, 4 parts of a higher alcohol sulfuric acid ester and 3 parts of alkyl naphthalene sulfonate are uniformly mixed and finely pulverized to obtain a wettable powder containing 40% of an active ingredient.

(Formulation 2: Emulsion)

30 parts of the cyclic amine compound of the present invention, 33 parts of xylene, 30 parts of dimethylformamide and 7 parts of a polyoxyethylene alkyl allyl ether are mixed and dissolved to obtain an emulsion containing 30% of an active ingredient.

(Formulation 3: Granule)

5 parts of the cyclic amine compound of the present invention, 40 parts of talc, 38 parts of clay, 10 parts of bentonite and 7 parts of sodium alkylsulfate are uniformly mixed and finely pulverized, and then granulated into a granular form having a diameter of 0.5 to 1.0 mm to obtain a granule containing 5% of an active ingredient.

(Formulation 4: Granule)

5 parts of the cyclic amine compound of the present invention, 73 parts of clay, 20 parts of bentonite, 1 part of sodium dioctyl sulfosuccinate and 1 part of potassium phosphate are thoroughly ground and mixed, water is added and thoroughly kneaded, followed by granulation and drying to obtain a granule containing 5% of an active ingredient.

(Formulation 5: Suspension)

10 parts of the cyclic amine compound of the present invention, 4 parts of a polyoxyethylene alkyl allyl ether, 2 parts of a polycarboxylic acid sodium salt, 10 parts of glycerin, 0.2 parts of xanthan gum and 73.8 parts of water are mixed and subjected to wet grinding until the particle size becomes 3 microns or less to obtain a suspension containing 10% of an active ingredient.

The formulations of the ectoparasite controlling agent are shown below.

(Formulation 6: Granule)

5 parts of the cyclic amine compound of the present invention are dissolved in an organic solvent to obtain a solution, the solution is sprayed onto 94 parts of kaolin and 1 part of white carbon, and then the solvent is evaporated under reduced pressure. This type of granule can be mixed with animal feed.

(Formulation 7: Injection)

0.1 to 1 part of the cyclic amine compound of the present invention and 99 to 99.9 parts of peanut oil are uniformly mixed and then sterilized by filtration through a sterilizing filter.

(Formulation 8: Pour-On Agent)

5 parts of the cyclic amine compound of the present invention, 10 parts of a myristic acid ester and 85 parts of isopropanol are uniformly mixed to obtain a pour-on agent.

(Formulation 9: Spot-On Agent)

10 to 15 parts of the cyclic amine compound of the present invention, 10 parts of a palmitic acid ester and 75 to 80 parts of isopropanol are uniformly mixed to obtain a spot-on agent.

(Formulation 10: Spraying Agent)

1 part of the cyclic amine compound of the present invention, 10 parts of propylene glycol and 89 parts of isopropanol are uniformly mixed to obtain a spraying agent.

Next, the present invention will be described in more detail by showing examples. However, the present invention is in no way limited by the following examples.

Example 1

Production of 5-(4-(4-chlorophenyl)-4-hydroxypiperidine-1-carbonyl)-6-(difluoromethyl)-2-(4-(trifluoromethyl)phenyenicotinonitrile (Compound No. 1-1)

Step 1

Synthesis of ethyl 2-(ethoxymethylene)-4,4-difluoro-3-oxobutanoate

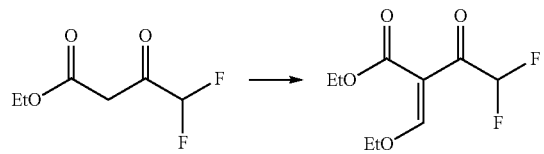 [SMILES: CCOC(=O)CC(=O)C(F)F ; CCO/C=C(\C(=O)OCC)C(=O)C(F)F]

8.3 g of ethyl 4,4-difluoroacetoacetate, 14.8 g of triethyl orthoformate and 41.9 g of acetic anhydride were mixed and heated under reflux for 5 hours. Thereafter, the reaction solution was concentrated under reduced pressure to obtain 11.1 g of a target compound. Yield: 100%

$^1$H-NMR (CDCl$_3$, δ ppm) 1.31 (3H, t), 1.43 (3H, t), 4.24-4.35 (4H, m), 6.20-6.55 (1H, m), 7.86 (1H, s)

Step 2

Synthesis of ethyl 5-cyano-2-(difluoromethyl)-6-hydroxynicotinate

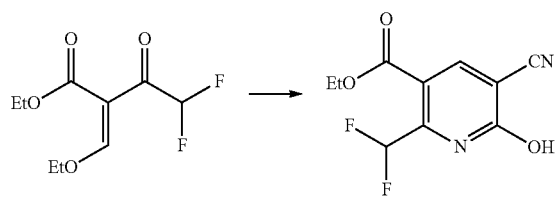 [SMILES: CCO/C=C(\C(=O)OCC)C(=O)C(F)F ; CCOC(=O)c1cc(C#N)c(O)nc1C(F)F]

1.27 g of sodium was dissolved in 50 ml of ethanol, and 4.62 g of cyanoacetic amide was added under ice cooling. Thereafter, 11.1 g of ethyl 2-(ethoxymethylene)-4,4-difluoro-3-oxobutanoate was added. The reaction solution was stirred at room temperature overnight, and dilute hydrochloric acid was added thereto to bring the pH to 1. The precipitated crystals were filtered and dried to obtain 9.94 g of a target compound. Yield: 82%

$^1$H-NMR (CDCl$_3$, δ ppm) 1.36 (3H, t), 4.34 (2H, q), 7.53 (1H, t), 8.39 (1H, s)

Step 3

Synthesis of ethyl 6-chloro-5-cyano-2-(difluoromethyl)-nicotinate

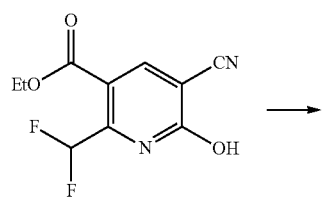

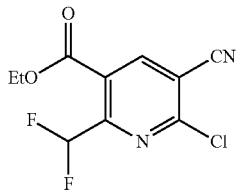

9.94 g of ethyl 5-cyano-2-(difluoromethyl)-6-hydroxynicotinate was suspended in 200 ml of dichloromethane, and 0.75 g of N,N-dimethylformamide and 26 g of oxalyl chloride were added under ice cooling. Thereafter, the resulting mixture was heated under reflux for 3 hours. The reaction solution was concentrated under reduced pressure, extracted with ethyl acetate, and washed sequentially with saturated aqueous sodium bicarbonate solution and saturated brine. The organic layer was dried over anhydrous magnesium sulfate. The solvent was distilled off under reduced pressure, and the obtained residue was purified by silica gel column chromatography (developing solvent: n-hexane/ethyl acetate) to obtain 10.8 g of a target compound. Yield: 100%.

$^1$H-NMR (CDCl$_3$, δ ppm) 1.43 (3H, t), 4.46 (2H, q), 7.39 (1H, t), 8.61 (1H, s)

Step 4

Synthesis of ethyl 5-cyano-2-(difluoromethyl)-6-(4-(trifluoromethyl)phenyl) nicotinate

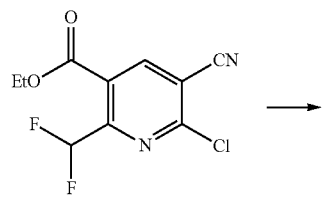

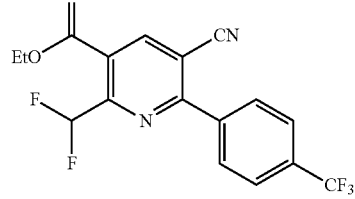

3.92 g of ethyl 6-chloro-5-cyano-2-(difluoromethyl)-nicotinate and 4.28 g of 4-trifluoromethylphenylboronic acid were dissolved in a mixed solvent of 80 ml of toluene and 8 ml of water, and 4.77 g of potassium carbonate and 0.53 g of dichlorobis [di-t-butyl (p-dimethylaminophenyl)phosphino] palladium (II) were added, and the resulting mixture was heated under reflux for 8 hours in a nitrogen atmosphere. The reaction solution was cooled to room temperature, poured into water and extracted with ethyl acetate. The organic layer was washed with saturated brine, and then dried over anhydrous magnesium sulfate. The solvent was distilled off under reduced pressure, and the obtained residue was purified by silica gel column chromatography (developing solvent: n-hexane/ethyl acetate) to obtain 5.04 g of a target compound. Yield: 91%.

$^1$H-NMR (CDCl$_3$, δ ppm) 1.41 (3H, t), 4.43 (2H, q), 6.91 (1H, t), 7.82 (2H, d), 8.09-8.11 (3H, m)

Step 5

Synthesis of 5-cyano-2-(difluoromethyl)-6-(4-(trifluoromethyl)phenyl) nicotinic acid

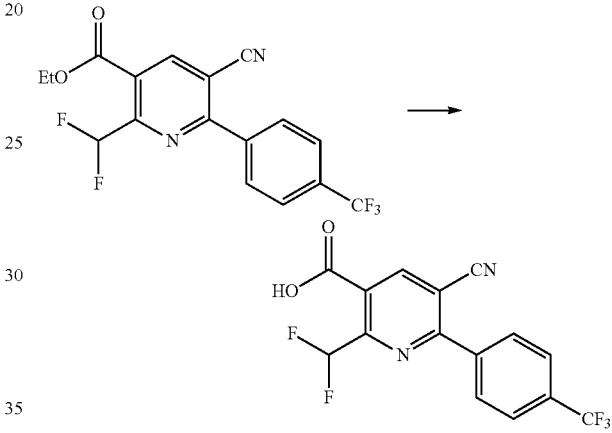

5.04 g of ethyl 5-cyano-2-(difluoromethyl)-6-(4-(trifluoromethyl)phenyl) nicotinate was dissolved in a mixed solvent of 40 ml of methanol and 20 ml of water, to which 1.1 g of sodium hydroxide was added, and the resulting mixture was stirred at room temperature for 2 hours. The reaction solution was concentrated under reduced pressure, then poured into dilute hydrochloric acid, and extracted with ethyl acetate. The organic layer was washed with saturated brine, and then dried over anhydrous magnesium sulfate. The solvent was distilled off under reduced pressure to obtain 4.42 g of a target compound. Yield: 95%.

$^1$H-NMR (CDCl$_3$, δ ppm) 6.95 (1H, t), 7.84 (2H, d), 8.10-8.13 (3H, m)

Step 6

Synthesis of 5-(4-(4-chlorophenyl)-4-hydroxypiperidine-1-carbonyl)-6-(difluoromethyl)-2-(4-(trifluoromethyl)phenyl) nicotinonitrile

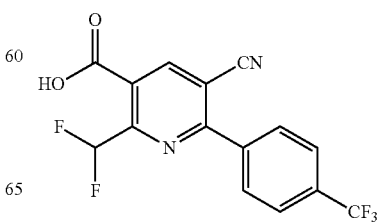

-continued

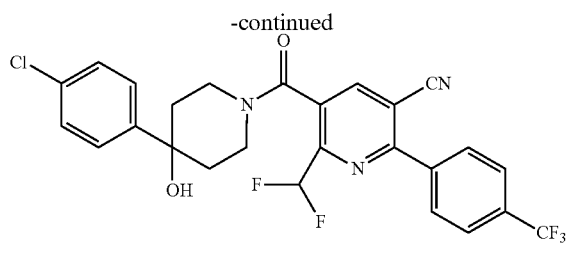

0.16 g of 5-cyano-2-(difluoromethyl)-6-(4-(trifluoromethyl)phenyl) nicotinic acid was suspended in 10 ml of dichloromethane, 0.2 g of 4-(4-chlorophenyl)-4-hydroxypiperidine, 0.11 g of 4-(N,N-dimethylamino) pyridine and 0.18 g of 1-[3-(diethylamino)propyl]-3-ethylcarbodiimide hydrochloride were added thereto, and the resulting mixture was stirred at room temperature overnight. The reaction solution was poured into ice water and extracted with chloroform. The resultant was washed sequentially with water and saturated brine. Thereafter, the resultant was dried over anhydrous magnesium sulfate. The solvent was distilled off under reduced pressure, and the obtained residue was purified by silica gel column chromatography (developing solvent: n-hexane/ethyl acetate) to obtain 0.1 g of a target compound. Yield: 40%

$^1$H-NMR (CDCl$_3$, δ ppm) 1.66-2.16 (4H, m), 3.34-3.43 (2H, m), 3.65-3.73 (1H, m), 4.67-4.77 (1H, m), 6.86 (1H, t), 7.33-7.42 (4H, m), 7.82 (2H, d), 8.10-8.12 (3H, m)

Example 2

Production of (4-(4-chlorophenyl)-4-hydroxypiperidin-1-yl) (6-(4-(trifluoromethyl)phenoxy) pyridin-3-yl) methanone (Compound No. 2-1)

Step 1

Synthesis of methyl 6-(4-(trifluoromethyl)phenoxy) nicotinate

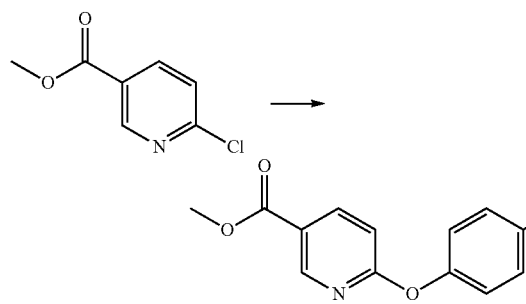

3.24 g of 4-trifluoromethylphenol was dissolved in 30 ml of dimethylsulfoxide and 0.88 g of 60% sodium hydride was added thereto under ice cooling. The reaction solution was stirred at room temperature for 30 minutes, 3.43 g of methyl 6-chloronicotinate was added thereto under ice cooling, and the resulting mixture was stirred at 70° C. overnight. The reaction solution was cooled to room temperature, poured into water and extracted with ethyl acetate. The organic layer was washed with saturated brine. Thereafter, the resultant was dried over anhydrous magnesium sulfate. The solvent was distilled off under reduced pressure, and the obtained residue was purified by silica gel column chromatography (developing solvent: n-hexane/ethyl acetate) to obtain 5.36 g of a target compound. Yield: 90%.

$^1$H-NMR (CDCl$_3$, δ ppm) 3.92 (3H, s), 7.01 (1H, d), 7.26 (2H, d), 7.67 (2H, d), 8.32 (1H, d), 8.80 (1H, s)

Step 2

Synthesis of 6-(4-(trifluoromethyl)phenoxy) nicotinic acid

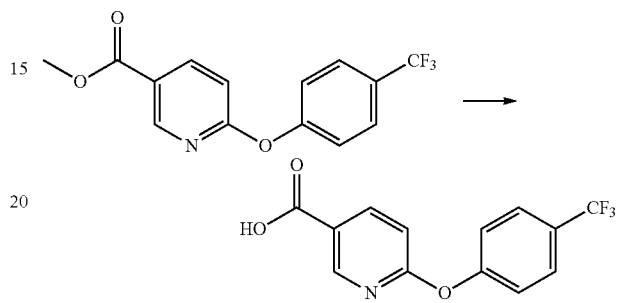

5.36 g of methyl 6-(4-(trifluoromethyl)phenoxy) nicotinate was dissolved in a mixed solvent of 30 ml of methanol and 15 ml of water, 0.87 g of sodium hydroxide was added thereto, and the resulting mixture was stirred at room temperature for 2 hours. The reaction solution was concentrated under reduced pressure, and then poured into dilute hydrochloric acid and extracted with ethyl acetate. The organic layer was washed with saturated brine. Thereafter, the resultant was dried over anhydrous magnesium sulfate. The solvent was distilled off under reduced pressure to obtain 4.59 g of a target compound. Yield: 90%.

$^1$H-NMR (CDCl$_3$, δ ppm) 7.04 (1H, d), 7.30 (2H, d), 7.70 (2H, d), 8.36 (1H, d), 8.85 (1H, s)

Step 3

Synthesis of (4-(4-chlorophenyl)-4-hydroxypiperidin-1-yl) (6-(4-(trifluoromethyl)phenoxy) pyridin-3-yl) methanone

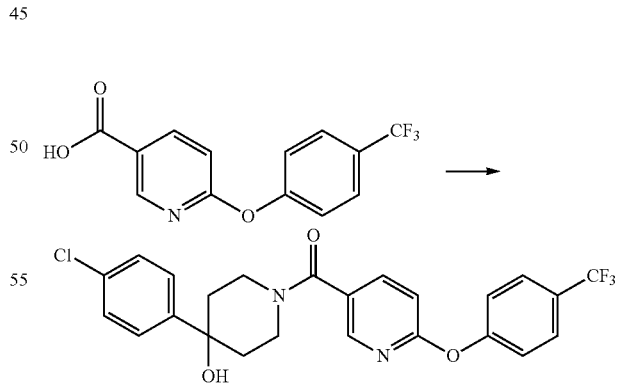

0.3 g of 6-(4-(trifluoromethyl)phenoxy) nicotinic acid was suspended in 15 ml of dichloromethane, to which 0.34 g of 4-(4-chlorophenyl)-4-hydroxypiperidine, 0.19 g of 4-(N,N-dimethylamino) pyridine and 0.3 g of 1-[3-(diethylamino) propyl]-3-ethylcarbodiimide hydrochloride were added, and the resulting mixture was stirred at room temperature overnight. The reaction solution was poured into ice water and extracted with chloroform. The resultant was washed sequentially with water and saturated brine. Thereafter, the resultant was dried over anhydrous magnesium sulfate. The solvent was distilled off under reduced pressure, and the obtained residue was purified by silica gel column chromatography (developing solvent: n-hexane/ethyl acetate) to obtain 0.46 g of a target compound. Yield: 91%

¹H-NMR (CDCl₃, δ ppm) 1.66-2.19 (4H, m), 3.23-3.79 (3H, m), 4.56-4.71 (1H, m), 7.03 (1H, d), 7.25-7.40 (6H, m), 7.67 (2H, d), 7.86 (1H, d), 8.27 (1H, s)

Example 3

Production of 5-(4-(5-methyl-1,2,4-oxadiazol-3-yl) piperidine-1-carbonyl)-6-difluoromethyl-2-(4-(trifluoromethyl)phenyl) nicotinonitrile Step 1

Synthesis of tertiary butyl 4-(N-hydroxyamidine) piperidine-1-carboxylate

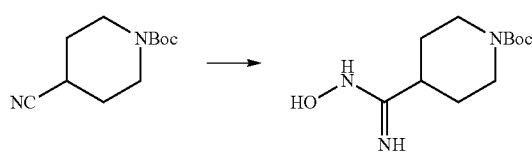 [SMILES: CC(C)(C)OC(=O)N1CCC(C#N)CC1 ; CC(C)(C)OC(=O)N1CCC(C(=N)NO)CC1]

5.0 g of hydroxyamine hydrochloride was dissolved in 24 ml of water, 12.6 g of sodium carbonate was added thereto, and then 24 ml of methanol and 5.0 g of tertiary butyl 4-cyanopiperidine-1-carboxylate were added, followed by heating under reflux for 3.5 hours. Thereafter, the reaction solution was concentrated under reduced pressure and extracted with ethyl acetate. The extract was washed with saturated brine, and the organic layer was dried over anhydrous magnesium sulfate. The solvent was distilled off under reduced pressure to obtain 5.51 g of a target compound. Yield: 95%.

¹H-NMR (CD₃OD, δ ppm) 4.11 (2H, d), 2.71-2.80 (2H, m), 2.19-2.28 (1H, m), 1.72 (2H, d), 1.53-1.62 (2H, m), 1.45 (9H, s)

Step 2

Synthesis of tertiary butyl 4-(5-methyl-1,2,4-oxadiazol-3-yl) piperidine-1-carboxylate

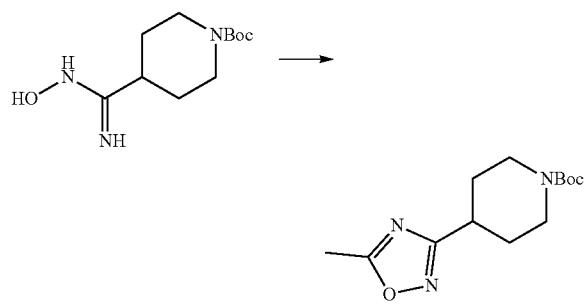

5.0 g of tertiary butyl 4-(N-hydroxyamidine) piperidine-1-carboxylate was dissolved in 70 ml of N,N-dimethylformamide 2.9 ml of acetic anhydride was added thereto, and the resulting mixture was stirred at room temperature for 1 hour and then at 100° C. for 2.5 hours. The reaction solution was cooled to room temperature and poured into water. The resultant was extracted with ethyl acetate, the extract was washed with saturated brine, and the organic layer was dried over anhydrous magnesium sulfate. The solvent was distilled off under reduced pressure, and the obtained residue was purified by silica gel column chromatography (developing solvent: n-hexane/ethyl acetate=1/1) to obtain 4.08 g of a target compound. Yield: 74%.

¹H-NMR (CDCl₃, δ ppm) 4.10-4.17 (2H, m), 2.87-2.97 (3H, m), 2.58 (3H, s), 1.96 (2H, d), 1.70-1.80 (2H, m), 1.47 (9H, s)

Step 3

Synthesis of 5-methyl-3-(piperidin-4-yl)-1,2,4-oxadiazole hydrochloride

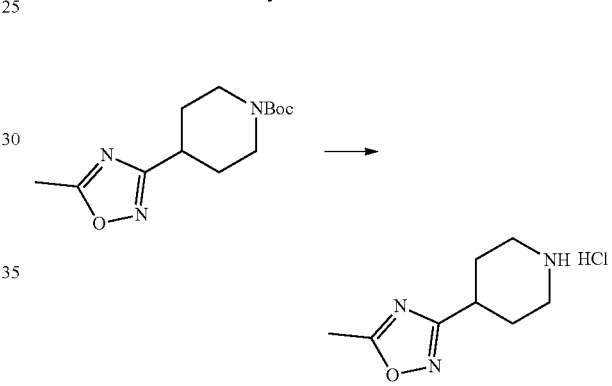

4.08 g of tertiary butyl 4-(5-methyl-1,2,4-oxadiazol-3-yl) piperidine-1-carboxylate was dissolved in 38 ml of 1,4-dioxane. 19 ml of a 4 M hydrochloric acid 1,4-dioxane solution was added thereto, and the resulting mixture was stirred at room temperature overnight. Thereafter, the reaction solution was concentrated under reduced pressure to obtain 2.15 g of a target compound. Yield: 84%.

¹H-NMR (CDCl₃, δ ppm) 3.41-3.46 (2H, m), 3.11-3.17 (3H, m), 2.58 (3H, s), 2.20-2.40 (4H, m)

Step 4

Synthesis of 5-(4-(5-methyl-1,2,4-oxadiazol-3-yl) piperidine-1-carbonyl)-6-difluoromethyl-2-(4-(trifluoromethyl)phenyl) nicotinonitrile

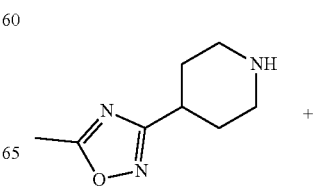

-continued

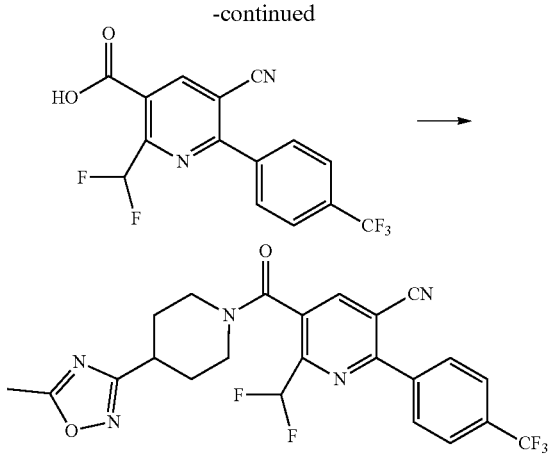

5-cyano-2-(difluoromethyl)-6-(4-(trifluoromethyl)phenyl) nicotinic acid was dissolved in 11 ml of dichloromethane. 0.02 g of N,N-dimethylformamide and 0.29 ml of oxalyl chloride were added thereto under ice cooling. Thereafter, the resulting mixture was stirred at room temperature for 30 minutes. The reaction solution was concentrated under reduced pressure, and the obtained residue was dissolved in 11 ml of dichloromethane 0.41 g of 5-methyl-3-(piperidin-4-yl)-1,2,4-oxadiazole, 0.03 g of N,N-dimethyl-4-aminopyridine and 0.94 ml of triethylamine were added thereto under ice cooling, and the resulting mixture was stirred at room temperature for 1.5 hours. Thereafter, the reaction solution was concentrated under reduced pressure, and the obtained residue was purified by silica gel column chromatography (developing solvent: n-hexane/ethyl acetate=1/1) to obtain 0.86 g of a target compound. Yield: 78%.

$^1$H-NMR (CDCl$_3$, δ ppm) 8.14 (3H, m), 7.84 (2H, d), 6.84 (1H, t), 4.50-4.70 (1H, m), 3.55 (1H, d), 3.10-3.32 (3H, m), 2.60 (3H, s), 2.19-2.23 (1H, m), 1.81-2.05 (3H, m)

Some of the compounds of the present invention prepared by the same method as in the above examples are shown in Tables 1 to 4. Table 1 shows substituents of the compound represented by formula (I-1) Table 2 shows substituents of the compound represented by formula (I-2). Table 11 shows substituents of the compound represented by formula (I-3) Table 4 shows substituents of the compound represented by formula (I-4). In the tables, properties, melting point (imp.) or refractive index (n$_D$) are shown together as physical properties of each compound.

Ar, X$^1$, n, X$^{2a}$, X$^{2b}$, R$^1$ to R$^9$ in the formula are the same as defined above. A' represents a nitrogen atom, CH, or C—X$^{2a}$ (X$^{2c}$ is the same as defined above). In the tables, Me represents a methyl group, Et represents an ethyl group, $^n$Pr represents a normal propyl group, $^i$Pr represents an isopropyl group, $^c$Pr represents a cyclopropyl group, and $^n$Bu represents a normal butyl group, respectively.

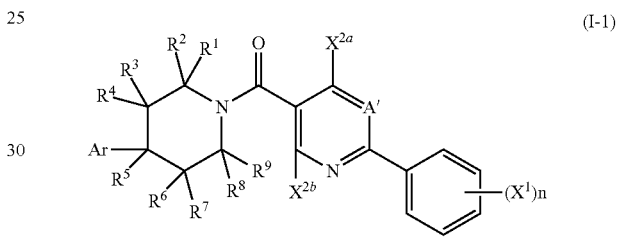

(I-1)

TABLE 1

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-1 | 4-Cl-phenyl | H | H | H | H | OH | H | H | H | H | H | CHF₂ | C—CN | 4-CF₃ | m.p.: 200° C. up |
| 1-2 | phenyl | H | H | H | H | CN | H | H | H | H | H | CHF₂ | C—CN | 4-CF₃ | viscous oil |
| 1-3 | 2-hydroxy-1H-benzol[d]imidazol-1-yl | H | H | H | H | H | H | H | H | H | H | CHF₂ | C—CN | 4-CF₃ | m.p.: 200° C. up |
| 1-4 | 3-Cl-pyridin-2-yl | H | H | H | H | OH | H | H | H | H | H | CHF₂ | C—CN | 4-CF₃ | m.p.: 200° C. up |
| 1-5 | 4-Cl-phenyl | H | H | H | H | OH | H | H | H | H | H | CF₃ | C—CN | 4-CF₃ | viscous oil |
| 1-6 | 4-CF₃-phenyl | H | H | H | H | OH | H | H | H | H | H | CHF₂ | C—CN | 4-CF₃ | viscous oil |
| 1-7 | 4-CF₃-phenyl | H | H | H | H | OMe | H | H | H | H | H | CHF₂ | C—CN | 4-CF₃ | viscous oil |
| 1-8 | 4-CF₃-phenyl | H | H | H | H | H | H | H | H | H | H | CHF₂ | C—CN | 4-CF₃ | viscous oil |
| 1-9 | 3-CF₃-4-Cl-phenyl | H | H | H | H | OH | H | H | H | H | H | CHF₂ | C—CN | 4-CF₃ | viscous oil |
| 1-10 | 4-ⁿBu-phenyl | H | H | H | H | OH | H | H | H | H | H | CHF₂ | C—CN | 4-CF₃ | viscous oil |
| 1-11 | 4-Cl-phenyl | H | H | H | H | OH | H | H | H | H | H | H | CH | 4-CF₃ | m.p.: 178-180° C. |
| 1-12 | 4-OCF₃-phenyl | H | H | H | H | OH | H | H | H | H | H | CHF₂ | C—CN | 4-CF₃ | viscous oil |
| 1-13 | 4-OCF₃-phenyl | H | H | H | H | OH | Et | H | H | H | H | CHF₂ | C—CN | 4-CF₃ | amorphous |
| 1-14 | 3-Cl-phenyl | H | H | H | H | OH | H | H | H | H | H | CHF₂ | C—CN | 4-CF₃ | m.p.: 192-194° C. |
| 1-15 | 2-Cl-phenyl | H | H | H | H | OH | H | H | H | H | H | CHF₂ | C—CN | 4-CF₃ | m.p.: 178-180° C. |
| 1-16 | 4-Cl-phenyl | H | H | H | H | OH | H | H | H | H | H | Me | C—CN | 4-CF₃ | m.p.: 208-210° C. |
| 1-17 | 4-Br-phenyl | H | H | H | H | OH | H | H | H | H | H | CHF₂ | C—CN | 4-CF₃ | viscous oil |
| 1-18 | 4-Cl-phenyl | H | H | H | H | H | H | H | H | H | H | CHF₂ | C—CN | 4-CF₃ | viscous oil |
| 1-19 | pyridin-2-yl | H | H | H | H | OH | H | H | H | H | H | CHF₂ | C—CN | 4-CF₃ | viscous oil |
| 1-20 | 3-CF₃-phenyl | H | H | H | H | H | H | H | H | H | H | CHF₂ | C—CN | 4-CF₃ | viscous oil |
| 1-21 | phenyl | H | H | H | H | OH | H | H | H | H | H | CHF₂ | C—CN | 4-CF₃ | m.p.: 200° C. up |
| 1-22 | phenyl | CH₂(CH₂)₂C | H | H | H | OH | H | H | H | H | H | CHF₂ | C—CN | 4-CF₃ | viscous oil |
| 1-23 | 4-Br—1H-pyrazol-1-yl | H | H | H | H | H | H | H | H | H | H | CHF₂ | C—CN | 4-CF₃ | m.p.: 185-188° C. |
| 1-24 | 3-CF₃-1H-pyrazol-1-yl | H | H | H | H | H | H | H | H | H | H | CHF₂ | C—CN | 4-CF₃ | amorphous |
| 1-25 | 4-OCF₃-phenyl | Et | H | H | H | OH | H | H | H | H | H | CHF₂ | C—CN | 4-CF₃ | viscous oil |
| 1-26 | 4-Cl-phenyl | H | H | H | H | OH | H | H | H | H | H | H | N | 4-CF₃ | viscous oil |
| 1-27 | 4-Cl-phenyl | H | H | H | H | OH | H | H | H | H | CF₃ | H | CH | 4-CF₃ | viscous oil |
| 1-28 | 2-CF₃-phenyl | H | H | H | H | OH | H | H | H | H | CF₃ | CHF₂ | C—CN | 4-CF₃ | m.p.: 174-177° C. |
| 1-29 | 2,4-Cl₂-phenyl | H | H | H | H | OH | H | H | H | H | H | CHF₂ | C—CN | 4-CF₃ | viscous oil |
| 1-30 | 4-Cl-phenyl | H | H | H | H | CN | H | H | H | H | H | CHF₂ | C—CN | 4-CF₃ | viscous oil |
| 1-31 | pyridin-2-yl | H | H | H | H | OH | H | H | H | H | H | Me | C—CN | 4-CF₃ | viscous oil |
| 1-32 | 4-Cl-phenyl | H | H | H | H | OH | H | H | H | H | H | CF₃ | CH | 4-CF₃ | m.p.: 200° C. up |
| 1-33 | 2,3-Cl₂-phenyl | H | H | H | H | OH | H | H | H | H | H | CHF₂ | C—CN | 4-CF₃ | viscous oil |
| 1-34 | phenyl | H | H | H | H | C(=OMe) | H | H | H | H | H | Me | CH | 4-CF₃ | viscous oil |
| 1-35 | phenyl | H | H | H | H | H | H | H | H | H | H | Me | CH | 4-CF₃ | m.p.: 200° C. up |
| 1-36 | phenyl | H | H | H | H | CN | H | H | H | H | H | H | C—Cl | 4-CF₃ | m.p.: 200° C. up |
| 1-37 | 4-Cl-phenyl | H | H | H | H | OH | H | H | H | H | H | H | C-(4-CF₃-Phenyl) | 4-CF₃ | m.p.: 150-155° C. |
| 1-38 | 4-Cl-phenyl | H | H | H | H | OH | H | H | H | H | H | CHF₂ | C—CN | 2-CF₃ | viscous oil |
| 1-39 | 4-Cl-phenyl | H | H | H | H | OH | H | H | H | H | H | CHF₂ | C—CN | 3-CF₃ | viscous oil |
| 1-40 | 4-Cl-phenyl | H | H | H | H | OH | H | H | H | H | H | CHF₂ | C—CN | 4-CF₃ | viscous oil |
| 1-41 | 4-Cl-phenyl | H | H | H | H | OH | H | H | H | H | H | CHF₂ | C—CN | 4-CF₃ | viscous oil |
| 1-42 | 4-Cl-phenyl | H | H | H | H | OH | H | H | H | H | H | CHF₂ | C—CN | 4-CF₃ | viscous oil |
| 1-43 | 4-F-phenyl | H | H | H | H | OH | H | H | H | H | H | CHF₂ | C—CN | 4-CF₃ | m.p.: 200° C. up |
| 1-44 | 2-F-phenyl | H | H | H | H | OH | H | H | H | H | H | CHF₂ | C—CN | 4-CF₃ | m.p.: 200° C. up |
| 1-45 | 2-Me-phenyl | H | H | H | H | OH | H | H | H | H | H | CHF₂ | C—CN | 4-CF₃ | viscous oil |

TABLE 1-continued

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-46 | 2,5-Cl₂-phenyl | H | H | H | H | OH | H | H | H | H | H | CHF₂ | C—CN | 4-CF₃ | viscous oil |
| 1-47 | thiazol-2-yl | H | H | H | H | OH | H | H | H | H | H | CHF₂ | C—CN | 4-CF₃ | viscous oil |
| 1-48 | 4-F-phenyl | H | H | H | H | OH | H | H | H | H | H | Me | C—CN | 4-CF₃ | m.p.: 200° C. up |
| 1-49 | thiazol-2-yl | H | H | H | H | OH | H | H | H | H | H | Me | C—CN | 4-CF₃ | viscous oil |
| 1-50 | phenyl | H | H | H | H | C(=O)OMe | H | H | H | H | H | CHF₂ | C—CN | 4-CF₃ | viscous oil |
| 1-51 | phenyl | H | H | H | H | Phenyl | H | H | H | H | H | CHF₂ | C—CN | 4-CF₃ | viscous oil |
| 1-52 | 3-CF₃-pyridin-2-yl | H | H | H | H | OH | H | H | H | H | H | CHF₂ | C—CN | 4-CF₃ | m.p.: 92-94° C. |
| 1-53 | 1H-pyrazol-1-yl | H | H | H | H | H | H | H | H | H | H | CHF₂ | C—CN | 4-CF₃ | viscous oil |
| 1-54 | 1H-1,2,4-triazol-1-yl | H | H | H | H | H | H | H | H | H | H | CHF₂ | C—CN | 4-CF₃ | viscous oil |
| 1-55 | 2-CF₃-phenyl | H | H | H | H | OH | H | H | H | H | H | CHF₂ | C—CN | 4-CF₃ | viscous oil |
| 1-56 | 4-Br—1H-pyrazol-1-yl | H | H | H | H | H | H | H | H | H | H | CF₃ | C—CN | 4-CF₃ | m.p.: 206-209° C. |
| 1-57 | 4-Cl-phenyl | H | H | H | H | OC(=O)Me | H | H | H | H | H | Me | C—CN | 4-CF₃ | viscous oil |
| 1-58 | 4-Cl-phenyl | H | H | H | H | OH | H | H | H | H | H | ⁱPr | C—CN | 4-CF₃ | m.p.: 203-205° C. |
| 1-59 | 4-Cl-phenyl | H | H | H | H | OH | H | H | H | H | H | Me | N | 4-Cl | m.p.: 95-98° C. |
| 1-60 | 4-Cl-phenyl | H | H | H | H | OMe | H | H | H | H | H | Me | C—CN | 4-CF₃ | viscous oil |
| 1-61 | 4-Cl-phenyl | H | H | H | H | OEt | H | H | H | H | H | Me | C—CN | 4-CF₃ | viscous oil |
| 1-62 | 4-Cl-phenyl | H | H | H | H | F | H | H | H | H | H | CHF₂ | C—CN | 4-CF₃ | viscous oil |
| 1-63 | 4-Cl-phenyl | H | H | H | H | F | H | H | H | H | H | Me | C—CN | 4-CF₃ | viscous oil |
| 1-64 | 4-Cl-phenyl | H | H | H | H | H | H | H | H | H | H | Me | C—CN | 4-CF₃ | viscous oil |
| 1-65 | 4-Cl-phenyl | H | H | H | H | OH | H | H | H | H | H | Et | C—CN | 4-CF₃ | viscous oil |
| 1-66 | 4-Cl-phenyl | H | H | H | H | OH | H | H | H | H | H | OMe | N | 4-CF₃ | m.p.: 157-160° C. |
| 1-67 | 4-Me-thiazol-2-yl | H | H | H | H | OH | H | H | H | H | H | CHF₂ | C—CN | 4-CF₃ | viscous oil |
| 1-68 | 4,5-dihydrooxazol-2-yl | H | H | H | H | OH | H | H | H | H | H | CHF₂ | C—CN | 4-CF₃ | m.p.: 168-170° C. |
| 1-69 | 2H-1,2,3-triazol-2-yl | H | H | H | H | H | H | H | H | H | H | CHF₂ | C—CN | 4-CF₃ | m.p.: 69-71° C. |
| 1-70 | 1,3,4-oxadiazol-2-yl | H | H | H | H | H | H | H | H | H | H | CHF₂ | C—CN | 4-CF₃ | viscous oil |
| 1-71 | pyridin-4-yl | H | H | H | H | CN | H | H | H | H | H | Me | C—CN | 4-CF₃ | m.p.: 80-82° C. |
| 1-72 | 4-F-phenyl | H | H | H | H | CN | H | H | H | H | H | Me | C—CN | 4-CF₃ | amorphous |
| 1-73 | 5-Me-1,2,4-oxadiazol-3-yl | H | H | H | H | H | H | H | H | H | H | Me | C—CN | 4-CF₃ | m.p.: 78-80° C. |
| 1-74 | 4-Cl-phenyl | H | H | H | H | OC(=O)ⁿPr | H | H | H | H | H | CHF₂ | C—CN | 4-CF₃ | viscous oil |
| 1-75 | 4-Cl-phenyl | H | H | H | H | OH | H | H | H | H | H | Phenyl | C—CN | 4-CF₃ | m.p.: 173-176° C. |
| 1-76 | 5-CF₃-1,2,4-oxadiazol-3-yl | H | H | H | H | H | H | H | H | H | H | CHF₂ | C—CN | 4-CF₃ | m.p.: 70-72° C. |
| 1-77 | 3-Me-1,2,4-oxadiazol-5-yl | H | H | H | H | H | H | H | H | H | H | CHF₂ | C—CN | 4-CF₃ | m.p.: 79-81° C. |
| 1-78 | 4-Cl-phenyl | H | H | H | H | H | H | H | H | H | H | CHF₂ | C—CN | 4-CF₃ | viscous oil |
| 1-79 | 4-Cl-phenyl | H | H | H | H | OH | H | H | H | H | H | Me | C—CN | 4-Cl | viscous oil |
| 1-80 | 4-Cl-phenyl | H | H | H | H | OH | H | H | H | H | H | OMe | C—CN | — | viscous oil |
| 1-81 | 4-Cl-phenyl | H | H | H | H | OH | H | H | H | H | H | OMe | C—CN | — | viscous oil |
| 1-82 | 4-Cl-phenyl | H | H | H | H | OH | H | H | H | H | H | CHF₂ | C—CN | 4-CF₃ | amorphous |
| 1-83 | pyridin-3-yl | H | H | H | H | OH | H | H | H | H | H | CHF₂ | C—CN | 4-OCF₃ | amorphous |
| 1-84 | 4-Cl-phenyl | H | H | H | H | OH | H | H | H | H | H | CHF₂ | C—CN | 4-F | m.p.: 176-179° C. |
| 1-85 | 4-Cl-phenyl | H | H | H | H | OH | H | H | H | H | H | OCH₂CH=CH₂ | C—CN | 4-Cl | m.p.: 165-167° C. |
| 1-86 | 4-Cl-phenyl | H | H | H | H | OH | H | H | H | H | H | CHF₂ | C—CN | 4-CF₃ | m.p.: 210-212° C. |
| 1-87 | 2,6-Cl₂-phenyl | H | H | H | H | H | H | H | H | H | H | CHF₂ | C—CN | 4-CF₃ | m.p.: 120-122° C. |
| 1-88 | 1H-indol-3-yl | H | H | H | H | OH | H | H | H | H | H | CHF₂ | C—CN | 4-CF₃ | m.p.: 78-90° C. |
| 1-89 | thiophen-2-yl | H | H | H | H | OH | H | H | H | H | H | CHF₂ | C—CN | 4-CF₃ | m.p.: 94-96° C. |
| 1-90 | 2,6-F₂-phenyl | H | H | H | H | OH | H | H | H | H | H | CHF₂ | C—CN | 4-CF₃ | |

TABLE 1-continued

| Compound No. | Ar | $R^1$ | $R^2$ | $R^3$ | $R^4$ | $R^5$ | $R^6$ | $R^7$ | $R^8$ | $R^9$ | $X^{2a}$ | $X^{2b}$ | A' | $(X^1)n$ | Physical Properties |
|---|---|---|---|---|---|---|---|---|---|---|---|---|---|---|---|
| 1-91 | 6-F-benzo[d]isoxazol-3-yl | H | H | H | H | H | H | H | H | H | H | $CHF_2$ | C—CN | 4-$CF_3$ | m.p.: 98-100° C. |
| 1-92 | pyridin-2-yl | H | H | H | H | H | H | H | H | H | H | $CHF_2$ | C—CN | 4-$CF_3$ | m.p.: 82-84° C. |
| 1-93 | benzo[d]thiazol-2-yl | H | H | H | H | H | H | H | H | H | H | $CHF_2$ | C—CN | 4-$CF_3$ | m.p.: 87-89° C. |
| 1-94 | 2,2-$F_2$-benzo[d][1,3]dioxol-4-yl | H | H | H | H | H | H | H | H | H | H | $CHF_2$ | C—CN | 4-$CF_3$ | m.p.: 212-214° C. |
| 1-95 | 4-Cl-phenyl | H | H | H | H | OH | H | H | H | H | H | $CHF_2$ | C—CN | 4-Me | m.p.: 220° C. up |
| 1-96 | 4-Cl-phenyl | H | H | H | H | OH | H | H | H | H | H | $CHF_2$ | C—CN | 4-OMe | viscous oil |
| 1-97 | 4-Cl-phenyl | H | H | H | H | OH | H | H | H | H | H | $CHF_2$ | C—CN | 4-CN | m.p.: 220° C. up |
| 1-98 | 4-Cl-phenyl | H | H | H | H | OH | H | H | H | H | H | $CHF_2$ | C—CN | 2-F,4-Cl | viscous oil |
| 1-99 | 4-Cl-phenyl | H | H | H | H | OH | H | H | H | H | H | $CHF_2$ | C—CN | 3,4-$Cl_2$ | viscous oil |
| 1-100 | 4-Cl-phenyl | H | H | H | H | OC(=O)$^i$Pr | H | H | H | H | H | OH | C—CN | 4-Cl | amorphous |
| 1-101 | 4-Cl-phenyl | H | H | H | H | OH | H | H | H | H | H | Me | C—CN | 4-$CF_3$ | viscous oil |
| 1-102 | 4-Cl-phenyl | H | H | H | H | OH | H | H | H | H | H | Me | C—CN | — | m.p.: 165-169° C. |
| 1-103 | 4-Cl-phenyl | H | H | H | H | OH | H | H | H | H | H | OMe | C—Me | 4-$CF_3$ | m.p.: 142-146° C. |
| 1-104 | 4-Cl-phenyl | H | H | H | H | OH | H | H | H | H | OMe | Me | CH | 4-Cl | viscous oil |
| 1-105 | 4-Cl-phenyl | H | H | H | H | OH | H | H | H | H | H | $^i$Pr | C—CN | 4-$CF_3$ | viscous oil |
| 1-106 | 4-Br-phenyl | H | H | H | H | OMe | H | H | H | H | H | Me | C—CN | 4-$CF_3$ | amorphous |
| 1-107 | 4-$CF_3$-phenyl | H | H | H | H | OMe | H | H | H | H | H | Me | C—CN | 4-$CF_3$ | amorphous |
| 1-108 | 4-Cl-phenyl | H | H | H | H | OH | H | H | H | H | OMe | H | CH | 4-$CF_3$ | viscous oil |
| 1-109 | 2,2-$F_2$-benzo[d][1,3]dioxol-4-yl | H | H | H | H | OH | H | H | H | H | H | $CF_3$ | C—CN | 4-$CF_3$ | m.p.: 138-142° C. |
| 1-110 | 4-phenyl-thiazol-2-yl | H | H | H | H | H | H | H | H | H | H | $CHF_2$ | C—CN | 4-$CF_3$ | m.p.: 92-95° C. |
| 1-111 | 4-Me-phenyl | H | H | H | H | H | H | H | H | H | H | Me | C—CN | 4-$CF_3$ | m.p.: 99-102° C. |
| 1-112 | 4-(C(=O)OEt)thiazol-2-yl | H | H | H | H | H | H | H | H | H | H | Me | C—CN | 4-Cl | m.p.: 78-80° C. |
| 1-113 | 4-phenyl-1H-pyrazol-1-yl | H | H | H | H | H | H | H | H | H | H | Me | C—CN | 4-$CF_3$ | m.p.: 78-80° C. |
| 1-114 | 4-F-phenyl | H | H | H | H | OMe | H | H | H | H | H | Me | C—CN | 4-$CF_3$ | viscous oil |
| 1-115 | 1-Me-1H-1,2,4-triazol-3-yl | H | H | H | H | H | H | H | H | H | H | $CHF_2$ | C—CN | 4-$CF_3$ | m.p.: 64-68° C. |
| 1-116 | 2'-F-phenyl | H | H | H | H | OH | H | H | H | H | H | Me | C—CN | 4-OCF_3 | m.p.: 166-169° C. |
| 1-117 | 4-Cl-phenyl | H | H | H | H | OH | H | H | H | H | H | Me | C—CN | 4-OCF_3 | m.p.: 167-170° C. |
| 1-118 | 4-Cl-phenyl | H | H | H | H | OMe | H | H | H | H | H | Me | C—CN | 4-OCF_3 | m.p.: 64-66° C. |
| 1-119 | 4-Cl-phenyl | H | H | H | H | OH | H | H | H | H | H | Me | C—Me | 4-$CF_3$ | m.p.: 100-105° C. |
| 1-120 | 4-Cl-phenyl | H | H | H | H | OH | H | H | H | H | H | Me | C—Me | 4-$CF_3$ | m.p.: 220° C. up |
| 1-121 | 4-F-phenyl | H | H | H | H | OH | C(=O)NHMe | H | H | H | H | Me | C—C(=O)Me | 4-$CF_3$ | viscous oil |
| 1-122 | 4-F-phenyl | H | H | H | H | OH | C(=O)NMe_2 | H | H | H | H | Et | C—CN | 4-$CF_3$ | viscous oil |
| 1-123 | 4-F-phenyl | H | H | H | H | OH | H | H | H | H | H | $CHF_2$ | C—CN | 4-$CF_3$ | viscous oil |
| 1-124 | phenyl | H | H | H | H | OH | H | H | H | H | H | $CHF_2$ | C—CN | 4-$CF_3$ | viscous oil |
| 1-125 | phenyl | H | H | H | H | OMe | H | H | H | H | H | $CHF_2$ | C—CN | 4-$CF_3$ | amorphous |
| 1-126 | 2-OCF_3-phenyl | H | H | H | H | OMe | H | H | H | H | H | Me | C—CN | 4-$CF_3$ | m.p.: 95-97° C. |
| 1-127 | 2-OCF_3-phenyl | H | H | H | H | OMe | H | H | H | H | H | Me | C—CN | 4-$CF_3$ | m.p.: 76-78° C. |
| 1-128 | 2-OCF_3-phenyl | H | H | H | H | H | H | H | H | H | H | Me | C—CN | 4-$CF_3$ | m.p.: 80-83° C. |
| 1-129 | pyridin-2-yl | H | H | H | H | OMe | H | H | H | H | H | Me | C—CN | 4-$CF_3$ | m.p.: 58-60° C. |
| 1-130 | pyridin-2-yl | H | H | H | H | OMe | H | H | H | H | H | Me | C—CN | 4-OCF_3 | m.p.: 58-60° C. |
| 1-131 | 5-F-pyridin-2-yl | H | H | H | H | OH | H | H | H | H | H | Me | C—CN | 4-$CF_3$ | m.p.: 52-54° C. |
| 1-132 | 4-Cl-phenyl | H | H | H | H | OH | H | H | H | H | H | $CHF_2$ | C—CN | 2-F, 4-$CF_3$ | amorphous |
| 1-133 | 4-Cl-phenyl | H | H | H | H | OH | H | H | H | H | H | $CHF_2$ | C—CN | 2-Cl, 4-$CF_3$ | viscous oil |
| 1-134 | 4-Cl-phenyl | H | H | H | H | OH | H | H | H | H | H | $CHF_2$ | C—CN | 2-OMe, 4-$CF_3$ | viscous oil |
| 1-135 | 4-Cl-phenyl | H | H | H | H | OH | H | H | H | H | H | $CHF_2$ | C—CN | 2,4-$(CF_3)_2$ | m.p.: 105-110° C. |

TABLE 1-continued

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-136 | 4-Cl-phenyl | H | H | H | H | OH | H | H | H | H | H | CHF₂ | C—CN | 3,5-(CF₃)₂ | viscous oil |
| 1-137 | 4-Cl-phenyl | H | H | H | H | OH | H | H | H | H | H | H | C—CN | 4-CF₃ | m.p.: 99-102° C. |
| 1-138 | 4-F-phenyl | H | H | H | H | OH | H | H | H | H | H | Me | C—CN | 4-OCF₃ | amorphous |
| 1-139 | 4-Me-phenyl | H | H | H | H | OH | H | H | H | H | H | Me | C—CN | 4-CF₃ | m.p.: 89-92° C. |
| 1-140 | 4-OMe-phenyl | H | H | H | H | OH | H | H | H | H | H | CHF₂ | C—CN | 4-CF₃ | m.p.: 90-93° C. |
| 1-141 | 4-Me-phenyl | H | H | H | H | OMe | H | H | H | H | H | Me | C—CN | 4-CF₃ | viscous oil |
| 1-142 | 4-Me-phenyl | H | H | H | H | OMe | H | H | H | H | H | Me | C—CN | 4-OCF₃ | viscous oil |
| 1-143 | 4-Me-phenyl | H | H | H | H | H | H | H | H | H | H | Me | C—CN | 4-CF₃ | viscous oil |
| 1-144 | 4-Me-phenyl | H | H | H | H | H | H | H | H | H | H | Me | C—CN | 4-OCF₃ | amorphous |
| 1-145 | 5-F-pyridin-2-yl | H | H | H | H | OMe | H | H | H | H | H | CHF₂ | C—CN | 4-CF₃ | m.p.: 81-84° C. |
| 1-146 | 5-F-pyridin-2-yl | H | H | H | H | OMe | H | H | H | H | H | Me | C—CN | 4-CF₃ | m.p.: 83-85° C. |
| 1-147 | 4-CF₃-thiazol-2-yl | H | H | H | H | H | H | H | H | H | H | CHF₂ | C—CN | 4-CF₃ | m.p.: 79-81° C. |
| 1-148 | 5-F-pyridin-2-yl | H | H | H | H | OH | H | H | H | H | H | CHF₂ | C—CN | 4-CF₃ | m.p.: 150-151° C. |
| 1-149 | 3,5-F₂-phenyl | H | H | H | H | OH | H | H | H | H | H | CHF₂ | C—CN | 4-CF₃ | m.p.: 205-206° C. |
| 1-150 | 3,5-F₂-phenyl | H | H | H | H | OH | H | H | H | H | H | Me | C—CN | 4-OCF₃ | m.p.: 229-230° C. |
| 1-151 | 2,4-F₂-phenyl | H | H | H | H | OH | H | H | H | H | H | CHF₂ | C—CN | 4-CF₃ | m.p.: 219-220° C. |
| 1-152 | 2,4-F₂-phenyl | H | H | H | H | OH | H | H | H | H | H | Me | C—CN | 4-OCF₃ | m.p.: 234-235° C. |
| 1-153 | 3,4-F₂-phenyl | H | H | H | H | OH | H | H | H | H | H | CHF₂ | C—CN | 4-CF₃ | m.p.: 240° C. up |
| 1-154 | 3,4-F₂-phenyl | H | H | H | H | OH | H | H | H | H | H | Me | C—CN | 4-CF₃ | m.p.: 240° C. up |
| 1-155 | 3,5-F₂-phenyl | H | H | H | H | OH | H | H | H | H | H | CHF₂ | C—CN | 4-CF₃ | m.p.: 88-90° C. |
| 1-156 | 5-F-pyridin-2-yl | H | H | H | H | OMe | H | H | H | H | H | CHF₂ | C—CN | 4-CF₃ | m.p.: 78-80° C. |
| 1-157 | 4-Cl-phenyl | H | H | H | H | OH | H | H | H | H | H | CHF₂ | C—CN | 4-CF₃ | viscous oil |
| 1-158 | 4-Cl-phenyl | H | H | H | H | OH | H | H | H | H | H | CHF₂ | C—CN | 3-Cl, 4-CF₃ | m.p.: 110-113° C. |
| 1-159 | 4-Me-1H-pyrazol-1-yl | H | H | H | H | H | H | H | H | H | H | CHF₂ | C—CN | 3-F, 4-CF₃ | m.p.: 72-74° C. |
| 1-160 | 2,4-F₂-phenyl | H | H | H | H | OMe | H | H | H | H | H | CHF₂ | C—CN | 4-CF₃ | m.p.: 78-80° C. |
| 1-161 | 5-Me-1,2,4-oxadiazol-3-yl | H | H | H | H | H | H | H | H | H | H | Me | C—CN | 4-CF₃ | m.p.: 58-60° C. |
| 1-162 | 5-Me-1,2,4-oxadiazol-3-yl | H | H | H | H | H | H | H | H | H | H | CHF₂ | C—CN | 4-OCF₃ | m.p.: 58-60° C. |
| 1-163 | 5-Me-1,2,4-oxadiazol-3-yl | H | H | H | H | H | H | H | H | H | H | Me | C—CN | 4-OCF₃ | m.p.: 58-60° C. |
| 1-164 | 1,5-Me₂—1H-pyrazol-3-yl | H | H | H | H | H | H | H | H | H | H | CHF₂ | C—CN | 4-CF₃ | viscous oil |
| 1-165 | 1,3-Me₂—1H-pyrazol-3-yl | H | H | H | H | H | H | H | H | H | H | CHF₂ | C—CN | 4-CF₃ | viscous oil |
| 1-166 | 3,4-F₂-phenyl | H | H | H | H | OMe | H | H | H | H | H | Me | C—CN | 4-CF₃ | m.p.: 78-80° C. |
| 1-167 | 4-OMe-phenyl | H | H | H | H | OMe | H | H | H | H | H | CHF₂ | C—CN | 4-CF₃ | m.p.: 80-82° C. |
| 1-168 | 4-CN-phenyl | H | H | H | H | OH | H | H | H | H | H | CHF₂ | C—CN | 4-CF₃ | m.p.: 240° C. up |
| 1-169 | 1-Me-1H-pyrazol-4-yl | H | H | H | H | H | H | H | H | H | H | CHF₂ | C—CN | 4-CF₃ | viscous oil |
| 1-170 | 1-Me-1H-pyrazol-3-yl | H | H | H | H | H | H | H | H | H | H | CHF₂ | C—CN | 4-CF₃ | m.p.: 78-80° C. |
| 1-171 | 1-Me-1H-pyrazol-5-yl | H | H | H | H | H | H | H | H | H | H | CHF₂ | C—CN | 4-CF₃ | viscous oil |
| 1-172 | 5-Me-1,2,4-oxadiazol-3-yl | H | H | H | H | H | H | H | H | H | H | Et | C—CN | 4-CF₃ | m.p.: 78-81° C. |
| 1-173 | 5-Me-1,2,4-oxadiazol-3-yl | H | H | H | H | H | H | H | H | H | H | CHF₂ | C—CN | 4-CN | m.p.: 78-80° C. |
| 1-174 | 4-CN-phenyl | H | H | H | H | OMe | H | H | H | H | H | CHF₂ | C—CN | 4-CF₃ | m.p.: 113-115° C. |
| 1-175 | 5-Et-1,2,4-oxadiazol-3-yl | H | H | H | H | H | H | H | H | H | H | CHF₂ | C—CN | 4-CF₃ | m.p.: 68-70° C. |
| 1-176 | 3-Me—1H-1,2,4-triazol-1-yl | H | H | H | H | H | H | H | H | H | H | CHF₂ | C—CN | 4-CF₃ | m.p.: 183-194° C. |
| 1-177 | 4H-1,2,4-triazol-4-yl | H | H | H | H | H | H | H | H | H | H | CHF₂ | C—CN | 4-CF₃ | viscous oil |
| 1-178 | 3,5-Me₂-isoxazol-4-yl | H | H | H | H | H | H | H | H | H | H | CHF₂ | C—CN | 4-CF₃ | amorphous |
| 1-179 | 1,5-Me₂-4-Cl—1H-pyrazol-3-yl | H | H | H | H | H | H | H | H | H | H | CHF₂ | C—CN | 4-CF₃ | viscous oil |
| 1-180 | 1,3-Me₂-4-Cl—1H-pyrazol-5-yl | H | H | H | H | H | H | H | H | H | H | CHF₂ | C—CN | 4-CF₃ | viscous oil |

TABLE 1-continued

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-181 | furan-3-yl | H | H | H | H | H | H | H | H | H | H | CHF₂ | C—CN | 4-CF₃ | viscous oil |
| 1-182 | pyridin-3-yl | H | H | H | H | H | H | H | H | H | H | CHF₂ | C—CN | 4-CF₃ | viscous oil |
| 1-183 | 6-F-pyridin-3-yl | H | H | H | H | H | H | H | H | H | H | CHF₂ | C—CN | 4-CF₃ | viscous oil |
| 1-184 | 6-F-pyridin-4-yl | H | H | H | H | H | H | H | H | H | H | CHF₂ | C—CN | 4-CF₃ | amorphous |
| 1-185 | pyrimidin-5-yl | H | H | H | H | H | H | H | H | H | H | CHF₂ | C—CN | 4-CF₃ | viscous oil |
| 1-186 | pyrimidin-2-yl | H | H | H | H | H | H | H | H | H | H | CHF₂ | C—CN | 4-CF₃ | amorphous |
| 1-187 | pyrazin-2-yl | H | H | H | H | H | H | H | H | H | H | CHF₂ | C—CN | 4-CF₃ | m.p.: 173-176° C. |
| 1-188 | 4-Cl-phenyl | H | H | H | H | H | H | H | H | H | H | CHF₂ | C—CN | 4-SCF₃ | viscous oil |
| 1-189 | 4-Cl-phenyl | H | H | H | H | OH | H | H | H | H | H | CHF₂ | C—CN | 4-SCF₃ | viscous oil |
| 1-190 | 4-Cl-phenyl | H | H | H | H | OH | H | H | H | H | H | Me | C—CN | 2-OMe, 4-CF₃ | m.p.: 204-207° C. |
| 1-191 | 4-Cl-phenyl | H | H | H | H | OH | H | H | H | H | H | Me | C—CN | 4-CN | m.p.: 162-165° C. |
| 1-192 | 5-Me-pyrimidin-2-yl | H | H | H | H | OH | H | H | H | H | H | Me | C—CN | 4-CF₃ | m.p.: 80-84° C. |
| 1-193 | 3-Me—1H-pyrazol-2-yl | H | H | H | H | H | H | H | H | H | H | CHF₂ | C—CN | 4-CF₃ | viscous oil |
| 1-194 | 5-Me—1H-pyrazol-1-yl | H | H | H | H | H | H | H | H | H | H | CHF₂ | C—CN | 4-CF₃ | m.p.: 65-67° C. |
| 1-195 | 1,2,4-oxadiazol-3-yl | H | H | H | H | H | H | H | H | H | H | CHF₂ | C—CN | 4-CF₃ | m.p.: 68-69° C. |
| 1-196 | 5-F-pyridin-2-yl | H | H | H | H | H | H | H | H | H | H | Me | C—CN | 4-CF₃ | m.p.: 65-67° C. |
| 1-197 | 5-Me-oxazol-2-yl | H | H | H | H | H | H | H | H | H | H | Me | C—CN | 4-CF₃ | m.p.: 72-75° C. |
| 1-198 | 5-Me-1,2,4-oxadiazol-3-yl | H | H | H | H | H | H | H | H | H | H | Me | C—CN | 2-OMe, 4-CF₃ | m.p.: 79-81° C. |
| 1-199 | 5-Me-1,2,4-oxadiazol-3-yl | H | H | H | H | H | H | H | H | H | H | CHF₂ | C—CN | 2-OMe, 4-OCF₃ | m.p.: 153-154° C. |
| 1-200 | 5-Me-isoxazol-3-yl | H | H | H | H | H | H | H | H | H | H | CHF₂ | C—CN | 4-CF₃ | m.p.: 59-61° C. |
| 1-201 | 2,4-F₂-phenyl | H | H | H | H | OMe | H | H | H | H | H | Me | C—CN | 4-CF₃ | m.p.: 78-80° C. |
| 1-202 | isoxazol-3-yl | H | H | H | H | H | H | H | H | H | H | CHF₂ | C—CN | 4-CF₃ | m.p.: 78-80° C. |
| 1-203 | 5-CF₃-1,3,4-oxadiazol-2-yl | H | H | H | H | H | H | H | H | H | H | CHF₂ | C—CN | 4-CF₃ | m.p.: 81-84° C. |
| 1-204 | 1-Me—1H-tetrazol-5-yl | H | H | H | H | H | H | H | H | H | H | CHF₂ | C—CN | 4-CF₃ | m.p.: 85-87° C. |
| 1-205 | 5-Me-1,2,4-oxadiazol-3-yl | H | H | H | H | H | H | H | H | H | H | Me | C—CN | 4-CF₃ | m.p.: 162-164° C. |
| 1-206 | 5-CF₃-isoxazol-3-yl | H | H | H | H | H | H | H | H | H | H | CHF₂ | C—CN | 4-CF₃ | viscous oil |
| 1-207 | 5-Me-pyridin-2-yl | H | H | H | H | H | H | H | H | H | H | CHF₂ | C—CN | 4-CF₃ | viscous oil |
| 1-208 | 5-Me-pyridin-2-yl | H | H | H | H | H | H | H | H | H | H | Me | C—CN | 4-CF₃ | viscous oil |
| 1-209 | 6-Me-pyridazin-3-yl | H | H | H | H | H | H | H | H | H | H | CHF₂ | C—CN | 4-CF₃ | m.p.: 113-115° C. |
| 1-210 | pyrimidin-4-yl | H | H | H | H | H | H | H | H | H | H | CHF₂ | C—CN | 4-CF₃ | viscous oil |
| 1-211 | 3-Me-4-Cl—1H-pyrazol-1-yl | H | H | H | H | CN | H | H | H | H | H | CHF₂ | C—CN | 4-CF₃ | m.p.: 105-107° C. |
| 1-212 | 5-Me-4-Cl—1H-pyrazol-1-yl | H | H | H | H | CN | H | H | H | H | H | CHF₂ | C—CN | 4-CF₃ | viscous oil |
| 1-213 | 5-Me-pyrimidin-2-yl | H | H | H | H | H | H | H | H | H | H | Me | C—CN | 4-CF₃ | viscous oil |
| 1-214 | 5-Me-1,2,4-oxadiazol-3-yl | H | H | H | H | OMe | H | H | H | H | H | Me | C—CN | 4-CF₃ | viscous oil |
| 1-215 | 5-Me-1,2,4-oxadiazol-3-yl | H | H | H | H | H | H | H | H | H | H | Me | C—CN | 4-CF₃ | viscous oil |
| 1-216 | 4-F-phenyl | H | H | H | H | H | H | H | H | H | H | Me | C—CN | 4-CF₃ | viscous oil |
| 1-217 | 5-Me-thiazol-2-yl | H | H | H | H | H | H | H | H | H | H | CHF₂ | C—CN | 4-CF₃ | viscous oil |
| 1-218 | 1H-tetrazol-5-yl | H | H | H | H | H | H | H | H | H | H | CHF₂ | C—CN | 4-CF₃ | m.p.: 163-165° C. |
| 1-219 | 4-Me-4H-triazol-3-yl | H | H | H | H | H | H | H | H | H | H | CHF₂ | C—CN | 4-CF₃ | m.p.: 96-98° C. |
| 1-220 | 1H-pyrrol-1-yl | H | H | H | H | H | H | H | H | H | H | CHF₂ | C—CN | 4-CF₃ | m.p.: 96-98° C. |
| 1-221 | 2,4-F₂-phenyl | H | H | H | H | OMe | H | H | H | H | H | Me | C—CN | 2-OMe, 4-CF₃ | m.p.: 88-90° C. |
| 1-222 | 5-Me-1,2,4-oxadiazol-3-yl | H | H | H | H | H | H | H | H | H | H | Me | C—CN | 4-SCF₃ | m.p.: 60-62° C. |
| 1-223 | 5-Me-1,2,4-oxadiazol-3-yl | H | H | H | H | H | H | H | H | H | H | CHF₂ | C—CN | 4-CF₃ | m.p.: 58-60° C. |
| 1-224 | 4-F-phenyl | H | H | H | H | H | H | H | H | H | H | H | C—CN | 4-CF₃ | m.p.: 76-78° C. |
| 1-225 | 4-F-phenyl | H | H | H | H | OMe | H | H | H | H | H | Me | C—CN | 4-CF₃ | m.p.: 60-62° C. |

TABLE 1-continued

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-226 | 5-Me-1,2,4-oxadiazol-3-yl | H | H | H | H | Me | H | H | H | H | H | $CHF_2$ | C—CN | 4-$CF_3$ | m.p.: 71-73° C. |
| 1-227 | 5-Me-1,2,4-oxadiazol-3-yl | H | H | H | H | H | H | H | H | H | H | $CF_3$ | C—CN | 4-$CF_3$ | m.p.: 68-70° C. |
| 1-228 | 4-Cl-phenyl | H | H | H | H | OH | H | H | H | H | H | $CHF_2$ | C—C(=O)NH₂ | 4-$CF_3$ | m.p.: 148-150° C. |
| 1-229 | 5-Me-1,2,4-oxadiazol-3-yl | H | H | H | H | OH | H | H | H | H | H | $CHF_2$ | C—C(=O)NH₂ | 4-$CF_3$ | viscous oil |
| 1-230 | 4-Cl-phenyl | H | H | H | H | H | H | H | H | H | H | Me | N | 4-$CF_3$ | m.p.: 185-188° C. |
| 1-231 | 6-Me-pyridazin-3-yl | H | H | H | H | H | H | H | H | H | H | Me | C—CN | 4-$CF_3$ | viscous oil |
| 1-232 | 5-F-pyrimidin-2-yl | H | H | H | H | H | H | H | H | H | H | $CHF_2$ | C—CN | 4-$CF_3$ | viscous oil |
| 1-233 | 5-F-pyrimidin-2-yl | H | H | H | H | H | H | H | H | H | H | Me | C—CN | 4-$CF_3$ | viscous oil |
| 1-234 | 4-Cl-phenyl | H | H | H | H | Me | H | H | H | H | H | $CHF_2$ | C—CN | 4-$CF_3$ | viscous oil |
| 1-235 | 4-Cl-phenyl | H | H | H | H | Me | H | H | H | H | H | Me | C—CN | 4-$CF_3$ | viscous oil |
| 1-236 | 1H-imidazol-1-yl | H | H | H | H | H | H | H | H | H | H | $CHF_2$ | C—CN | 4-$CF_3$ | m.p.: 92-94° C. |
| 1-237 | 3-Me-1,2,4-oxadiazol-5-yl | H | H | H | H | H | H | H | H | H | H | Me | C—CN | 4-$CF_3$ | m.p.: 68-71° C. |
| 1-238 | 5-ⁱPr-1,2,4-oxadiazol-3-yl | H | H | H | H | H | H | H | H | H | H | $CHF_2$ | C—CN | 4-$CF_3$ | m.p.: 68-71° C. |
| 1-239 | 5-ⁱPr-1,2,4-oxadiazol-3-yl | H | H | H | H | H | H | H | H | H | H | Me | C—CN | 4-$CF_3$ | m.p.: 78-81° C. |
| 1-240 | 5-Me-1,2,4-oxadiazol-2-yl | H | H | H | H | H | H | H | H | H | H | $CHF_2$ | C—CN | 4-$CF_3$ | m.p.: 176-178° C. |
| 1-241 | 1-Me-1H-1,2,4-triazol-5-yl | H | H | H | H | H | H | H | H | H | H | $CHF_2$ | C—CN | 4-$CF_3$ | m.p.: 68-70° C. |
| 1-242 | 1-Me-1H-1,2,4-triazol-5-yl | H | H | H | H | H | H | H | H | H | H | Me | C—CN | 4-$CF_3$ | m.p.: 70-72° C. |
| 1-243 | 2-Me-thiazol-4-yl | H | H | H | H | H | H | H | H | H | H | $CHF_2$ | C—CN | 4-$CF_3$ | m.p.: 69-71° C. |
| 1-244 | 5-Me-1,2,4-oxadiazol-3-yl | H | H | H | H | H | H | H | H | H | H | H | N | 4-$CF_3$ | m.p.: 143-145° C. |
| 1-245 | 6-Me-pyridazin-3-yl | H | H | H | H | H | H | H | H | H | H | Me | C—CN | 4-CN | amorphous |
| 1-246 | 5-Me-pyrimidin-2-yl | H | H | H | H | H | H | H | H | H | H | Me | C—CN | 4-CN | viscous oil |
| 1-247 | 1-Me-1H-pyrazol-3-yl | H | H | H | H | H | H | H | H | H | H | Me | C—CN | 4-$CF_3$ | m.p.: 72-75° C. |
| 1-248 | 1-Me-1H-pyrazol-5-yl | H | H | H | H | H | H | H | H | H | H | Me | C—CN | 4-$CF_3$ | m.p.: 78-80° C. |
| 1-249 | 2-F-4-Me-phenyl | H | H | H | H | Et | H | H | H | H | H | $CHF_2$ | C—CN | 4-$CF_3$ | m.p.: 93-95° C. |
| 1-250 | 5-Me-1,3,4-thiadiazol-2-yl | H | H | H | H | OH | H | H | H | H | H | $CHF_2$ | C—CN | 4-$CF_3$ | m.p.: 92-94° C. |
| 1-251 | 4-Cl-phenyl | H | H | H | H | H | H | H | H | H | H | $CF_3$ | C—CN | 4-$CF_3$ | m.p.: 163-165° C. |
| 1-252 | 5-Me-pyrimidin-2-yl | H | H | H | H | OMe | H | H | H | H | H | $CHF_2$ | C—CN | 4-$CF_3$ | m.p.: 200° C. up |
| 1-253 | 5-Me-pyrimidin-2-yl | H | H | H | H | OMe | H | H | H | H | H | $CHF_2$ | C—CN | 4-$CF_3$ | m.p.: 200° C. up |
| 1-254 | 2-F-4-Me-phenyl | H | H | H | H | OMe | H | H | H | H | H | Me | C—CN | 4-$CF_3$ | viscous oil |
| 1-255 | 4-Cl-phenyl | H | H | H | H | OH | H | H | H | H | H | $CHF_2$ | C—CN | 4-$OCF_3$ | viscous oil |
| 1-256 | 5-Me-1,2,4-oxadiazol-3-yl | H | H | H | H | Me | H | H | H | H | H | $CHF_2$ | C—CN | 4-$CF_3$ | m.p.: 78-80° C. |
| 1-257 | 4-F-2-Me-phenyl | H | H | H | H | OH | H | H | H | H | H | $CHF_2$ | C—CN | 4-$CF_3$ | m.p.: 90-91° C. |
| 1-258 | 4-F-2-Me-phenyl | H | H | H | H | OMe | H | H | H | H | H | $CHF_2$ | C—CN | 4-$CF_3$ | m.p.: 98-100° C. |
| 1-259 | 5-Me-1,2,4-oxadiazol-3-yl | H | H | H | H | H | H | H | H | H | OH | $CHF_2$ | C—CN | 4-$CF_3$ | viscous oil |
| 1-260 | 4-Cl-phenyl | H | H | H | H | OH | H | H | H | H | OH | $CHF_2$ | C—Br | 4-Cl | viscous oil |
| 1-261 | 4-Cl-phenyl | H | H | H | H | OH | H | H | H | H | H | $CHF_2$ | C—Br | 4-Cl | viscous oil |
| 1-262 | 4-Cl-phenyl | H | H | H | H | OH | H | H | H | H | H | $CHF_2$ | C—Me | 4-Cl | viscous oil |
| 1-263 | 5-Me-1,2,4-oxadiazol-3-yl | H | H | H | H | H | H | H | H | H | H | $CHF_2$ | C—CN | 3-$CF_3$ | amorphous |
| 1-264 | 5-Me-1,2,4-oxadiazol-3-yl | H | H | H | H | H | H | H | H | H | H | $CHF_2$ | C—CN | 4-Cl | viscous oil |
| 1-265 | 5-Me-1,2,4-oxadiazol-3-yl | H | H | H | H | H | H | H | H | H | H | $CHF_2$ | C—CN | 4-F | viscous oil |
| 1-266 | 5-Me-1,2,4-oxadiazol-3-yl | H | H | H | H | H | H | H | H | H | H | $CHF_2$ | C—CN | 3,4-$F_2$ | viscous oil |
| 1-267 | 5-Me-pyrimidin-2-yl | H | H | H | H | H | H | H | H | H | H | $CHF_2$ | C—CN | 4-CN | viscous oil |
| 1-268 | 5-Me-pyrimidin-2-yl | H | H | H | H | H | H | H | H | H | H | $CHF_2$ | C—CN | 3-$CF_3$ | amorphous |
| 1-269 | 4-Cl-phenyl | H | H | H | H | OH | H | H | H | H | H | $CHF_2$ | C—C(=N—OH)NH₂ | 4-(5-$CF_3$-pyridin-2-yl) | viscous oil |
| 1-270 | 5-Me-1,2,4-oxadiazol-3-yl | H | H | H | H | H | H | H | H | H | H | $CF_3$ | C—CN | 4-$OCF_3$ | m.p.: 138-142° C. |
| 1-271 | 5-Me-pyrimidin-2-yl | H | H | H | H | H | H | H | H | H | H | $CHF_2$ | C—CN | 4-Cl | viscous oil |
| 1-272 | 5-Me-pyrimidin-2-yl | H | H | H | H | H | H | H | H | H | H | $CHF_2$ | C—CN | 4-F | viscous oil |
| 1-273 | 5-Me-1,2,4-oxadiazol-3-yl | H | H | H | H | H | H | H | H | H | H | $CF_3$ | C—CN | 4-S(=O)$CF_3$ | m.p.: 71-74° C. |
| 1-274 | 5-Me-1,2,4-oxadiazol-3-yl | H | H | H | H | H | H | H | H | H | H | $CF_3$ | C—(1,2,4-oxadiazol-3-yl) | 4-$OCF_3$ | viscous oil |
| 1-275 | 5-Me-1,2,4-oxadiazol-3-yl | H | H | H | H | H | H | H | H | H | H | $CF_3$ | C—(5-Me-1,2,4-oxadiazol-3-yl) | 4-$OCF_3$ | viscous oil |

TABLE 1-continued

| Compound No. | Ar | R¹ | R² | R³ | R⁴ | R⁵ | R⁶ | R⁷ | R⁸ | R⁹ | $X^{2a}$ | $X^{2b}$ | A' | $(X^1)n$ | Physical Properties |
|---|---|---|---|---|---|---|---|---|---|---|---|---|---|---|---|
| 1-276 | 5-Me-1,2,4-oxadiazol-3-yl | H | H | H | H | H | H | H | H | H | H | CF₃ | C-(5-CF₃-1,2,4-oxadiazol-3-yl) | 4-OCF₃ | viscous oil |
| 1-277 | 5-Me-1,2,4-oxadiazol-3-yl | H | H | H | H | H | H | H | H | H | H | CF₃ | C-(thiazol-2-yl) | 4-OCF₃ | viscous oil |
| 1-278 | 5-Me-1,2,4-oxadiazol-3-yl | H | H | H | H | H | H | H | H | H | H | CF₃ | C-(4-Me-thiazol-2-yl) | 4-OCF₃ | viscous oil |
| 1-279 | 5-Me-1,2,4-oxadiazol-5-yl | H | H | H | H | H | H | H | H | H | H | CHF₂ | C—CN | 4-S(=O)₂CF₃ | amorphous |
| 1-280 | 3-Me-isoxazol-5-yl | H | H | H | H | H | H | H | H | H | H | CHF₂ | C—CN | 4-CF₃ | m.p.: 201-202° C. |
| 1-281 | 4-Me—1H-1,2,3-triazol-1-yl | H | H | H | H | H | H | H | H | H | H | CHF₂ | C—CN | 4-CF₃ | m.p.: 108-110° C. |
| 1-282 | 1H-tetrazol-1-yl | H | H | H | H | Et | H | H | H | H | H | CHF₂ | C—CN | 4-CF₃ | m.p.: 80-82° C. |
| 1-283 | 5-Me-1,2,4-oxadiazol-3-yl | H | H | H | H | Me | H | H | H | H | H | CF₃ | C—CN | 4-CF₃ | m.p.: 188-190° C. |
| 1-284 | 4-Cl-phenyl | H | H | H | H | H | H | H | H | H | H | CF₃ | C—CN | 4-CF₃ | amorphous |
| 1-285 | 5-Me-1,2,4-oxadiazol-3-yl | H | H | H | H | H | H | H | H | H | H | CF₃ | C—CO₂Me | 3-OCF₃ | viscous oil |
| 1-286 | 5-Me-1,2,4-oxadiazol-3-yl | H | H | H | H | H | H | H | H | H | H | Me | C—CH₂OH | 4-CF₃ | viscous oil |
| 1-287 | 5-Me-1,2,4-oxadiazol-3-yl | H | H | H | H | H | H | H | H | H | H | Me | C—CO₂Et | 4-CF₃ | viscous oil |
| 1-288 | 4-Cl-phenyl | H | H | H | H | OH | H | H | H | H | H | Me | C—C(=O)NMe₂ | 4-CF₃ | amorphous |
| 1-289 | 4-Cl-phenyl | H | H | H | H | OH | H | H | H | H | H | Me | C—CH₂OH | 4-CF₃ | viscous oil |
| 1-290 | 4-Cl-phenyl | H | H | H | H | OH | H | H | H | H | H | CF₃ | C—CN | 4-CF₃ | viscous oil |
| 1-291 | 5-Me-1,2,4-oxadiazol-3-yl | H | H | H | H | H | H | H | H | H | H | CF₃ | C—CN | 3,4-Cl₂ | m.p.: 163-165° C. |
| 1-292 | 5-Me-1,2,4-oxadiazol-3-yl | H | H | H | H | H | H | H | H | H | H | Me | C—CN | 4-Cl | viscous oil |
| 1-293 | 5-Me-pyrimidin-2-yl | H | H | H | H | H | H | H | H | H | H | CF₃ | C—CN | 4-CN | m.p.: 172-175° C. |
| 1-294 | 5-Me-pyrimidin-2-yl | H | H | H | H | H | H | H | H | H | H | Me | C—CN | 4-Cl | viscous oil |
| 1-295 | 5-Me-1,2,4-oxadiazol-3-yl | H | H | H | H | H | H | H | H | H | H | Me | C—C(=O)NHMe | 4-CF₃ | viscous oil |
| 1-296 | 5-Me-1,2,4-oxadiazol-3-yl | H | H | H | H | H | H | H | H | H | H | Me | C—C(=O)NMe₂ | 4-CF₃ | viscous oil |
| 1-297 | 5-Me-1,2,4-oxadiazol-3-yl | H | H | H | H | H | H | H | H | H | H | CF₃ | C—C(=O)H | 4-CF₃ | viscous oil |
| 1-298 | 5-Me-1,2,4-oxadiazol-3-yl | H | H | H | H | H | H | H | H | H | H | Me | C—C(=N—OMe)H | 4-CF₃ | viscous oil |
| 1-299 | 5-Me-1,2,4-oxadiazol-3-yl | H | H | H | H | H | H | H | H | H | H | Me | C—C≡CH | 4-CF₃ | viscous oil |
| 1-300 | 5-Me-1,2,4-oxadiazol-3-yl | H | H | H | H | H | H | H | H | H | H | Me | C—CH=CH₂ | 4-CF₃ | viscous oil |
| 1-301 | 5-Me-1,2,4-oxadiazol-3-yl | H | H | H | H | H | H | H | H | H | H | Me | C—CN | 4-SCF₃ | m.p.: 62-64° C. |
| 1-302 | 5-Me-1,2,4-oxadiazol-3-yl | H | H | H | H | H | H | H | H | H | H | Me | C—CN | 4-S(=O)CF₃ | m.p.: 48-51° C. |
| 1-303 | 5-Me-1,2,4-oxadiazol-3-yl | H | H | H | H | H | H | H | H | H | H | Me | C—CN | 4-S(=O)₂CF₃ | m.p.: 69-72° C. |
| 1-304 | 5-Me-1,2,4-oxadiazol-3-yl | H | H | H | H | H | H | H | H | H | H | Me | C—CN | 4-CO₂Bu | m.p.: 80-83° C. |
| 1-305 | 5-Me-1,2,4-oxadiazol-3-yl | H | H | H | H | H | H | H | H | H | H | CHF₂ | C—CN | 4-Br | amorphous |
| 1-306 | 4-Cl-phenyl | H | H | H | H | OH | H | H | H | H | H | Me | C—C(=N—OH)H | 4-CF₃ | m.p.: 167-170° C. |
| 1-307 | 4-Cl-phenyl | H | H | H | H | OH | H | H | H | H | H | Me | C—C(=O)H | 4-CF₃ | viscous oil |
| 1-308 | 5-Me-1,2,4-oxadiazol-3-yl | H | H | H | H | H | H | H | H | H | H | Me | C—CN | 2-Cl-4-(2,4-Cl₂-phenyl) | m.p.: 78-81° C. |
| 1-309 | 5-Me-1,2,4-oxadiazol-3-yl | H | H | H | H | H | H | H | H | H | H | Me | C—CN | 2,4-Cl₂ | m.p.: 67-70° C. |
| 1-310 | 5-Me-1,2,4-oxadiazol-3-yl | H | H | H | H | H | H | H | H | H | H | Me | C—CN | 3,4-Cl₂ | m.p.: 58-61° C. |
| 1-311 | 5-Me-1,2,4-oxadiazol-3-yl | H | H | H | H | H | H | H | H | H | H | CHF₂ | C—CN | 2-F, 4-CF₃ | viscous oil |
| 1-312 | 5-Me-1,2,4-oxadiazol-3-yl | H | H | H | H | H | H | H | H | H | H | CHF₂ | C—CN | 2-Cl, 4-CF₃ | viscous oil |
| 1-313 | 5-Me-1,2,4-oxadiazol-3-yl | H | H | H | H | H | H | H | H | H | H | CF₃ | C—CN | 3-F, 4-CF₃ | viscous oil |
| 1-314 | 5-Me-1,2,4-oxadiazol-3-yl | H | H | H | H | H | H | H | H | H | H | CF₃ | C—CN | 2-OMe, 4-CF₃ | viscous oil |
| 1-315 | 4-Cl-phenyl | H | H | H | H | OH | H | H | H | H | H | CHF₂ | C—CN | 4-CF₃ | amorphous |
| 1-316 | 1-Me—1H-pyrazol-3-yl | H | H | H | H | H | H | H | H | H | H | Me | C—CN | 4-CF₃ | viscous oil |
| 1-317 | 1-Me—1H-pyrazol-5-yl | H | H | H | H | H | H | H | H | H | H | Me | C—CN | 4-CF₃ | viscous oil |
| 1-318 | 1-Et—1H-pyrazol-3-yl | H | H | H | H | H | H | H | H | H | H | Me | C—CN | 4-CF₃ | viscous oil |
| 1-319 | 1-Et—1H-pyrazol-5-yl | H | H | H | H | H | H | H | H | H | H | Me | C—CN | 4-C(CF₃)₂OMe | m.p.: 91-93° C. |
| 1-320 | 5-Me-1,2,4-oxadiazol-3-yl | H | H | H | H | H | H | H | H | H | H | Me | C—CN | 4-Br | viscous oil |
| 1-321 | 5-Me-1,2,4-oxadiazol-3-yl | H | H | H | H | H | H | H | H | H | H | CHF₂ | C—CN | 4-OCF₂CF₂H | viscous oil |
| 1-322 | 5-Me-1,2,4-oxadiazol-3-yl | H | H | H | H | H | H | H | H | H | H | CHF₂ | C—CN | 4-OCF₂H | viscous oil |
| 1-323 | 5-Me-1,2,4-oxadiazol-3-yl | H | H | H | H | H | H | H | H | H | H | CHF₂ | C—CN | 4-Bu | viscous oil |
| 1-324 | 5-Me-1,2,4-oxadiazol-3-yl | H | H | H | H | H | H | H | H | H | H | Me | C—CN | 4-CF₂CF₃ | m.p.: 68-70° C. |
| 1-325 | 5-Me-1,2,4-oxadiazol-3-yl | H | H | H | H | H | H | H | H | H | H | Me | C—CN | 4-CF₂H | m.p.: 70-72° C. |

TABLE 1-continued

| Compound No. | Ar | $R^1$ | $R^2$ | $R^3$ | $R^4$ | $R^5$ | $R^6$ | $R^7$ | $R^8$ | $R^9$ | $X^{2a}$ | $X^{2b}$ | A' | $(X^1)n$ | Physical Properties |
|---|---|---|---|---|---|---|---|---|---|---|---|---|---|---|---|
| 1-326 | 5-Me-1,2,4-oxadiazol-3-yl | H | H | Me | H | H | H | H | H | H | H | $CHF_2$ | C—CN | 4-$CF_3$ | viscous oil |
| 1-327 | 5-Me-1,2,4-oxadiazol-3-yl | H | H | Me | H | H | H | H | H | H | H | $CHF_2$ | C—CN | 4-$CF_3$ | viscous oil |
| 1-328 | 5-Me-1,2,4-oxadiazol-3-yl | H | H | Et | H | H | H | H | H | H | H | $CHF_2$ | C—CN | 4-$CF_3$ | viscous oil |
| 1-329 | 5-Me-1,2,4-oxadiazol-3-yl | H | H | Et | H | H | H | H | H | H | H | $CHF_2$ | C—CN | 4-$CF_3$ | viscous oil |
| 1-330 | 5-Me-1,2,4-oxadiazol-3-yl | H | H | H | H | H | H | H | H | H | H | $CHF_2$ | C—CN | 4-(5-$CF_3$-pyridin-2-yl) | amorphous |
| 1-331 | 5-Me-1,2,4-oxadiazol-3-yl | H | H | H | H | H | H | H | H | H | H | OMe | C—CN | 4-$CF_3$ | viscous oil |
| 1-332 | 5-Me-pyrimidin-2-yl | H | H | H | H | H | H | H | H | H | H | OMe | C—CN | 4-$CF_3$ | viscous oil |
| 1-333 | 5-Me-1,2,4-oxadiazol-3-yl | H | H | H | H | H | H | H | H | H | H | Cl | C—CN | 4-$CF_3$ | viscous oil |
| 1-334 | 4-Cl-phenyl | H | H | H | H | OH | H | H | H | H | H | $CHF_2$ | C—C(=N—OAc)H | 4-$CF_3$ | viscous oil |
| 1-335 | 4-Cl-phenyl | H | H | H | H | OH | H | H | H | H | H | $CHF_2$ | C—C(=N—OAc)H | 4-$CF_3$ | viscous oil |
| 1-336 | 4-Me-pyrimidin-2-yl | H | H | H | H | H | H | H | H | H | H | $CHF_2$ | C—CN | 4-$CF_3$ | viscous oil |
| 1-337 | 5-Me-1,2,4-oxadiazol-3-yl | H | H | H | H | H | H | H | H | H | H | SMe | C—CN | 4-O$CH_2CF_3$ | viscous oil |
| 1-338 | 5-Me-1,2,4-oxadiazol-3-yl | H | H | H | H | H | H | H | H | H | H | $CHF_2$ | C—CN | 4-O$CH_2CF_2CF_3$ | viscous oil |
| 1-339 | 5-Me-1,2,4-oxadiazol-3-yl | H | H | H | H | H | H | H | H | H | H | $CHF_2$ | C—CN | 4-O$CH_2CH_2CF_3$ | viscous oil |
| 1-340 | 5-Me-1,2,4-oxadiazol-3-yl | H | H | H | H | H | H | H | H | H | H | $CHF_2$ | C—CN | 2-Me, 4-$CF_3$ | m.p.: 50-52° C. |
| 1-341 | 5-Me-1,2,4-oxadiazol-3-yl | H | H | H | H | H | H | H | H | H | H | Me | C—CN | 4-C($CF_3$)$_2$F | m.p.: 82-84° C. |
| 1-342 | 5-Me-1,2,4-oxadiazol-3-yl | H | H | H | H | H | H | H | H | H | H | Me | C—CN | $SF_5$ | viscous oil |
| 1-343 | 5-Me-1,2,4-oxadiazol-3-yl | H | H | H | H | H | H | H | H | H | H | $CF_3$ | C—CN | 4-OPh | viscous oil |
| 1-344 | 5-Me-1,2,4-oxadiazol-3-yl | H | H | H | H | H | H | H | H | H | H | $CHF_2$ | C—CN | 4-O$CH_2CH_2CF_3$ | viscous oil |
| 1-345 | 5-Me-1,2,4-oxadiazol-3-yl | H | H | H | H | H | H | H | H | H | H | $CHF_2$ | C—CN | 4-$CF_3$ | viscous oil |
| 1-346 | 5-Me-1,2,4-oxadiazol-3-yl | H | H | H | H | H | H | H | H | H | H | S(=O)$_2CH_3$ | C—CN | 2-Me, 4-$CF_3$ | m.p.: 248-250° C. |
| 1-347 | 5-Me-1,2,4-oxadiazol-3-yl | H | H | H | H | H | H | H | H | H | H | Me | C—CN | 4-$NO_2$ | m.p.: 68-70° C. |
| 1-348 | 5-Me-1,2,4-oxadiazol-3-yl | H | H | H | H | H | H | H | H | H | H | $CF_3$ | C—C(=OH | m.p.: 188-191° C. |
| 1-349 | 5-Me-1,2,4-oxadiazol-3-yl | H | H | H | H | H | H | H | H | H | H | $CF_3$ | C—C(=N—OMe)H | m.p.: 177-180° C. |
| 1-350 | 5-Me-1,2,4-oxadiazol-3-yl | H | H | H | H | H | H | H | H | H | H | $CF_3$ | C—CN | 2-CN, 4-$CF_3$ | viscous oil |
| 1-351 | 5-Me-1,2,4-oxadiazol-3-yl | H | H | H | H | H | H | H | H | H | H | $CF_3$ | C—CN | 4-$CF_3$ | viscous oil |
| 1-352 | 4-Cl-phenyl | H | H | H | H | OH | H | H | H | H | H | H | C—S(=O)Me | 4-$CF_3$ | viscous oil |
| 1-353 | 4-Cl-phenyl | H | H | H | H | OH | H | H | H | H | H | H | C—S(=O)$_2$Me | 4-$CF_3$ | viscous oil |
| 1-354 | 4-Cl-phenyl | H | H | H | H | OH | H | H | H | H | H | H | C—CN | 4-O$^i$Pr | viscous oil |
| 1-355 | 5-Me-1,2,4-oxadiazol-3-yl | H | H | H | H | H | H | H | H | H | H | $CF_3$ | C—CN | 4-OC($CF_3$)$_2$H | viscous oil |
| 1-356 | 5-Me-1,2,4-oxadiazol-3-yl | H | H | H | H | H | H | H | H | H | H | $CF_3$ | C—CN | 4-$CF_3$ | m.p.: 84-86° C. |
| 1-357 | 1,2,4-thiadiazol-3-yl | H | H | H | H | H | H | H | H | H | H | $CHF_2$ | C—CN | 4-$CF_3$ | viscous oil |
| 1-358 | 5-Me-1,2,4-thiadiazol-3-yl | H | H | H | H | H | H | H | H | H | H | $CHF_2$ | C—CN | 4-$CF_3$ | viscous oil |
| 1-359 | 4-Me-phenyl | H | H | H | H | H | H | H | H | H | H | $CHF_2$ | C—C(=S)$NH_2$ | 4-$CF_3$ | m.p.: 155-159° C. |
| 1-360 | 4-Me-phenyl | H | H | H | H | H | H | H | H | H | H | Me | C—C(=S)$NH_2$ | 4-$CF_3$ | m.p.: 143-145° C. |
| 1-361 | 5-Me-1,2,4-oxadiazol-3-yl | H | H | H | H | H | H | H | H | H | H | $CHF_2$ | C—C(=S)$NH_2$ | 4-$CF_3$ | m.p.: 169-171° C. |
| 1-362 | 5-Me-1,2,4-oxadiazol-3-yl | H | H | H | H | H | H | H | H | H | H | $CHF_2$ | C—C(=NH)SMe | 4-$CF_3$ | m.p.: 91-93° C. |

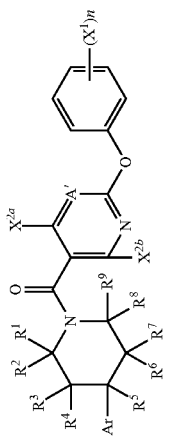

(I-2)

TABLE 2

| Compound No. | Ar | R¹ | R² | R³ | R⁴ | R⁵ | R⁶ | R⁷ | R⁸ | R⁹ | X²ᵃ | X²ᵇ | A' | (X¹)n | Physical Properties |
|---|---|---|---|---|---|---|---|---|---|---|---|---|---|---|---|
| 2-1 | 4-Cl-phenyl | H | H | H | H | OH | H | H | H | H | H | H | CH | 4-CF₃ | m.p.: 136-140° C. |
| 2-2 | 4-Cl-phenyl | H | H | H | H | OH | H | H | H | H | H | CF₃ | N | 4-CF₃ | m.p.: 201-204° C. |
| 2-3 | 2-Cl-phenyl | H | H | H | H | OH | H | H | H | H | H | H | CH | 4-CF₃ | amorphous |
| 2-4 | 4-Cl-phenyl | H | H | H | H | H | H | H | H | H | CF₃ | H | CH | 4-CF₃ | viscous oil |
| 2-5 | 4-Cl-phenyl | H | H | H | H | OH | H | H | H | H | H | CF₃ | CH | 4-CF₃ | viscous oil |
| 2-6 | 4-Cl-phenyl | H | H | H | H | OH | H | H | H | H | H | H | C—Cl | 4-CF₃ | viscous oil |
| 2-7 | 2-F-phenyl | H | H | H | H | OH | H | H | H | H | H | H | CH | 4-CF₃ | m.p.: 174-176° C. |
| 2-8 | 4-Cl-phenyl | H | H | H | H | OH | H | H | H | H | H | H | CH | 3-CF₃ | m.p.: 110-112° C. |
| 2-9 | 4-Cl-phenyl | H | H | H | H | OH | H | H | H | H | H | H | CH | 2-CF₃ | viscous oil |
| 2-10 | 4-Cl-phenyl | H | H | H | H | OH | H | H | H | H | H | OMe | N | 4-CF₃ | viscous oil |
| 2-11 | 4-Cl-phenyl | H | H | H | H | OH | H | H | H | H | OMe | H | CH | 4-CF₃ | viscous oil |
| 2-12 | 4-Cl-phenyl | H | H | H | H | OH | H | H | H | H | H | Me | CH | 4-CF₃ | viscous oil |
| 2-13 | 2,2-F₂-benzo[d][1,3]dioxol-4-yl | H | H | H | H | OH | H | H | H | H | H | H | CH | 4-CF₃ | m.p.: 68-70° C. |
| 2-14 | 4-Cl-phenyl | H | H | H | H | OH | H | H | H | H | H | Me | C—CN | 4-CF₃ | m.p.:129-133° C. |
| 2-15 | 5-Me-1,2,4-oxadiazol-3-yl | H | H | H | H | H | H | H | H | H | H | Me | C—CN | 4-CF₃ | m.p.:67-70° C. |
| 2-16 | 4-F-phenyl | H | H | H | H | OMe | H | H | H | H | H | Me | C—CN | 4-CF₃ | amorphous |
| 2-17 | 4-F-phenyl | H | H | H | H | OMe | H | H | H | H | H | H | C—Cl | 4-CF₃ | viscous oil |
| 2-18 | 5-Me-pyrimidin-2-yl | H | H | H | H | H | H | H | H | H | H | H | C—Cl | 4-CF₃ | amorphous |
| 2-19 | 4-F-phenyl | H | H | H | H | OMe | H | H | H | H | H | H | C—Cl | 3-CF₃ | viscous oil |
| 2-20 | 4-F-phenyl | H | H | H | H | OMe | H | H | H | H | H | H | C—Cl | 4-OCF₃ | viscous oil |

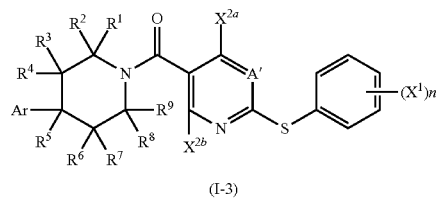

(I-3)

TABLE 11

| Compound No. | Ar | R¹ | R² | R³ | R⁴ | R⁵ | R⁶ | R⁷ | R⁸ | R⁹ | X²ᵃ | X²ᵇ | A' | (X¹)n | Physical Properties |
|---|---|---|---|---|---|---|---|---|---|---|---|---|---|---|---|
| 5-1 | 4-Cl-phenyl | H | H | H | H | OH | H | H | H | H | H | H | CH | 4-CF₃ | viscous oil |
| 5-2 | 4-Cl-phenyl | H | H | H | H | OH | H | H | H | H | H | H | C—Cl | 4-CF₃ | amorphous |

TABLE 3

| Compound No. | Structure | Physical Properties |
|---|---|---|
| 3-1 | (structure: 5-chloro-spiro[isobenzofuran-1,4'-piperidine] linked via carbonyl to pyridine bearing CN, CHF₂, and 4-CF₃-phenyl) | viscous oil |
| 3-2 | (structure: 4-(4-chlorophenyl)-4-hydroxy-azabicyclic amide linked to pyridine bearing CN, CHF₂, and 4-CF₃-phenyl) | viscous oil |

TABLE 3-continued

| Compound No. | Structure | Physical Properties |
|---|---|---|
| 3-3 | 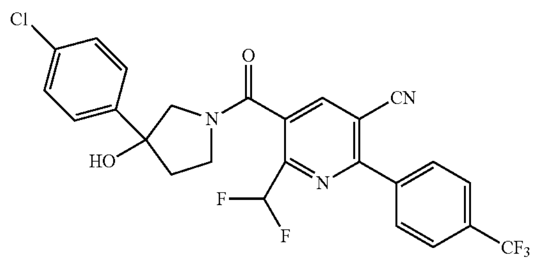 [SMILES: N#Cc1cc(C(=O)N2CCC(O)(c3ccc(Cl)cc3)C2)c(C(F)F)nc1-c1ccc(C(F)(F)F)cc1] | viscous oil |
| 3-4 | 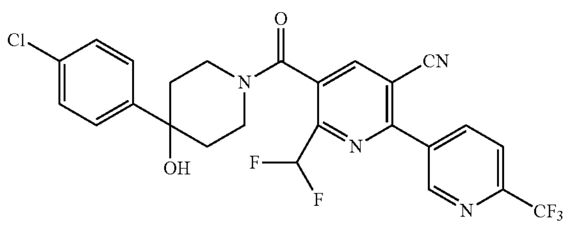 [SMILES: N#Cc1cc(C(=O)N2CCC(O)(c3ccc(Cl)cc3)CC2)c(C(F)F)nc1-c1ccc(C(F)(F)F)nc1] | m.p.: 177-180° C. |
| 3-5 | 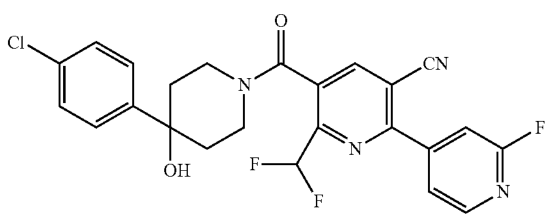 [SMILES: N#Cc1cc(C(=O)N2CCC(O)(c3ccc(Cl)cc3)CC2)c(C(F)F)nc1-c1ccnc(F)c1] | m.p :150-155° C. |
| 3-6 | 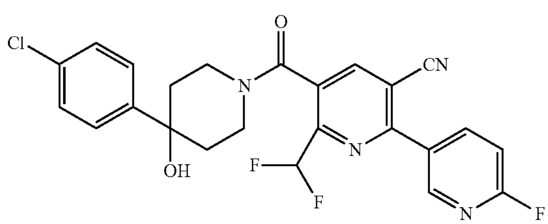 [SMILES: N#Cc1cc(C(=O)N2CCC(O)(c3ccc(Cl)cc3)CC2)c(C(F)F)nc1-c1ccc(F)nc1] | viscous oil |
| 3-7 | 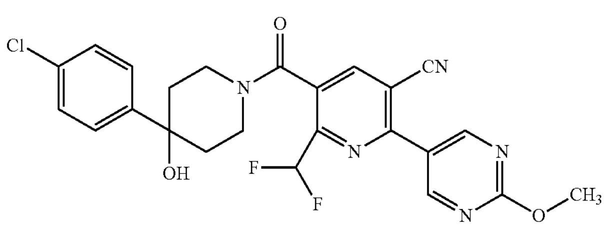 [SMILES: COc1ncc(-c2nc(C(F)F)c(C(=O)N3CCC(O)(c4ccc(Cl)cc4)CC3)cc2C#N)cn1] | viscous oil |
| 3-8 | 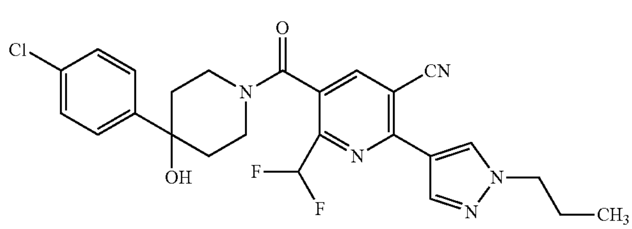 [SMILES: CCCn1cc(-c2nc(C(F)F)c(C(=O)N3CCC(O)(c4ccc(Cl)cc4)CC3)cc2C#N)cn1] | m.p.: 193-195° C. |

TABLE 3-continued

| Compound No. | Structure | Physical Properties |
|---|---|---|
| 3-9 | 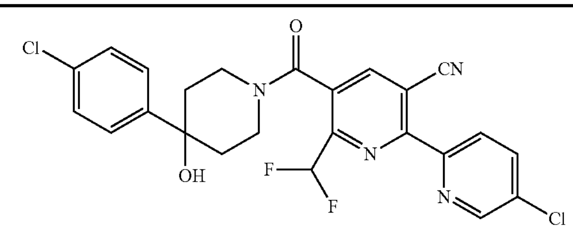 | m.p.: 175-177° C. |
| 3-10 | 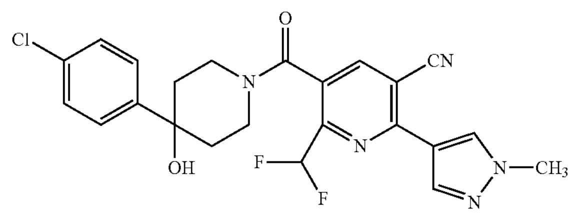 [SMILES: Cn1cc(-c2nc(C(F)F)c(C(=O)N3CCC(O)(c4ccc(Cl)cc4)CC3)cc2C#N)cn1] | m.p.: 220°C up |
| 3-11 | 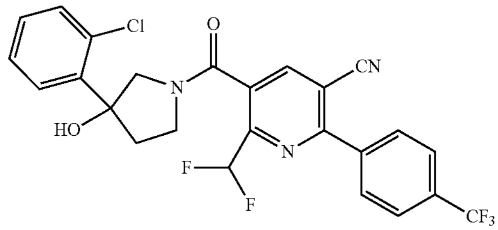 [SMILES: N#Cc1cc(C(=O)N2CCC(O)(c3ccccc3Cl)C2)c(C(F)F)nc1-c1ccc(C(F)(F)F)cc1] | m.p.: 191-195° C. |
| 3-12 | 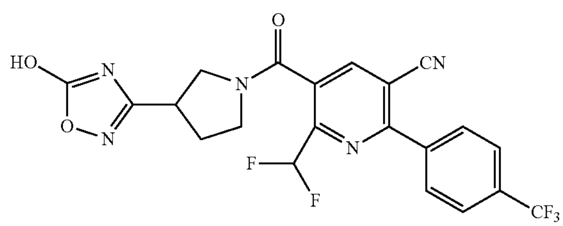 [SMILES: N#Cc1cc(C(=O)N2CCC(c3noc(O)n3)C2)c(C(F)F)nc1-c1ccc(C(F)(F)F)cc1] | m.p.: 181-184° C. |
| 3-13 | 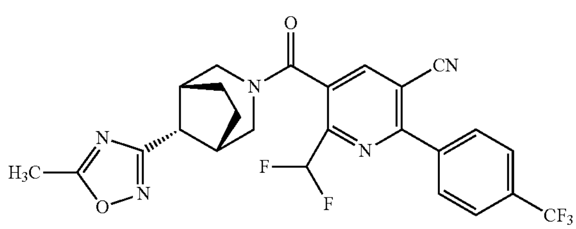 [SMILES: Cc1nc([C@H]2[C@@H]3CC[C@H]2CN(C(=O)c2cc(C#N)c(-c4ccc(C(F)(F)F)cc4)nc2C(F)F)C3)no1] | viscous oil |
| 3-14 | 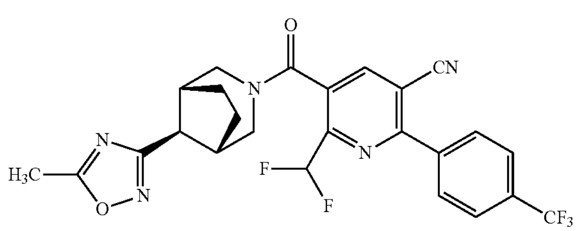 [SMILES: Cc1nc([C@@H]2[C@@H]3CC[C@H]2CN(C(=O)c2cc(C#N)c(-c4ccc(C(F)(F)F)cc4)nc2C(F)F)C3)no1] | viscous oil |
| 3-15 | 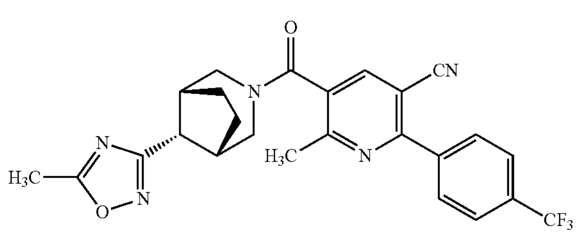 [SMILES: Cc1nc([C@H]2[C@@H]3CC[C@H]2CN(C(=O)c2cc(C#N)c(-c4ccc(C(F)(F)F)cc4)nc2C)C3)no1] | viscous oil |

TABLE 3-continued

| Compound No. | Structure | Physical Properties |
|---|---|---|
| 3-16 | 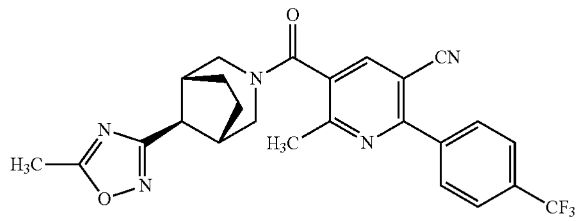 [SMILES: Cc1nc([C@@H]2[C@@H]3CC[C@H]2CN(C(=O)c2cc(C#N)c(-c4ccc(C(F)(F)F)cc4)nc2C)C3)no1] | viscous oil |
| 3-17 | 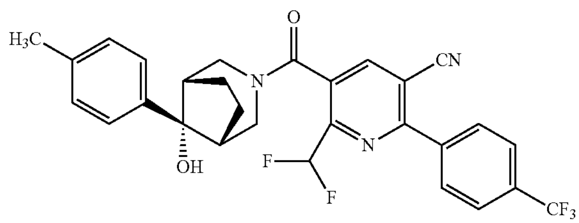 [SMILES: Cc1ccc([C@]2(O)[C@@H]3CC[C@H]2CN(C(=O)c2cc(C#N)c(-c4ccc(C(F)(F)F)cc4)nc2C(F)F)C3)cc1] | m.p.: 181-121° C. |
| 3-18 | 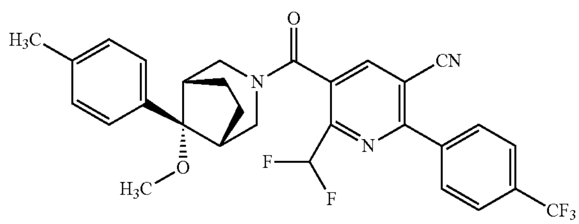 [SMILES: CO[C@@]1(c2ccc(C)cc2)[C@@H]2CC[C@H]1CN(C(=O)c1cc(C#N)c(-c3ccc(C(F)(F)F)cc3)nc1C(F)F)C2] | m.p.: 228-230° C. |
| 3-19 | 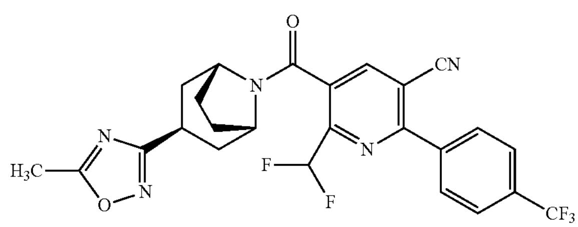 [SMILES: Cc1nc([C@H]2C[C@H]3CC[C@@H](C2)N3C(=O)c2cc(C#N)c(-c3ccc(C(F)(F)F)cc3)nc2C(F)F)no1] | viscous oil |
| 3-20 | 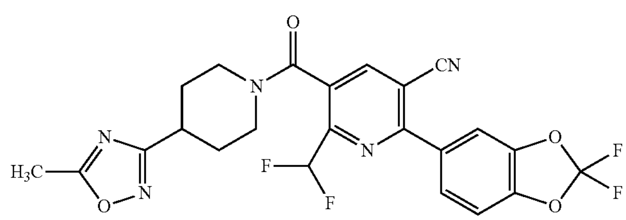 [SMILES: Cc1nc(C2CCN(C(=O)c3cc(C#N)c(-c4ccc5c(c4)OC(F)(F)O5)nc3C(F)F)CC2)no1] | viscous oil |
| 3-21 | 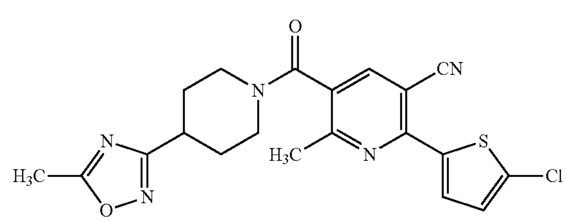 [SMILES: Cc1nc(C2CCN(C(=O)c3cc(C#N)c(-c4ccc(Cl)s4)nc3C)CC2)no1] | m.p.: 69-71° C. |
| 3-22 | 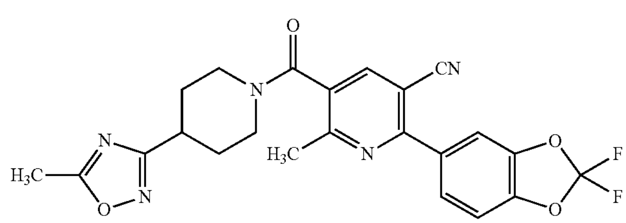 [SMILES: Cc1nc(C2CCN(C(=O)c3cc(C#N)c(-c4ccc5c(c4)OC(F)(F)O5)nc3C)CC2)no1] | viscous oil |

TABLE 3-continued

| Compound No. | Structure | Physical Properties |
|---|---|---|
| 3-23 | 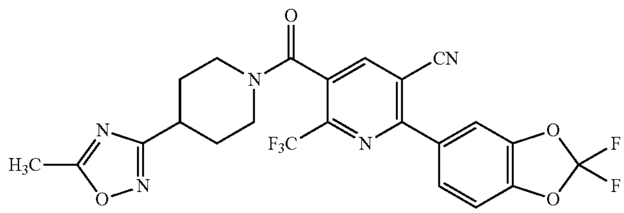 | viscous oil |
| 3-24 | 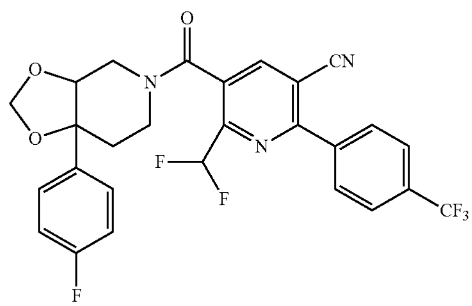 [SMILES: N#Cc1cc(C(=O)N2CCC3(c4ccc(F)cc4)OCOC3C2)c(C(F)F)nc1-c1ccc(C(F)(F)F)cc1] | viscous oil |
| 3-25 | 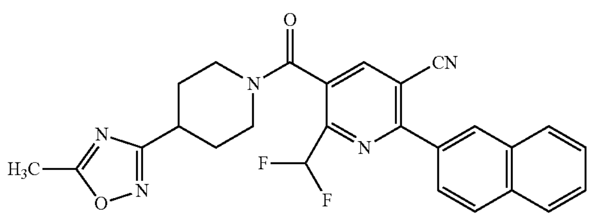 [SMILES: Cc1nc(C2CCN(C(=O)c3cc(C#N)c(-c4ccc5ccccc5c4)nc3C(F)F)CC2)no1] | viscous oil |
| 3-26 | 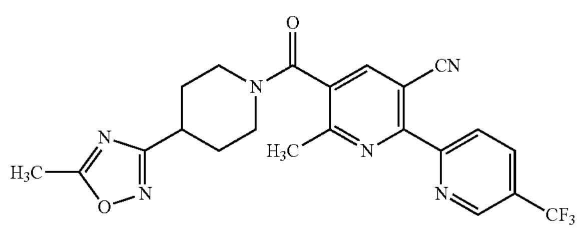 [SMILES: Cc1nc(C2CCN(C(=O)c3cc(C#N)c(-c4ccc(C(F)(F)F)cn4)nc3C)CC2)no1] | m.p.: 60-62° C. |

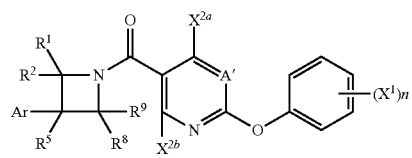

(I-4)

TABLE 4

| Compound No. | Ar | R¹ | R² | R⁵ | R⁸ | R⁹ | X²ᵃ | X²ᵇ | A' | (X¹)n | Physical Properties |
|---|---|---|---|---|---|---|---|---|---|---|---|
| 4-1 | 4-Cl-phenyl | H | H | OH | H | H | H | CHF₂ | C—CN | 4-CF₃ | m.p.: 194-197° C. |
| 4-2 | 4-Cl-phenyl | H | H | OMe | H | H | H | CHF₂ | C—CN | 4-CF₃ | m.p.: 101-106° C. |
| 4-3 | 5-Me-1,2,4-oxadiazol-3-yl | H | H | H | H | H | H | CHF₂ | C—CN | 4-CF₃ | m.p.: 163-165° C. |
| 4-4 | 5-Me-1,2,4-oxadiazol-3-yl | H | H | H | H | H | H | Me | C—CN | 4-CF₃ | m.p.: 195-198° C. |
| 4-5 | 4-F-phenyl | H | H | OH | H | H | H | CHF₂ | C—CN | 4-CF₃ | amorphous |
| 4-6 | 4-Me-phenyl | H | H | OH | H | H | H | CHF₂ | C—CN | 4-CF₃ | m.p.: 118-120° C. |
| 4-7 | 4-F-phenyl | H | H | OMe | H | H | H | CHF₂ | C—CN | 4-CF₃ | m.p.: 121-124° C. |
| 4-8 | 4-Me-phenyl | H | H | OMe | H | H | H | CHF₂ | C—CN | 4-CF₃ | m.p.: 128-130° C. |
| 4-9 | 4-Cl-phenyl | H | H | OMe | H | H | H | Me | C—CN | 4-CF₃ | amorphous |
| 4-10 | 5-Et-1,2,4-oxadiazol-3-yl | H | H | H | H | H | H | CHF₂ | C—CN | 4-CF₃ | m.p.: 154-156° C. |

TABLE 4-continued

| Compound No. | Ar | R¹ | R² | R⁵ | R⁸ | R⁹ | X²ᵃ | X²ᵇ | A' | (X¹)n | Physical Properties |
|---|---|---|---|---|---|---|---|---|---|---|---|
| 4-11 | 5-ᶜPr-1,2,4-oxadiazol-3-yl | H | H | H | H | H | H | CHF₂ | C—CN | 4-CF₃ | m.p.: 164-167° C. |
| 4-12 | 5-CF₃-1,2,4-oxadiazol-3-yl | H | H | H | H | H | H | CHF₂ | C—CN | 4-CF₃ | m.p.: 178-180° C. |
| 4-13 | 4-F-phenyl | H | H | OMe | H | H | H | CF₃ | C—CN | 4-CF₃ | m.p.: 190-192° C. |

Among the compounds shown in Table 1 to Table 4, ¹H-NMR (CDCl₃) was measured for viscous oil or compounds having physical properties of amorphous. The measured values are shown in Table 5.

TABLE 5

| Compound No. | ¹H-NMR (CDCl₃, δ ppm) |
|---|---|
| 1-1 | 1.66-2.16 (4H, m), 3.34-3.43 (2H, m), 3.65-3.73 (1H, m), 4.67-4.77 (1H, m), 6.86 (1H, t), 7.33-7.42 (4H, m), 7.82 (2H, d), 8.10-8.12 (3H, m) |
| 1-2 | 2.03-2.34 (4H, m), 3.31-3.37 (1H, m), 3.54-3.73 (2H, m), 4.92-5.04 (1H, m), 6.87 (1H, t), 7.37-7.48 (4H, m), 7.83 (2H, d), 8.10-8.13 (3H, m) |
| 1-3 | 1.78-2.07 (2H, m), 2.38-2.60 (2H, m), 2.95-3.03 (1H, m), 3.30-3.67 (2H, m), 4.61-4.67 (1H, m), 4.96-5.03 (1H, m), 6.86 (1H, t), 7.08-7.12 (4H, m), 7.82 (2H, d) 8.11 (2H, d), 8.60 (1H, s) |
| 1-4 | 1.39-1.62 (2H, m), 2.73-2.92 (2H, m), 3.37-3.47 (2H, m), 3.74-3.82 (1H, m), 4.77-4.83 (1H, m), 6.89 (1H, t), 7.28-7.30 (1H, m), 7.76-7.83 (3H, m), 8.11-8.12 (3H, m), 8.47-8.49 (1H, m) |
| 1-5 | 1.75-2.17 (4H, m), 3.22-3.77 (3H, m), 4.67-4.80 (1H, m), 7.36-7.45 (4H, m), 7.84 (2H, d) 8.14-8.19 (3H, m) |
| 1-6 | 1.65-2.19 (4H, m), 3.33-3.42 (2H, m), 3.67-3.75 (1H, m), 4.71-4.81 (1H, m), 6.88 (1H, t), 7.54-7.69 (4H, m), 7.82 (2H, d), 8.09-8.12 (3H, m) |
| 1-7 | 1.77-2.28 (4H, m), 3.02 (3H, s), 3.24-3.67 (3H, m), 4.67-4.75 (1H, m), 6.84 (1H, t), 7.49 (2H, d), 7.65 (2H, d), 7.82 (2H, d), 8.09-8.12 (3H, m) |
| 1-8 | 1.65-2.09 (4H, m), 2.85-2.99 (2H, m), 3.22-3.35 (1H, m), 3.54-3.63 (1H, m), 4.89-4.99 (1H, m), 6.89 (1H, t), 7.32 (2H, d), 7.58 (2H, d), 7.82 (2H, m) 8.10-8.12 (3H, m) |
| 1-9 | 1.75-2.21 (4H, m), 3.41-3.54 (2H, m), 3.73-3.79 (1H, m), 4.71-4.82 (1H, m), 6.88 (1H, t), 7.50-7..62 (2H, m), 7.81-7.83 (3H, m), 8.10-8.12 (3H, m) |
| 1-10 | 0.92 (3H, t), 1.31-1.40 (2H, m), 1.55-1.63 (2H, m), 1.86-2.21 (4H, m), 2.60 (2H, t), 3.29-3.50 (3H, m), 3.67-3.76 (1H, m), 4.65-4.74 (1H, m), 6.86 (1H, t), 7.20 (2H, d), 7.36 (2H, d), 7.82 (2H, d), 8.09-8.12 (3H, m) |
| 1-12 | 1.69-2.21 (4H, m), 3.30-3.43 (2H, m), 3.66-3.77 (1H, m), 4.69-4.78 (1H, m), 6.87 (1H, t), 7.23 (2H, d), 7.50 (2H, d), 7.82 (2H, m), 8.10-8.12 (3H, m) |
| 1-13 | 0.91 (3H, t), 1.73-2.12 (3H, m), 2.96 (1H, t), 3.25-3.67 (3H, m), 4.68-4.89 (1H, m), 7.22 (2H, d), 7.43 (2H, d), 7.82 (2H, d), 8.09-8.15 (3H, m) |
| 1-17 | 1.82-2.19 (4H, m), 3.34-3.43 (2H, m), 3.65-3.78 (1H, m), 4.68-4.76 (1H, m), 6.87 (1H, t), 7.34 (d, 2H), 7.51 (2H, d), 7.82 (2H, d), 8.10-8.12 (3H, m) |
| 1-18 | 1.60-2.04 (4H, m), 2.76-2.98 (2H, m), 3.19-3.32 (1H, m), 3.51-3.62 (1H, m), 4.86-4.94 (1H, m), 6.88 (1H, t), 7.14 (2H, d), 7.29 (2H, d), 7.82 (2H, d), 8.10-8.12 (3H, m) |
| 1-19 | 1.68-2.17 (4H, m), 3.36-3.48 (2H, m), 3.72-3.82 (1H, m), 4.73-4.82 (1H, m), 6.89 (1H, t), 7.24-7.35 (2H, m), 7.74-7.83 (3H, m), 8.10-8.12 (3H, m), 8.54-8.55 (1H, m) |
| 1-20 | 1.68-2.27 (4H, m), 3.33-3.48 (2H, m), 3.68-3.79 (1H, m), 4.73-4.82 (1H, m), 6.89 (1H, t), 7.49-7.88 (6H, m), 8.10-8.12 (3H, m) |
| 1-21 | 1.66-2.17 (4H, m), 3.31-3.42 (2H, m), 3.64-3.73 (1H, m), 4.69-4.77 (1H, m), 6.88 (1H, t), 7.34-7.41 (5H, m), 7.82 (2H, d), 8.10-8.12 (3H, m) |
| 1-22 | 1.08-2.51 (11H, m), 3.26-4.17 (3H, m), 6.90 (1H, t), 7.24-7.38 (5H, m), 7.81 (2H, m), 8.10-8.18 (3H, m) |
| 1-24 | 1.91-2.39 (4H, m), 3.04-3.38 (2H, m), 3.59-3.68 (1H, m), 4.52-4.63 (1H, m), 6.56 (1H, s), 6.87 (1H, t), 7.49 (1H, s), 7.83 (2H, d), 8.10-8.12 (3H, m) |
| 1-25 | 1.06 (3H, t), 1.62-2.29 (6H, m), 3.21-3.82 (3H, m), 4.68-4.99 (1H, m), 6.87 (1H, t), 7.21-7.50 (4H, m), 7.82 (2H, d), 8.11-8.13 (3H, m) |
| 1-26 | 1.67-2.18 (4H, m), 3.22-3.44 (2H, m), 3.62-3.74 (1H, m), 4.68-4.82 (1H, m), 7.33-7.40 (4H, m), 7.77 (2H, d), 8.62 (2H, d), 8.92 (1H, s) |
| 1-27 | 1.63-2.21 (4H, m), 3.23-3.71 (3H, m), 4.69-4.81 (1H, m), 7.34-7.43 (4H, m), 7.77 (2H, d), 8.02 (1H, s), 8.15 (2H, d), 8.77 (1H, s) |
| 1-29 | 1.92-2.48 (4H, m), 3.31-3.46 (2H, m), 3.68-3.78 (1H, m), 4.70-4.79 (1H, m), 6.86 (1H, t), 7.25-7.49 (3H, m), 7.82 (2H, d), 8.09-8.1 2 (3H, m) |
| 1-30 | 1.95-2.33 (4H, m), 3.27-3.69 (3H, m), 4.95-5.03 (1H, m), 7.31-7.41 (4H, m), 7.82 (2H, d), 8.10-8.13 (3H, m) |

TABLE 5-continued

| Compound No. | $^1$H-NMR (CDCl$_3$, δ ppm) |
|---|---|
| 1-31 | 1.61-2.15 (4H, m), 2.69 (3H, brs), 3.33-3.48 (2H, m), 3.70-3.81 (1H, m), 4.80-4.84 (H, m), 7.26-7.39 (m, 2H), 7.76-7.80 (3H, m), 7.95 (1H, s), 8.04 (2H, d), 8.56)1H, s) |
| 1-32 | 1.63-2.19 (4H, m), 3.22-3.3.40 (2H, m), 3.58-3.65 (1H, m), 3.68-3.80 (1H, m), 7.33-7.40 (4H, m), 7.75-8.20 (6H, m) |
| 1-33 | 1.98-2.44 (4H, m), 3.30-3.47 (2H, m), 3.68-3.79 (1H, m), 4.70-4.82 (1H, m), 6.86 (1H, t), 7.24-7.28 (1H, m), 7.44-7.48 (2H, m), 7.82 (2H, d), 8.10-8.12 (3H, m) |
| 1-34 | 1.89-2.58 (7H, m), 3.26-3.47 (3H, m), 4.16-4.56 (1H, m), 6.79 (1H, t), 7.24-7.42 (5H, m), 7.81 (2H, d), 8.04 (1H, s), 8.10 (2H, d) |
| 1-35 | 1.61-2.03 (4H, m), 2.78-2.98 (2H, m), 3.22-3.34 (1H, m), 3.48-3.61 (1H, m), 4.87-4.94 (1H, m), 7.20-7.35 (5H, m), 7.82 (2H, d), 8.10-8.12 (3H, m) |
| 1-36 | 1.78-2.23 (4H, m), 2.69 (3H, s), 3.30-3.44 (2H, m), 3.62-3.74 (1H, m), 4.72-4.76 (1H, m), 7.31-7.48 (5H, m), 7.78 (2H, d), 7.92 (1H, s), 8.04 (2H, d) |
| 1-37 | 1.82-2.37 (4H, m), 2.69 (3H, s), 3.26-3.38 (2H, m), 3.60-3.64 (1H, m), 4.97-5.03 (1H, m), 7.40-7.44 (4H, m), 7.79 (2H, d), 7.93 (1H, s), 8.05 (2H, d) |
| 1-39 | 1.65-2.18 (4H, m), 3.31-3.42 (2H, m), 3.64-3.72 (1H, m), 4.68-4.77 (1H, m), 6.88 (1H, t), 7.33-7.41 (4H, m), 7.79 (2H, d), 7.93 (1H, s), 8.05 (2H, d) |
| 1-40 | 1.68-2.19 (4H, m), 3.33-3.65 (3H, m), 4.74-4.78 (1H, m), 7.32-7.41 (4H, m), 7.54-7.73 (4H, m), 8.10 (2H, d) |
| 1-41 | 1.72-2.19 (4H, m), 3.28-3.43 (1H, m), 3.68-3.79 (2H, m), 4.61-4.74 (1H, m), 7.33-7.43 (4H, m), 7.75 (2H, d), 7.86 (2H, d), 7.91 (1H, s), 8.65 (1H, s) |
| 1-42 | 1.55-2.22 (4H, m), 3.31-3.43 (1H, m), 3.68-3..85 (2H, m), 4.67-4.78 (1H, m), 7.32-7.59 (12H, m), 7.85 (1H, s), 8.78 (1H, s) |
| 1-43 | 1.67-2.20 (4H, m), 3.22-3.42 (2H, m), 3.62-3.69 (1H, m), 4.59-4.68 (1H, m), 6.84 (1H, t), 6.93-7.02 (2H, m), 7.39-7.44 (2H, m), 7.76 (2H, d), 8.04-8.11 (3H, m) |
| 1-44 | 1.79-2.42 (4H, m), 3.29-3.44 (2H, m), 3.68-3.76 (1H, m), 4.69-4.76 (1H, m), 6.86 (1H, t), 7.04-7.49 (4H, m), 7.82 (2H, d), 8.10-8.15 (3H, m) |
| 1-45 | 1.89-2.32 (4H, m), 2.62 (3H, s), 3.30-3.50 (2H, m), 3.70-3.81 (1H, m), 4.58-4.67 (1H, m), 6.86 (1H, t), 7.19-7.35 (4H, m), 7.82 (2H, d), 8.09-8.12 (3H, m) |
| 1-46 | 1.88-2.53 (4H, m), 3.31-3.44 (2H, m), 3.67-3.78 (1H, m), 4.72-4.79 (1H, m), 6.94 (1H, t), 7.22-7.34 (2H, m), 7.55 (1H, s), 7.82 (2H, d), 8.10-8.12 (3H, m) |
| 1-47 | 1.88-2.30 (4H, m), 3.38-3.76 (3H, m), 4.61-4.71 (1H, m), 6.87 (1H, t), 7.36 (1H, s), 7.76 (1H, s), 7.82 (2H, d), 8.11-8.14 (3H, m) |
| 1-48 | 1.76-2.18 (4H, m), 2.69 (3H, s), 3.32-3.42 (2H, m), 3.62-3.73 (1H, m), 4.70-4.81 (1H, m), 7.05-7.10 (2H, m), 7.42-7.49 (2H, m), 7.78 (2H, d), 7.92 (1H, s), 8.04 (2H, d) |
| 1-49 | 1.88-2.31 (4H, m), 2.68 (3H, s), 3.39-3.72 (3H, m), 4.62-4.73 (1H, m), 7.34 (1H, s), 7.73-8.05 (6H, m) |
| 1-50 | 1.82-2.14 (2H, m), 2.48-2.74 (2H, m), 3.08-3.48 (3H, m), 3.70 (3H, s), 4.43-4.72 (1H, m), 6.81 (1H, t), 7.26-7.40 (4H, m), 7.82 (H, d), 8.05 (1H, s), 8.10 (2H, d) |
| 1-51 | 2.38-2.61 (4H, m), 3.36-3.39 (2H, m), 3.65-3.78 (1H, m), 4.00-4.11 (1H, m), 6.83 (1H, t), 7.18-7.36 (10H, m), 7.81 (2H, d), 8.03 (1H, s), 8.10 (2H, d) |
| 1-53 | 1.85-2.19 (4H, m), 3.05-3.65 (3H, m), 4.15-4.49 (2H, m), 6.25 (1H, s), 6.84 (1H, t), 7.40-7.51 (2H, m), 7.82 (2H, d), 8.09-8.12 (3H, m) |
| 1-54 | 1.90-2.39 (4H, m), 3.10-3.69 (3H, m), 4.49-4.56 (1H, m), 4.69-4.91 (1H, m), 6.83 (1H, t), 7.83-8.18 (7H, m) |
| 1-55 | 1.88-2.36 (4H, m), 3.19-3.48 (2H, m), 4.69-4.81 (1H, m), 7.32-7.58 (4H, m), 7.80-7.91 (2H, m), 8.13-8.19 (3H, m) |
| 1-57 | 1.82-2.39 (7H, m), 2.67 (3H, s), 3.16-3.51 (3H, m), 4.61-4.78 (1H, m), 7.25-737 (4H, m), 7.79 (2H, d), 7.90 (1H, s), 8.04 (2H, d) |
| 1-58 | 1.34-2.18 (10H, m), 3.13-3.69 (4H, m), 4.71-4.80 (1H, m), 7.35-7.44 (4H, m), 7.87 (1H, s), 8.10 (2H, d) |
| 1-61 | 1.16 (3H, t), 1.66-2.28 (4H, m), 2.68 (3H, s), 2.99-3.33 (4H, m), 3.58-3.65 (1H, m), 4.65-4.73 (1H, m), 7.30-7.38 (4H, m), 7.78 (2H, d), 7.89 (1H, s), 8.04 (2H, d) |
| 1-62 | 1.89-2.19 (4H, m), 3.25-3.70 (3H, m), 4.78-4.84 (1H, m), 7.28-7.38 (4H, m), 7.82 (2H, d), 8.10-8.12 (3H, m) |
| 1-63 | 1.80-2.22 (4H, m), 2.69 (3H, s), 3.24-3.65 (3H, m), 4.81-4.89 (1H, m), 7.30-7.41 (4H, m), 7.79 (2H, d), 7.93 (1H, s), 8.05 (2H, d) |
| 1-64 | 1.65-2.09 (4H, m), 2.66-2.94 (5H, m), 3.20-3.29 (1H, m), 3.53-3.61 (1H, m), 4.89-4.98 (1H, m), 7.13-7.31 (4H, m), 7.78 (2H, d), 7.95 (1H, s), 8.04 (2H, d) |
| 1-65 | 1.37 (3H, t), 1.74-2.18 (4H, m), 2.88-3.02 (2H, m), 3.31-3.43 (2H, m), 3.60-3.71 (1H, m), 4.70-4.79 (1H, m), 7.33-7.43 (4H, m), 7.78 (2H, d), 7.90 (1H, s), 8.07 (2H, d) |

TABLE 5-continued

| Compound No. | $^1$H-NMR (CDCl$_3$, δ ppm) |
|---|---|
| 1-67 | 1.70-2.39 (4H, m), 2.46 (3H, s), 3.02-3.38 (3H, m), 3.52-3.68 (1H, m), 4.70-4.80 (1H, m), 6.72-6.99 (2H, m), 7.89 (2H, d), 8.10-8.21 (3H, m) |
| 1-70 | 1.95-2.32 (4H, m), 3.20-3.69 (6H, m), 3.95-4.05 (1H, m), 4.35 (1H, m), 6.93 (1H, t), 7.91-8.45 (6H, m) |
| 1-72 | 1.95-2.33 (4H, m), 3.28-3.36 (1H, m), 3.56-3.73 (2H, m), 4.92-5.01 (1H, m), 6.88 (1H, t), 7.09-7.15 (2H, m), 7.43-7.50 (2H, m), 7.82 (2H, d), 8.10-8.13 (3H, m) |
| 1-73 | 1.85-2.36 (4H, m), 2.69 (3H, s), 3.28-3.38 (1H, m), 3.59-3.66 (2H, m), 4.97-5.03 (1H, m), 7.11-7.16 (2H, m), 7.42-7.50 (2H, m), 7.79 (2H, d), 7.93 (1H, s), 8.05 (2H, d) |
| 1-75 | 0.84-2.68 (14H, m), 3.19-3.53 (3H, m), 4.69-4.76 (1H, m), 7.25-7.36 (4H, m), 7.79 (2H, d), 7.91 (1H, s), 8.04 (2H, d) |
| 1-79 | 1.58-2.20 (4H, m), 3.31-3.42 (2H, m), 3.63-3.73 (1H, m), 4.68-4.74 (1H, m), 6.87 (1H, t), 7.33-8.11 (9H, m) |
| 1-80 | 1.62-2.18 (4H, m), 3.31-3.42 (2H, m), 3.62-3.72 (1H, m), 4.68-4.74 (1H, m), 7.31-7.56 (7H, m), 7.97-8.06 (3H, m) |
| 1-81 | 1.62-2.21 (4H, m), 3.24-3.72 (3H, m), 4.10 (3H, s), 4.60-4.73 (1H, m), 7.34-7.50 (7H, m), 7.94 (2H, d) |
| 1-82 | 1.73-2.22 (4H, m), 3.26-3.71 (3H, m), 4.10 (3H, s), 4.67-4.74 (2H, m), 7.35-7.53 (7H, m), 7.93-8.00 (3H, m) |
| 1-83 | 1.68-2.23 (4H, m), 3.29-3.49 (2H, m), 3.69-3.80 (1H, m), 4.71-4.78 (1H, m), 6.88 (1H, t), 7.79-7.91 (3H, m), 8.11-8.19 (3H, m), 8.48 (1H, m), 8.48 (1H, m), 8.68 (1H, m) |
| 1-84 | 1.63-2.21 (4H, m), 3.31-3.43 (2H, m), 3.64-3.72 (1H, m), 4.67-4.78 (1H, m), 6.94 (1H, t), 7.31-7.40 (6H, m), 8.04-8.07 (3H, m) |
| 1-95 | 1.62-2.1 5 (4H, m), 2.44 (3H, s), 3.31-3.42 (2H, m), 3.62-3.71 (1H, m), 4.68-4.76 (1H, m), 6.84 (1H, t), 7.34-7.42 (6H, m), 7.90 (2H, d), 8.03 (1H, s) |
| 1-96 | 1.67-2.18 (4H, m), 3.30-3.42 (2H, m), 3.60-3.72 (1H, m), 3.89 (3H, s), 4.67-4.74 (1H, m), 6.83 (1H, t), 7.05 (2H, d), 7.32-7.43 (4H, m), 8.01-8.04 (3H, m) |
| 1-97 | 1.63-2.20 (4H, m), 3.29-3.43 (2H, m), 3.65-3.74 (1H, m), 4.68-4.77 (1H, m), 6.88 (1H, t), 7.32-7.43 (4H, m), 7.85 (2H, d), 8.11-8.13 (3H, m) |
| 1-98 | 1.64-2.18 (4H, m), 3.28-3.41 (2H, m), 3.58-3.72 (1H, m), 4.62-4.76 (1H, m), 6.84 (1H, t), 7.31-7.61 (6H, m), 7.86 (1H, s), 8.06 (1H, s) |
| 1-99 | 1.64-2.19 (4H, m), 3.28-3.42 (2H, m), 3.63-3.73 (1H, m), 4.68-4.77 (1H, m), 6.86 (1H, t), 7.31-7.64 (5H, m), 7.86-8.11 (3H, m) |
| 1-100 | 1.70-2.21 (4H, m), 3.28-3.73 (3H, m), 4.51-4.69 (1H, m), 7.31-7.64 (9H, m) |
| 1-101 | 1.15-1.26 (6H, m), 1.80-2.09 (4H, m), 2.51-2.71 (4H, m), 3.31-3.91 (3H, m), 4.48-4.58 (1H, m), 7.24-7.41 (4H, m), 7.78-8.11 (5H, m) |
| 1-104 | 1.64-2.22 (4H, m), 2.50 (3H, s), 3.28-3.59 (3H, m), 4.72-4.83 (1H, m), 7.05 (1H, s), 7.31-7.45 (6H, m), 7.89 (2H, d) |
| 1-105 | 1.15-2.22 (9H, m), 3.33-3.77 (3H, m), 4.75-4.82 (1H, m), 7.32-7.44 (4H, m), 7.76 (2H, d), 7.90 (1H, s), 8.01 (2H, d) |
| 1-106 | 1.66-2.27 (4H, m), 2.67 (3H, s), 2.99 (3H, s), 3.21-3.35 (2H, m), 3.54-3.62 (1H, m), 4.68-4.74 (1H, m), 7.24 (2H, d), 7.78 (2H, d), 7.89 (1H, s), 8.04 (2H, d) |
| 1-107 | 1.71-2.31 (4H, m), 2.68 (3H, s), 3.02 (3H, s), 3.23-3.38 (2H, m), 3.57-3.65 (1H, m), 4.71-4.79 (1H, m), 7.50 (2H, d), 7.66 (2H, d), 7.90 (1H, s), 8.04 (2H, d) |
| 1-108 | 1.67-2.21 (4H, m), 3.29-3.65 (3H, m), 3.99 (3H, s), 4.70-4.81 (2H, m), 7.25-7.41 (5H, m), 7.72 (2H, d), 8.07 (2H, d), 8.46-8.53 (1H, m) |
| 1-114 | 1.69-2.29 (4H, m), 2.68 (3H, s), 2.98 (3H, s), 3.22-3.34 (2H, m), 3.53-3.62 (1H, m), 4.68-4.75 (1H, m), 7.05-7.10 (2H, m), 7.31-7.38 (2H, m), 7.78 (2H, d), 7.89 (1H, s), 8.04 (2H, d) |
| 1-120 | 1.61-2.19 (4H, m), 2.44 (3H, s), 3.31-3.67 (3H, m), 4.69-4.78 (1H, m), 6.82 (1H, t), 7.34-7.76 (9H, m) |
| 1-121 | 1.70-2.18 (7H, m), 2.64 (3H, s), 3.31-3.43 (2H, m), 3.58-3.68 (1H, m), 4.72-4.80 (1H, m), 7.32-7.43 (4H, m), 7.66-7.78 (5H, m) |
| 1-122 | 1.67-2.27 (4H, m), 2.66 (3H, s), 2.98 (3H, s), 3.20-3.34 (2H, m), 3.51-3.62 (1H, m), 4.67-4.73 (1H, m), 7.01-7.09 (2H, m), 7.30-7.41 (4H, m), 7.87 (1H, s), 7.98 (2H, d) |
| 1-123 | 1.31-1.42 (3H, m) 1.66-2.29 (3H, m), 2.88-3.01 (5H, m), 3.21-3.35 (2H, m), 3.49-3.61 (1H, m), 4.68-4.74 (1H, m), 7.01-7.10 (2H, m), 7.81 (2H, d), 8.01-8.11 (3H, m) |
| 1-124 | 1.88-2.49 (4H, m), 2.71 (3H, d), 3.24-3.32 (1H, m), 3.56-3.81 (2H, m), 5.13-5.21 (1H, m), 6.79 (1H, t), 7.29-7.44 (5H, m), 7.81 (2H, d), 8.01-8.11 (3H, m) |
| 1-125 | 1.63-1.71 (1H, m), 2.15-3.03 (9H, m), 3.14-3.38 (2H, m), 3.74-3.83 (1H, m), 4.69-4.74 (1H, m), 6.83 (1H, t), 7.21-7.40 (5H, m), 7.82 (2H, d), 8.06-8.12 (3H, m) |
| 1-132 | 1.66-2.19 (4H, m), 3.31-3.44 (2H, m), 3.66-3.76 (1H, m), 4.69-4.77 (1H, m), 6.87 (1H, t), 7.33-7.44 (4H, m), 7.51-7.79 (3H, m), 8.10 (1H, s) |

TABLE 5-continued

| Compound No. | $^1$H-NMR (CDCl$_3$, δ ppm) |
|---|---|
| 1-133 | 1.67-2.19 (4H, m), 3.29-3.44 (2H, m), 3.67-3.77 (1H, m), 4.69-4.78 (1H, m), 6.86 (1H, t), 7.32-7.44 (4H, m), 7.59-7.72 (2H, m), 7.90 (1H, s), 8.10 (1H, s) |
| 1-134 | 1.68-2.18 (4H, m), 3.33-3.43 (2H, m), 3.64-3.75 (1H, m), 3.95 (3H, s), 4.68-4.78 (1H, m), 6.85 (1H, t), 7.24-7.43 (6H, m), 7.59 (1H, d), 8.03 (1H, s) |
| 1-136 | 1.65-2.20 (4H, m), 3.27-3.43 (2H, m), 3.65-3.75 (1H, m), 4.68-4.77 (1H, m), 6.99 (1H, t), 7.33-7.43 (4H, m), 8.08 (1H, s), 8.14 (1H, s), 8.46 (2H, s) |
| 1-138 | 1.75-2.18 (4H, m), 2.68 (3H, s), 3.31-3.42 (2H, m), 3.61-3.69 (1H, m), 4.71-4.78 (1H, m), 7.05-7.10 (2H, m), 7.35-7.48 (4H, m), 7.89 (1H, s), 7.99 (2H, d) |
| 1-141 | 1.69-2.30 (4H, m), 2.35 (3H, s), 2.67 (3H, s), 2.99 (3H, s), 3.24-3.34 (2H, m), 3.53-3.62 (1H, m), 4.65-4.72 (1H, m), 7.18-7.27 (4H, m), 7.78 (2H, d), 7.89 (1H, s), 8.04 (2H, d) |
| 1-142 | 1.68-2.30 (4H, m), 2.35 (3H, s), 2.66 (3H, s), 2.99 (3H, s), 3.25-3.32 (2H, m), 3.54-3.62 (1H, m), 4.64-4.70 (1H, m), 7.18-7.37 (6H, m), 7.87 (1H, s), 7.99 (1H, d) |
| 1-143 | 1.55-2.09 (4H, m), 2.33 (3H, s), 2.63-3.00 (5H, m), 3.19-3.30 (1H, m), 3.50-3.59 (1H, m), 4.90-4.98 (1H, m), 7.08-7.16 (4H, m), 7.78 (2H, d), 7.94 (1H, s), 8.04 (2H, d) |
| 1-144 | 1.53-2.08 (4H, m), 2.33 (3H, s), 2.62-2.98 (5H, m), 3.19-3.28 (1H, m), 3.50-3.58 (1H, m), 4.89-4.98 (1H, m), 7.07-7.16 (4H, m), 7.36 (2H, d), 7.86 (1H, s), 7.99 (2H, d) |
| 1-153 | 1.68-2.21 (4H, m), 3.31-3.48 (2H, m), 3.71-3.80 (1H, m), 6.88 (1H, t), 7.12-7.40 (3H, m), 7.88 (2H, d), 8.09-8.18 (3H, m) |
| 1-154 | 1.72-2.18 (4H, m), 2.70 (3H, s), 3.38-3.49 (2H, m), 3.69-3.78 (1H, m), 4.78-4.88 (1H, m), 7.09-7.39 (3H, m), 7.87 (2H, d), 7.94 (1H, s), 8.08 (2H, d) |
| 1-157 | 1.62-2.19 (4H, m), 3.29-3.43 (2H, m), 3.65-3.74 (1H, m), 4.68-4.76 (1H, m), 6.88 (1H, t), 7.32-7.43 (4H, m), 7.87-8.12 (4H, m) |
| 1-164 | 1.61-2.24 (7H, m), 2.85-3.54 (4H, m), 3.71 (3H, s), 4.69-4.75 (1H, m), 5.83 (1H, s), 6.82 (1H, t), 7.81 (2H, d), 8.07-8.12 (3H, m) |
| 1-165 | 1.65-2.22 (7H, m), 2.79-3.30 (4H, m), 3.76 (3H, s), 4.81-4.90 (1H, m), 5.83 (1H, s), 6.83 (1H, t), 7.82 (2H, d), 8.08-8.14 (3H, m) |
| 1-168 | 1.65-2.22 (4H, m), 3.39-3.48 (2H, m), 3.69-3.78 (1H, m), 4.69-4.80 (1H, m), 6.88 (1H, t), 7.55-7.70 (4H, m), 7.87 (2H, d), 8.08-818 (3H, m) |
| 1-169 | 1.50-2.18 (4H, m), 2.77-3.56 (4H, m), 3.87 (3H, s), 4.72-4.84 (1 H, m), 6.83 (1H, t), 7.19 (1H, s), 7.34 (1H, s), 7.82 (2H, d), 8.08-8.12 (3H, m) |
| 1-170 | 1.53-2.21 (4H, m), 2.91-3.59 (4H, m), 3.85 (3H, s), 4.69-4.81 (1H, m), 6.05 (1H, s), 6.84 (1H, t), 7.28 (1H, s), 8.82 (2H, d), 8.08-8.19 (3H, m) |
| 1-171 | 4 (4H, m), 2.88-3.60 (4H, m), 3.85 (3H, s), 4.82-4.93 (1H, m), 6.05 (1H, s), 6.83 (1H, t), 7.41 (1H, s), 7.82 (2H, d), 8.10-8.14 (3H, d) |
| 2-3 | 1.98-2.46 (4H, m), 3.28-3.78 (3H, m), 4.62-4.72 (1H, m), 7.05 (1H, d), 7.23-7.89 (9H, m), 8.30 (1H, s) |
| 2-4 | 1.62-2.05 (4H, m), 2.76-3.59 (3H, m), 4.89-4.99 (1H, m), 7.11 (2H, d), 7.22-7.33 (4H, m), 7.71 (2H, d), 8.16 (1H, s), 8.23 (1H, s) |
| 2-5 | 1.55-2.17 (4H, m), 3.23-3.62 (3H, m), 3.66-3.79 (1H, m), 7.16-7.69 (11H, m) |
| 2-6 | 1.70-2.19 (4H, m), 3.23-3.78 (3H, m), 4.54-4.71 (1H, m), 7.25-7.40 (6H, m), 7.69 (2H, d), 7.92 (1H, s), 8.10 (1H, s) |
| 2-9 | 1.69-2.20 (4H, m), 3.35-3.79 (3H, m), 4.58-4.69 (1H, m), 7.06 (1H, d), 7.23-7.40 (6H, m), 7.58-7.88 (3H, m), 8.24 (1H, s) |
| 2-10 | 1.73-2.21 (4H, m), 3.33-3.40 (1H, m), 3.52-3.78 (2H, m), 3.87 (3H, s), 4.68-4.76 (1H, m), 7.23-7.39 (6H, m), 7.67 (2H, d), 8.50 (1H, s) |
| 2-11 | 1.63-2.22 (4H, m), 3.23-3.63 (3H, m), 3.92 (3H, s), 4.68-4.76 (1H, m), 6.50 (1H, s), 7.22-7.42 (6H, m), 7.65 (2H, d), 7.97 (1H, s) |
| 2-12 | 1.68-2.18 (4H, m), 2.42 (3H, s), 3.28-3.46 (2H, m), 3.50-3.62 (1H, m), 4.69-4.78 (1H, m), 6.77 (1H, d), 7.21-7.38 (7H, m), 7.56 (1H, s), 7.63 (1H, d) |
| 3-1 | 1.81-2.15 (4H, m), 3.38-3.48 (2H, m), 4.66-4.74 (1H, m), 4.93 (2H, s), 6.88 (1H, t), 7.28-7.31 (4H, m), 7.82 (2H, d), 8.10-8.12 (3H, m) |
| 3-2 | 1.80-2.46 (6H, m), 2.87 (0.5H, d), 3.32 (0.5H, d), 4.04-4.10 (1H, m), 5.09-5.22 (1H, m), 6.25-6.50 (1H, m), 6.71-7.03 (1H, m), 7.23-7.34 (4H, m), 7.82 (2H, d), 8.07-8.13 (3H, m) |
| 3-3 | 2.25-2.54 (2H, m)< 3.48-4.14 (4H, m), 6.88 (1H, t), 7.30-7.49 (4H, m), 7.78-7.84 (2H, m), 8.08-8.21 (3H, m) |
| 3-6 | 1.63-2.18 (4H, m), 3.31-3.43 (2H, m), 3.62-3.72 (1H, m), 4.68-4.77 (1H, m), 6.85 (1H, t), 6.90 (1H, d), 7.32-7.42 (4H, m), 8.04 (1H, s), 8.24 (1H, d), 8.88 (1H, s) |
| 3-7 | 1.62-2.19 (4H, m), 3.22-3.71 (3H, m), 4.12 (3H, s), 4.68-4.73 (1H, m), 6.85 (1H, t), 7.35-7.43 (4H, m), 8.10 (1H, s), 9.22 (2H, s) |
| 3-10 | 1.65-2.17 (4H, m), 3.30-3.41 (2H, m), 3.59-3.67 (1H, m), 4.00 (3H, s), 4.67-4.74 (1H, m), 6.78 (1H, t), 7.32-7.42 (4H, m), 7.92 (1H, s), 8.36 (1H, s), 8.38 (1H, s) |

TABLE 5-continued

| Compound No. | $^1$H-NMR (CDCl$_3$, δ ppm) |
|---|---|
| 1-177 | 1.91-2.48 (4H, m), 2.85-3.49 (2H, m), 3.85-3.90 (1H, m), 4.32-4.49 (1H, m), 4.90-5.03 (1H, m), 6.73 (1H, t), 7.78-8.24 (7H, m) |
| 1-178 | 1.62-1.94 (4H, m), 2.26 (3H, s), 2.37 (3H, s), 2.60-3.61 (4H, m), 4.88-4.97 (1H, m), 7.82 (2H, d), 8.09-8.12 (3H, m) |
| 1-179 | 1.75-2.19 (4H, m), 2.92-3.64 (7H, m), 4.11 (3H, s), 4.66-4.82 (1H, m), 6.84 (1H, t), 7.81 (2H, d), 8.10-8.12 (3H, m) |
| 1-180 | 1.72-2.72 (7H, m), 3.11-4.21 (7H, m), 4.78-4.85 (1H, m), 6.83 (1H, t), 7.82 (2H, d), 8.10-8.12 (3H, m) |
| 1-181 | 1.81-2.19 (4H, m), 2.76-3.54 (4H, m), 4.74-4.88 (1H, m), 6.31 (1H, s), 6.82 (1H, t), 7.38 (1H, s), 7.82 (2H, d), 8.08-8.12 (3H, m) |
| 1-182 | 1.69-2.08 (4H, m), 2.81-3.00 (2H, m), 3.24-3.61 (2H, m), 4.89-4.98 (1H, m), 6.88 (1H, t), 7.24-7.29 (1H, m), 7.82 (2H, d), 8.10-8.13 (3H, m), 8.49-8.51 (2H, m) |
| 1-183 | 1.61-1.93 (4H, m), 2.82-3.65 (4H, m), 4.91-4.98 (1H, m), 6.84-6.93 (2H, m), 7.59-7.64 (1H, m), 7.82 (2H, d), 8.09-8.15 (4H, m) |
| 1-184 | 1.65-2.12 (4H, m), 2.49-3.72 (4H, m), 4.89-4.98 (1H, m), 6.74-7.05 (3H, m), 7.82 (2H, d), 8.10-8.15 (4H, m) |
| 1-185 | 1.66-2.11 (4H, m), 2.82-3.63 (4H, m), 4.95-4.98 (1H, m), 6.88 (1H, t), 7.82 (2H, d), 8.10-8.12 (3H, m), 8.61 (2H, s), 9.13 (1H, s) |
| 1-186 | 1.88-2.26 (H, m), 3.16-3.62 (4H, m), 4.86-4.92 (1H, m), 6.84 (1H, t), 7.18 (1H, t), 7.82 (2H, d), 8.10-8.12 (3H, m), 8.70 (2H, d) |
| 1-188 | 1.65-2.19 (4H, m), 3.30-3.75 (3H, m), 4.36-4.75 (1H, m), 6.86 (1H, t), 7.34-7.42 (4H, m), 7.83 (2H, d), 8.04-8.09 (3H, m) |
| 1-189 | 1.73-2.18 (4H, m), 2.68 (3H, m), 3.30-3.72 (3H, m), 4.71-4.78 (1H, m), 7.34-7.42 (4H, m), 7.79-7.99 (5H, m) |
| 1-193 | 1.88-2.32 (7H, m), 3.08-3.33 (2H, m), 3.64-3.72 (1H, m), 4.22-4.31 (1H, m), 4.78-4.87 (1H, m), 6.02 (1H, s), 6.83 (1H, t), 7.43 (1H, s), 7.82 (2H, d), 8.10-8.12 (3H, m) |
| 1-194 | 1.93-2.32 (7H, m), 3.01-3.63 (3H, m), 4.28-4.35 (1H, m), 4.78-4.89 (1H, m), 6.04 (1H, s), 6.84 (1H, t), 7.31 (1H, s), 7.82 (2H, d), 8.10-8.12 (3H, m) |
| 1-207 | 1.72-2.12 (4H, m), 2.31 (3H, s), 2.94-3.62 (4H, m), 4.85-4.93 (1H, m), 6.86 (1H, t), 7.05 (1H, d), 7.45 (1H, d), 7.81 (2H, d), 8.09-8.12 (3H, m), 8.37 (1H, s) |
| 1-208 | 1.72-2.18 (4H, m), 2.31 (3H, s), 2.63-3.63 (7H, m), 4.88-4.93 (1H, m), 7.07 (1H, d), 7.47 (1H, d), 7.78 (2H, d), 7.98 (1H, s) < 8.04 (2H, d), 8.37 (1H, s) |
| 1-210 | 1.78-2.17 (4H, m), 2.94-3.63 (4H, m), 4.86-4.91 (1H, m), 6.84 (1H, t), 7.21 (1H, d), 7.82 (2H, d) < 8.10-8.12 (3H, m), 8.68 (1H, d), 9.16 (1H, s) |
| 1-212 | 1.78-2.13 (4H, m), 2.26 (3H, s), 2.92-3.59 (3H, m), 4.23-4.33 (1H, m), 4.82-4.89 (1H, m), 6.82 (1H, t), 7.82 (2H, d), 8.10-8.12 (3H, m) |
| 1-213 | 1.80-2.30 (7H, m), 2.68 (3H, s), 3.03-3.61 (4H, m), 4.80-4.90 (1H, m), 7.78 (2H, d), 7.96 (1H, s), 8.04 (2H, d), 8.52 (2H, s) |
| 1-214 | 2.14-2.51 (4H, m), 2.65 (3H, s), 3.38-3.69 (3H, m), 4.76-4.89 (1H, m), 6.83 (1H, t), 7.82 (2H, d), 8.10-8.12 (3H, m) |
| 1-215 | 2.08-2.51 (4H, m), 2.65 (3H, s), 2.68 (3H, s), 3.40-3.62 (3H, m), 4.69-4.82 (1H, m), 7.79 (2H, d), 7.91 (1H, s), 8.05 (2H, d) |
| 1-216 | 1.69-2.29 (4H, m), 2.66 (3H, s), 2.99 (3H, s), 3.25-3.65 (3H, m), 3.92 (3H, s), 4.67-4.74 (1H, m), 7.04-7.87 (8H, m) |
| 1-217 | 1.77-2.16 (4H, m), 2.23 (3H, s), 3.05-3.59 (4H, m), 4.66-4.78 (1H, m), 6.85 (1H, t), 7.36 (1H, s), 7.82 (2H, d), 8.09-8.13 (3H, m) |
| 1-229 | 1.73-2.22 (4H, m), 2.57 (3H, s), 3.02-3.29 (3H, m), 3.53-3.62 (1H, m), 5.76 (2H, m), 6.79 (1H, t), 7.72-7.99 (5H, m) |
| 1-231 | 1.83-2.22 (4H, m), 2.70 (6H, s), 3.01-3.67 (4H, m), 4.84-4.93 (1H, m), 7.23-7.31 (2H, m), 7.78 (2H, d), 7.93 (1H, s), 8.04 (2H, d) |
| 1-232 | 1.88-2.25 (4H, m), 3.05-3.65 (4H, m), 3.75-3.82 (1H, m), 6.86 (1H, t), 7.82 (2H, d), 8.10-8.12 (3H, m), 8.55 (2H, s) |
| 1-233 | 1.81-2.26 (4H, m), 2.71 (3H, s), 3.02-3.66 (4H, m), 4.80-4.87 (1H, m), 7.78 (2H, d), 7.92 (1H, s), 8.04 (2H, d), 8.55 (2H, s) |
| 1-234 | 1.25 (3H, s), 1.65-2.55 (4H, m), 3.22-3.46 (4H, m), 6.79 (1H, t), 7.24-7.35 (4H, m), 7.82 (2H, d), 8.06 (1H, s), 8.12 (2H, d) |
| 1-235 | 1.25 (3H, s), 1..62-2.72 (7H, m), 3.16-3.45 (4H, m), 7.23-7.35 (4H, m), 7.78 (2H, d), 7.91 (1H, s), 8.03 (2H, d) |
| 1-245 | 1.86-2.19 (4H, m), 2.70 (6H, s), 3.02-3.66 (4H, m), 4.86-4.93 (1H, m), 7.21-7.29 (2H, m), 7.82 (2H, d), 7.95 (1H, s), 8.07 (2H, d) |
| 1-246 | 1.80-2.30 (7H, m), 2.67 (3H, s), 3.01-3.59 (4H, m), 4.79-4.84 (1H, m), 7.82 (2H, d), 7.96 (1H, s), 8.05 (2H, d), 8.51 (2H, s) |
| 1-248 | 1.70-2.18 (4H, m), 2.67 (3H, s), 2.88-3.62 (4H, m), 3.85 (3H, s), 4.88-4.92 (1H, m), 6.04 (1H, s), 7.41 (1H, s), 7.78 (2H, d), 7.94 (1H, s), 8.04 (2H, d) |
| 1-251 | 1.73-2.10 (4H, m), 2.35 (3H, s), 3.35-3.81 (4H, m), 4.75-4.81 (1H, m), 6.86 (1H, t), 7.52-7.61 (1H, m), 7.80-7.84 (3H, m), 8.10-8.15 (3H, m), 8.36 (1H, s) |
| 1-252 | 1.99-2.21 (4H, m), 2.34 (3H, s), 3.06 (3H, s), 3.30-3.59 (3H, m), 4.50-4.59 (1H, m), 6.83 (1H, t), 7.36-7.55 (2H, m), 7.82 (2H, d), 8.09-81.2 (3H, m), 8.41 (1H, s) |

TABLE 5-continued

| Compound No. | $^1$H-NMR (CDCl$_3$, δ ppm) |
|---|---|
| 1-253 | 1.99-2.24 (4H, m), 2.34 (3H, s), 2.68 (3H, s), 3.06 (3H, s), 3.31-3.58 (3H, m), 4.54-4.61 (1H, m), 7.37-7.55 (2H, m), 7.78 (2H, d), 7.93 (1H, s), 8.03 (2H, d), 8.40 (1H, s) |
| 1-255 | 1.68-2.19 (4H, m), 3.21-3.74 (3H, m), 3.65-3.81 (1H, m), 7.35-7.42 (6H, m), 8.08-8.14 (3H, m) |
| 1-260 | 1.64-2.15 (4H, m), 3.29-3.66 (3H, m), 4.06 (3H, s), 4.81-4.85 (1H, m), 7.34-7.63 (8H, m) |
| 1-261 | 1.69-2.18 (4H, m), 2.51 (3H, s), 3.32-3.73 (3H, m), 4.73-4.82 (1H, m), 734-7.57 (8H, m) |
| 1-262 | 1.70-2.18 (4H, m), 2.31 (3H, s), 2.53 (3H, s), 3.30-3.67 (3H, m), 3.75-3.81 (1H, m), 7.33-7.72 (8H, m) |
| 1-263 | 1.79-2.23 (4H, m), 2.58 (3H, s), 3.15-3.59 (4H, m), 4.57-4.78 (1H, m), 6.83 (1H, t), 7.67-7.84 (2H, m), 8.08-8.24 (3H, m) |
| 1-264 | 1.75-2.22 (4H, m), 2.58 (3H, s), 3.05-3.61 (4H, m), 4.55-4.65 (1H, m), 6.80 (1H, t), 7.45-8.08 (5H, m) |
| 1-265 | 1.77-2.25 (4H, m), 2.58 (3H, s), 3.07-3.59 (4H, m), 4.52-4.73 (1H, m), 6.81 (1H, t), 7.20-7.25 (2H, m), 8.01-8.10 (3H, m) |
| 1-266 | 1.79-2.22 (4H, m), 2.57 (3H, s), 3.07-3.58 (4H, m), 4.52-4.65 (1H, m), 6.80 (1H, t), 7.31-7.39 (1H, m), 7.81-7.92 (2H, m), 8.05 (1H, s) |
| 1-267 | 1.82-2.24 (4H, m), 2.30 (3H, s), 3.04-3.59 (4H, m), 4.74-4.81 (1H, m), 6.83 (1H, t), 7.85 (2H, d), 8.10-8.13 (3H, m), 8.51 (2H, s) |
| 1-268 | 1.82-2.24 (4H, m), 2.29 (3H, s), 3.03-3.58 (4H, m), 4.75-4.82 (1H, m), 6.84 (1H, t), 7.65-8.24 (5H, m), 8.52 (2H, s) |
| 1-269 | 1.81-2.19 (4H, m), 3.33-3.72 (3H, m), 4.69-4.80 (1H, m), 6.89 (1H, t), 7.32-7.43 (4H, m), 7.93-8.25 (7H, m), 8.99 (1H, m) |
| 1-271 | 1.82-2.22 (4H, m), 2.29 (3H, s), 3.07-3.61 (4H, m), 4.76-4.82 (1H, m), 6.81 (1H, t), 7.51-8.08 (5H, m), 8.51 (2H, s) |
| 1-272 | 1.84-2.23 (4H, m), 2.29 (3H, s), 3.06-3.59 (4H, m), 4.74-4.81 (1H, m), 6.81 (1H, t), 7.23-7.25 (2H, m), 8.01-8.03 (3H, m), 8.51 (2H, s) |
| 1-274 | 1.75-2.21 (4H, m), 2.57 (3H, s), 3.02-3.75 (4H, m), 4.59-4.80 (1H, m), 7.22-7.53 (4H, m), 8.21 (1H, s), 8.75 (1H, s) |
| 1-275 | 1.77-2.21 (4H, m), 2.57 (3H, s), 2.59 (3H, s), 3.03-3.61 (4H, m), 4.59-4.70 (1H, m), 7.23 (2H, d), 7.54 (2H, d), 8.16 (1H, s) |
| 1-276 | 1.79-2.23 (4H, m), 2.58 (3H, s), 3.06-3.61 (4H, m), 4.59-4.72 (1H, m), 7.26 (2H, d), 7.51 (2H, d), 8.27 (1H, s) |
| 1-277 | 1.79-2.23 (4H, m), 2.57 (3H, s), 3.02-3.64 (4H, m), 4.57-4.73 (1H, m), 7.255 (2H, d), 7.41 (1H, s), 7.51 (2H, d), 7.87 (1H, s), 8.31 (1H, s) |
| 1-278 | 1.80-2.22 (4H, m), 2.46 (3H, s), 2.57 (3H, s), 3.05-3.72 (4H, m), 4.56-4.73 (1H, m), 6.94 (1H, t), 7.25 (2H, d), 7.51 (2H, d), 8.30 (1H, s) |
| 1-279 | 1.80-2.23 (4H, m), 2.58 (3H, s), 3.08-3.59 (4H, m), 4.54-4.71 (1H, m), 6.84 (1H, t), 8.14 (1H, s), 8.21-8.30 (4H, m) |
| 1-284 | 1.32 (3H, s), 1.63-2.28 (4H, m), 3.14-4.14 (4H, m), 7.20-7.33 (4H, m), 7.82 (2H, d), 8.05 (1H, s), 8.13 (2H, d) |
| 1-285 | 1.76-2.21 (4H, m), 2.57 (3H, s), 3.06-3.53 (4H, m), 3.54-3.69 (1H, m), 7.43-8.14 (5H, m) |
| 1-286 | 1.77-2.22 (4H, m), 2.58 (3H, s), 2.63 (3H, s), 3.07-3.64 (4H, m), 3.71 (3H, s), 4.64-4.76 (1H, m), 7.61 (2H, d), 7.69 (2H, d), 8.02 (1H, s) |
| 1-287 | 1.74-2.21 (4H, m), 2.57 (6H, s), 3.03-3.65 (4H, m), 4.61-4.75 (3H, m), 7.62-7.80 (5H, m) |
| 1-288 | 1.05 (3H, t), 1.71-2.19 (4H, m), 2.64 (3H, s), 3.32-3.70 (3H, m), 4.13 (2H, q), 4.73-4.81 (1H, m), 7.59-7.70 (4H, m), 8.06 (1H, s) |
| 1-289 | 1.72-2.11 (4H, m), 2.44 (3H, s), 2.62 (3H, s), 2.91 (3H, s), 3.29-3.66 (3H, m), 4.72-4.77 (1H, m), 7.32-7.40 (4H, m), 7.62-7.85 (5H, m) |
| 1-291 | 1.72-2.22 (4H, m), 2.57 (3H, s), 3.05-3.52 (4H, m), 4.53-4.74 (1H, m), 7.49-8.13 (5H, m) |
| 1-292 | 1.77-2.23 (4H, m), 2.57 (3H, s), 2.65 (3H, s), 3.06-3.60 (4H, m), 4.60-4.72 (1H, m), 7.44-7.90 (5H, m) |
| 1-294 | 1.80-2.40 (7H, m), 3.03-3.53 (4H, m), 4.72-4.81 (1H, m), 7.45-8.10 (5H, m), 8.51 (2H, s) |
| 1-295 | 1.73-2.19 (4H, m), 2.56-2.79 (9H, m), 3.05-3.62 (4H, m), 4.59-4.73 (1H, m), 7.69-7.81 (5H, m) |
| 1-296 | 1.70-2.19 (4H, m), 2.40-3.64 (16H, m), 4.59-4.79 (1H, m), 7.66-7.85 (5H, m) |
| 1-297 | 1.78-2.23 (4H, m), 2.57 (3H, s), 2.72 (3H, s), 3.06-3.58 (4H, m), 4.64-4.72 (1H, m), 7.70-7.80 (4H, m), 8.12 (1H, s), 10.00 (1H, s) |
| 1-298 | 1.78-2.22 (4H, m), 2.57-2.61 (6H, m), 3.06-3.68 (4H, m), 3.96 (3H, s), 4.67-4.75 (1H, m), 7.61-7.74 (4H, m), 7.97 (1H, s), 8.10 (1H, s) |
| 1-299 | 1.74-2.21 (4H, m), 2.57-2.60 (6H, m), 3.06-3.63 (5H, m), 3.61-3.72 (1H, m), 7.71-8.05 (5H, m) |
| 1-300 | 1.75-2.23 (4H, m), 2.56-2.62 (6H, m), 3.04-3.68 (4H, m), 4.65-4.74 (1H, m), 5.32-5.74 (2H, m), 6.61-6.64 (1H, m), 7.45-8.19 (5H, m) |
| 1-305 | 1.75-2.23 (4H, m), 2.57 (3H, s), 3.03-3.61 (4H, m), 4.50-4.65 (1H, m), 6.80 (1H, t), 7.50-8.10 (5H, m) |
| 1-307 | 1.71-2.19 (4H, m), 2.70 (3H, s), 3.33-3.65 (3H, m), 4.75-4.82 (1H, m), 7.34-7.42 (4H, m), 7.71 (2H, d), 7.79 (2H, d), 8.16 (1H, s), 10.00 (1H, s) |
| 1-311 | 1.81-2.22 (4H, m), 2.58 (3H, s), 3.07-3.58 (4H, m), 4.52-4.69 (1H, m), 6.81 (1H, t), 7.52-7.78 (3H, m), 8.08 (1H, s) |

TABLE 5-continued

| Compound No. | $^1$H-NMR (CDCl$_3$, δ ppm) |
|---|---|
| 1-312 | 1.79-2.25 (4H, m), 2.58 (3H, s), 3.07-3.58 (4H, m), 3.52-3.68 (1H, m), 6.80 (1H, t), 7.59-7.83 (3H, m), 8.08 (1H, s) |
| 1-313 | 1.79-2.23 (4H, m), 2.58 (3H, s), 3.06-3.56 (4H, m), 4.54-4.65 (1H, m), 6.82 (1H, t), 7.78-7.93 (3H, m), 8.09 (1H, s) |
| 1-314 | 1.79-2.23 (4H, m), 2.58 (3H, s), 3.05-3.55 (4H, m), 3.95 (s, 3H), 4.54-4.69 (1H, m), 7.24-8.06 (4H, m) |
| 1-315 | 1.61-2.18 (4H, m), 2.94-3.51 (4H, m), 4.69-4.80 (1H, m), 6.04 (1H, s), 7.28 (1H, s), 7.82 (2H, d), 8.11-8.16 (3H, m) |
| 1-316 | 1.60-2.17 (4H, m), 2.87-3.54 (4H, m), 3.85 (3H, s), 4.81-4.96 (1H, m), 6.05 (1H, s), 7.42 (1H, s), 7.83 (2H, d), 8.12-8.18 (3H, m) |
| 1-317 | 1.45 (3H, t), 1.59-2.20 (4H, m), 2.66 (3H, s), 2.95-3.55 (4H, m), 4.11 (2H, q), 4.74-4.80 (1H, m), 6.04 (1H, s), 7.31 (1H, s), 7.78 (2H, d), 7.92 (1H, s), 8.03 (2H, d) |
| 1-318 | 1.46 (3H, t), 1.60-2.16 (4H, m), 2.66 (3H, s), 2.88-3.62 (4H, m), 4.11 (2H, q), 4.89-4.95 (1H, m), 6.03 (1H, s), 7.44 (1H, s), 7.78 (2H, d), 7.92 (1H, s), 8.04 (2H, d) |
| 1-320 | 1.75-2.22 (4H, m), 2.57 (3H, s), 2.65 (3H, s), 3.06-3.58 (4H, m), 4.59-4.72 (1H, m), 7.65 (2H, d), 7.80-7.85 (3H, d) |
| 1-321 | 1.74-2.21 (4H, m), 2.57 (3H, s), 3.05-3.56 (4H, m), 4.52-4.68 (1H, m), 5.94 (1H, t), 6.81 (1H, t), 7.39 (2H, d), 8.03-8.06 (3H, m) |
| 1-322 | 1.77-2.19 (4H, m), 2.57 (3H, s), 3.05-3.59 (4H, m), 4.55-4.65 (1H, m), 6.60 (1H, t), 6.79 (1H, t), 7.25 (2H, d), 8.02-8.05 (3H, m) |
| 1-323 | 1.35 (9H, s), 1.80-2.21 (4H, m), 2.57 (3H, s), 3.03-3.61 (4H, m), 4.57-4.67 (1H, m), 6.79 (1H, t), 7.56 (2H, d), 7.92 (2H, d), 8.02 (1H, s) |
| 1-326 | 0.93 (3H, d), 1.80-2.19 (3H, m), 2.58-3.54 (7H, m), 4.71-4.85 (1H, m), 6.82 (1H, t), 7.81 (2H, d), 8.08-8.13 (3H, m) |
| 1-327 | 0.93 (3H, d), 1.85-2.47 (3H, m), 2.58 (3H, s), 3.22-4.26 (4H, m), 6.82 (1H, t), 7.81 (2H, d), 8.07-8.12 (3H, m) |
| 1-328 | 0.95-2.05 (8H, m), 2.58 (3H, s), 2.72-3.55 (4H, m), 4.72-4.79 (1H, m), 6.86 (1H, t), 7.82 (2H, d), 8.06-8.14 (3H, m) |
| 1-329 | 0.97-2.10 (8H, m), 2.58 (3H, s), 3.21-4.25 (5H, m), 6.84 (1H, t), 7.82 (2H, d), 8.06-8.14 (3H, m) |
| 1-330 | 1.80-2.24 (4H, m), 2.57 (3H, s), 3.06-3.61 (4H, m), 4.55-4.66 (1H, m), 6.83 (1H, t), 7.94-8.24 (7H, m), 8.98 (1H, s) |
| 1-331 | 1.82-2.20 (4H, m), 2.57 (3H, s), 3.03-3.59 (4H, s), 4.60-4.65 (1H, m), 7.77 (2H, d), 7.94 (1H, s), 8.08 (2H, d) |
| 1-332 | 1.79-2.21 (4H, m), 2.29 (3H, s), 2.96-3.60 (4H, m), 4.10 (3H, s), 4.77-4.81 (1H, m), 7.77 (2H, d), 7.94 (s, 1H), 8.08 (2H, d), 8.51 (2H, s) |
| 1-333 | 1.77-2.22 (4H, m), 2.57 (3H, s), 3.05-3.62 (4H, m), 4.57-4.66 (1H, m), 7.79-8.10 (5H, m) |
| 1-334 | 1.85-2.65 (10H, m), 3.22-3.68 (3H, m), 4.72-4.77 (1H, m), 7.32-8.30 (10H, m) |
| 1-335 | 1.98-2.70 (10H, m), 3.21-3.72 (3H, m), 4.72-4.82 (1H, m), 7.34-8.30 (10H, m) |
| 1-336 | 1.87-2.22 (4H, m), 2.50 (3H, s), 3.04-3.59 (4H, m), 4.77-4.84 (1H, m), 7.02 (1H, s), 7.81 (2H, d), 8.01-8.12 (3H, m), 8.52 (1H, s) |
| 1-337 | 1.88-2.23 (4H, m), 2.57 (3H, s), 2.64 (3H, s), 3.07-3.61 (4H, m), 4.58-4.67 (1H, m), 7.74 (1H, s), 7.78 (2H, d), 8.08 (2H, d) |
| 1-338 | 1.76-2.20 (4H, m), 2.57 (3H, s), 3.03-3.59 (4H, m), 4.39-4.60 (3H, m), 6.79 (1H, t), 7.10 (2H, d), 8.00-8.05 (3H, m) |
| 1-339 | 1.79-2.21 (4H, m), 2.57 (3H, s), 3.05-3.56 (4H, m), 4.46-4.65 (3H, m), 6.79 (1H, t), 7.09 (2H, d), 8.01-8.04 (3H, m) |
| 1-340 | 1.75-2.39 (8H, m), 2.56 (3H, s), 3.03-3.58 (4H, m), 4.09-4.12 (2H, m), 4.55-4.64 (1H, m), 6.78 (1H, t), 7.02 (2H, d), 7.99-8.02 (3H, m) |
| 1-343 | 1.78-2.23 (4H, m), 2.58 (3H, s), 3.09-3.52 (4H, m), 4.54-4.66 (1H, m), 7.95 (2H, d), 8.11-8.17 (3H, m) |
| 1-344 | 1.80-2.21 (4H, m), 2.57 (3H, s), 3.06-3.58 (4H, m) 4.55-4.64 (1H, m), 6.80 (1H, t), 7.08-7.42 (7H, m), 7.98-8.02 (3H, m) |
| 1-345 | 1.78-2.21 (4H, m), 2.57 (3H, s), 2.61-2.73 (2H, m), 3.04-3.56 (4H, m), 4.26-4.59 (3H, m), 6.80 (1H, t), 7.04 (2H, d), 7.99-8.03 (3H, m) |
| 1-350 | 1.75-2.22 (4H, m), 2.58 (3H, s), 3.05-3.55 (4H, m), 4.01 (3H, s), 4.55-4.66 (1H, m), 7.77 (2H, d), 8.05 (2H, d), 8.11 (1H, s) |
| 1-351 | 1.80-2.22 (4H, m), 2.58 (3H, s), 3.06-3.54 (4H, m), 4.52-4.68 (1H, m), 7.94-8.23 (4H, m) |
| 1-352 | 1.75-2.22 (4H, m), 2.43 (3H, s), 3.32-3.81 (3H, m), 4.68-4.75 (1H, m), 7.33-7.43 (4H, m), 7.68-7.77 (4H, m), 8.47 (1H, s) |
| 1-353 | 1.75-2.20 (4H, m), 2.43 (3H, s), 3.33-3.80 (3H, m), 4.64-4.80 (1H, m), 7.33-7.43 (4H, m), 7.78 (4H, m), 8.54 (1H, s) |
| 1-354 | 1.79-2.22 (4H, m), 2.71 (3H, s), 3.36-3.80 (3H, m), 3.68-3.74 (1H, m), 7.34-7.44 (4H, m), 7.79 (4H, m), 8.63 (1H, s) |
| 1-355 | 1.38 (d, 6H), 1.79-2.22 (4H, m), 2.59 (3H, s), 3.05-3.54 (4H, m), 4.62-4.68 (2H, m), 7.02 (2H, d), 8.02-8.12 (3H, m) |
| 1-356 | 1.78-2.23 (4H, m), 2.58 (3H, s), 3.05-3.54 (4H, m), 4.55-4.98 (2H, m), 7.22-7.26 (2H, m), 8.03-8.09 (3H, m) |
| 1-358 | 1.85-2.32 (4H, m), 2.78 (3H, s), 3.14-3.60 (4H, m), 4.60-4.72 (1H, m), 6.83 (1H, t), 7.82 (2H, d), 8.09-8.12 (3H, m) |

TABLE 5-continued

| Compound No. | $^1$H-NMR (CDCl$_3$, δ ppm) |
|---|---|
| 2-16 | 1.81-2.21 (4H, m), 2.40 (3H, s), 2.97 (3H, s), 3.16-3.59 (3H, m), 4.62-4.69 (1H, m), 7.06-7.82 (9H, m) |
| 2-17 | 1.65-2.25 (4H, m), 2.97 (3H, s), 3.15-3.71 (3H, m), 4.54-4.63 (1H, m), 7.05-8.13 (10H, m) |
| 2-18 | 1.82-2.19 (4H, m), 2.28 (3H, s), 2.98-3.98 (4H, m), 4.63-4.80 (1H, m), 7.24-8.50 (8H, m) |
| 2-19 | 1.65-2.22 (4H, m), 2.97 (3H, s), 3.13-3.75 (3H, m), 4.54-4.62 (1H, m), 7.03-8.08 (10H, m) |
| 2-20 | 1.68-2.23 (4H, m), 2.97 (3H, s), 3.14-3.76 (3H, m), 4.51-4.65 (1H, m), 7.05-8.08 (10H, m) |
| 3-13 | 1.65-1.98 (4H, m), 2.56 (3H, s), 2.69-3.55 (6H, m), 4.61-4.67 (1H, m), 6.85 (1H, t), 7.82 (2H, d), 8.05-8.13 (3H, m) |
| 3-14 | 1.61-2.04 (4H, m), 2.53-3.72 (9H, m), 4.34-4.40 (1H, m), 6.88 (1H, t), 7.81 (2H, d), 8.02 (1H, s), 8.11 (2H, d) |
| 3-15 | 1.65-1.95 (4H, m), 2.56-3.45 (12H, m), 4.69-4.74 (1H, m), 7.79 (2H, d), 7.94 (1H, s), 8.05 (2H, d) |
| 3-16 | 1.55-2.04 (4H, m), 2.52-3.72 (12H, m), 4.41-4.44 (1H, m), 7.78 (2H, d), 8.02-8.08 (3H, m) |
| 3-19 | 1.85-2.22 (6H, m), 2.58 (3H, s), 3.39-3.48 (1H, m), 3.88-3.91 (1H, m), 4.98-5.02 (1H, m), 6.87 (1H, t), 7.82 (2H, d), 8.11 (2H, d), 8.17 (1H, s) |
| 3-20 | 1.75-2.21 (4H, m), 2.57 (3H, s), 3.03-3.58 (1H, m), 4.53-4.61 (1H, m), 6.80 (1H, t), 7.23 (1H, d), 7.73 (1H, s), 7.82 (1H, d), 8.04 (1H, s) |
| 3-22 | 1.77-2.22 (4H, m), 2.57 (3H, s), 2.65 (3H, s), 3.08-3.59 (4H, m), 4.61-4.72 (1H, m), 7.19 (1H, d), 7.23 (1H, d), 7.66 (1H, s), 7.86 (1H, s) |
| 3-23 | 1.73-2.21 (4H, m), 2.57 (3H, s), 3.03-3.53 (4H, m), 4.53-4.65 (1H, m), 7.75-8.11 (4H, m) |
| 3-24 | 2.02-2.32 (3H, m), 3.60-4.44 (4H, m), 4.81-5.32 (2H, m), 6.84 (1H, t), 7.08-7.33 (4H, m), 7.82 (2H, d), 8.11 (2H, d), 8.20 (1H, s) |
| 3-25 | 1.80-2.22 (4H, m), 2.58 (3H, s), 3.08-3.62 (4H, m), 4.56-4.70 (1H, m), 6.86 (1H, t), 7.55-8.08 (7H, m), 8.53 (1H, s) |
| 4-5 | 4.22-4.52 (4H, m), 5.71 (1H, s), 6.99 (1H, t), 7.05-7.09 (2H, m), 7.44-7.47 (2H, m), 7.96 (2H, d), 8.09 (2H, d), 8.24 (1H, s) |
| 4-9 | 2.75 (3H, s), 3.07 (3H, s), 4.08-4.52 (4H, m), 7.29-7.43 (4H, m), 7.78 (2H, d), 7.97 (1H, s), 8.04 (2H, d) |
| 5-1 | 1.71-2.18 (4H, m), 3.21-3.72 (3H, m), 4.58-4.69 (1H, m), 7.06-8.49 (11H, m) |
| 5-2 | 1.72-2.17 (4H, m), 3.22-3.73 (3H, m), 4.55-4.67 (1H, m), 7.31-8.25 (10H, m) |

[Biological Test]

The following test examples show that the compounds of the present invention are useful as an active ingredient of an insecticide, an acaricide or an ectoparasite controlling agent.

(Preparation of Test Emulsion)

5 parts by weight of the compound of the present invention, 93.6 parts by weight of dimethylformamide, and 1.4 parts by weight of polyoxyethylene alkylaryl ether were mixed and dissolved to prepare an emulsion (I) containing 5% of an active ingredient.

(Test Example 1) Efficacy Test Against *Mythimna Separate*

0.8 g of a commercially available artificial diet (Insecta LFS, manufactured by Nosan Corporation) and 1 µl of the emulsion (I) were thoroughly mixed and 0.2 g per each treatment group was packed in a plastic test container (1.4 ml volume) to prepare a test diet.

Two second instar larvae of *Mythimna separata* were inoculated for each treatment group and sealed with a plastic lid. It was placed in a thermostatic chamber at 25° C., and the insecticidal rate and food intake were examined on the fifth day. The test was repeated twice.

The compounds in Table 6 were tested for efficacy against *Mythimna separata*. All of the compounds were effective against *Mythimna separata*, with the insecticidal rate being 100% or the food intake being 10% or less, relative to the solvent control group.

TABLE 6

| Compound No. | | | | | | | |
|---|---|---|---|---|---|---|---|
| 1-1 | 1-21 | 1-43 | 1-65 | 1-103 | 1-126 | 1-151 | 2-8 |
| 1-3 | 1-22 | 1-44 | 1-68 | 1-104 | 1-127 | 1-152 | 2-11 |
| 1-4 | 1-23 | 1-45 | 1-72 | 1-105 | 1-128 | 1-153 | 2-12 |
| 1-5 | 1-24 | 1-46 | 1-73 | 1-106 | 1-129 | 1-154 | 3-1 |
| 1-6 | 1-26 | 1-47 | 1-79 | 1-107 | 1-130 | 1-155 | 3-2 |
| 1-7 | 1-27 | 1-48 | 1-81 | 1-108 | 1-132 | 1-156 | 3-3 |
| 1-8 | 1-28 | 1-52 | 1-84 | 1-109 | 1-133 | 1-157 | 3-9 |
| 1-9 | 1-29 | 1-55 | 1-87 | 1-111 | 1-136 | 1-158 | 3-11 |
| 1-11 | 1-30 | 1-56 | 1-90 | 1-114 | 1-137 | 1-160 | 4-1 |
| 1-12 | 1-31 | 1-57 | 1-91 | 1-116 | 1-138 | 1-163 | 4-2 |
| 1-13 | 1-32 | 1-58 | 1-92 | 1-117 | 1-140 | 1-166 | |
| 1-14 | 1-33 | 1-59 | 1-94 | 1-118 | 1-145 | 1-167 | |
| 1-15 | 1-35 | 1-60 | 1-95 | 1-119 | 1-146 | 1-168 | |
| 1-16 | 1-36 | 1-61 | 1-96 | 1-120 | 1-147 | 2-1 | |
| 1-17 | 1-39 | 1-62 | 1-97 | 1-121 | 1-148 | 2-3 | |
| 1-18 | 1-40 | 1-63 | 1-98 | 1-122 | 1-149 | 2-6 | |
| 1-19 | 1-41 | 1-64 | 1-99 | 1-124 | 1-150 | 2-7 | |

| Compound No. | | | | | | |
|---|---|---|---|---|---|---|
| 1-172 | 1-192 | 1-215 | 1-233 | 1-280 | 1-334 | 3-19 |
| 1-174 | 1-196 | 1-216 | 1-238 | 1-290 | 1-339 | 3-24 |
| 1-178 | 1-198 | 1-218 | 1-249 | 1-299 | 1-342 | 4-5 |
| 1-183 | 1-199 | 1-221 | 1-251 | 1-302 | 1-343 | 4-6 |
| 1-184 | 1-201 | 1-222 | 1-255 | 1-313 | 1-347 | 4-9 |
| 1-186 | 1-203 | 1-224 | 1-257 | 1-314 | 2-20 | 4-11 |
| 1-188 | 1-209 | 1-225 | 1-258 | 1-324 | 3-12 | 4-13 |
| 1-189 | 1-210 | 1-227 | 1-259 | 1-326 | 3-13 | |
| 1-190 | 1-211 | 1-230 | 1-273 | 1-330 | 3-15 | |
| 1-191 | 1-214 | 1-232 | 1-279 | 1-331 | 3-16 | |

(Test Example 2) Efficacy Test Against *Spodoptera litura*

The emulsion (I) was diluted with water so that the concentration of the compound of the present invention was 125 ppm. A cabbage leaf was immersed in the diluent for 30 seconds. This cabbage leaf was placed in a petri dish, and five second instar larvae of *Spodoptera litura* were released. The petri dish was placed in a thermostatic chamber with a temperature of 25° C. and a humidity of 60%. Viability was evaluated when 6 days passed since the release of the insects, and the insecticidal rate was calculated. The test was repeated twice.

The compounds in Table 7 were tested for efficacy against *Spodoptera litura*. All compounds showed an insecticidal rate of 80% or more against *Spodoptera litura*.

TABLE 7

| Compound No. |
| --- |
| 1-1 |
| 1-6 |
| 1-7 |
| 1-9 |
| 1-11 |
| 1-14 |
| 1-15 |
| 1-17 |
| 1-18 |
| 1-20 |
| 1-21 |
| 1-23 |
| 1-24 |
| 1-28 |
| 1-29 |
| 1-30 |
| 1-33 |
| 1-35 |
| 1-44 |
| 1-46 |
| 1-52 |
| 1-55 |
| 1-56 |
| 1-91 |
| 1-92 |
| 1-94 |
| 1-116 |
| 1-126 |
| 1-127 |
| 1-151 |
| 2-1 |
| 2-6 |
| 2-7 |

(Test Example 3) Efficacy Test Against *Tetranychus urticae*

Kidney bean plants were raised in No. 3 pots, and 8 female adults of *Tetranychus urticae* from Aomori prefecture were inoculated on the primary leaves. The emulsion (I) was diluted with water so that the concentration of the compound of the present invention was 125 ppm. The diluent was sprayed on the kidney bean plants. The kidney bean plants were placed in a thermostatic chamber with a temperature of 25° C. and a humidity of 65%. The life and death of mites were investigated when 10 days had passed after spraying. The test was repeated twice.

The compounds in Table 8 were tested for efficacy against *Tetranychus urticae*. All compounds showed an insecticidal rate of 90% or more.

TABLE 8

| Compound No. |
| --- |
| 1-1 |
| 1-2 |
| 1-5 |
| 1-16 |
| 1-17 |
| 1-19 |
| 1-30 |
| 1-31 |
| 1-35 |
| 1-36 |
| 1-37 |
| 1-39 |
| 1-43 |
| 1-45 |
| 1-47 |
| 1-48 |
| 1-53 |
| 1-57 |
| 1-58 |
| 1-60 |
| 1-61 |
| 1-62 |
| 1-63 |
| 1-64 |
| 1-65 |
| 1-67 |
| 1-69 |
| 1-70 |
| 1-72 |
| 1-73 |
| 1-74 |
| 1-76 |
| 1-83 |
| 1-84 |
| 1-85 |
| 1-92 |
| 1-96 |
| 1-97 |
| 1-98 |
| 1-105 |
| 1-106 |
| 1-111 |
| 1-114 |
| 1-115 |
| 1-117 |
| 1-118 |
| 1-122 |
| 1-123 |
| 1-127 |
| 1-129 |
| 1-130 |
| 1-131 |
| 1-132 |
| 1-133 |
| 1-134 |
| 1-137 |
| 1-138 |
| 1-139 |
| 1-140 |
| 1-141 |
| 1-142 |
| 1-143 |
| 1-144 |
| 1-146 |
| 1-147 |
| 1-148 |
| 1-154 |
| 1-156 |
| 1-157 |
| 1-158 |
| 1-159 |
| 1-161 |
| 1-162 |
| 1-163 |
| 1-164 |
| 1-165 |
| 2-6 |
| 1-172 |

TABLE 8-continued

| Compound No. |
|---|
| 1-173 |
| 1-174 |
| 1-175 |
| 1-176 |
| 1-180 |
| 1-182 |
| 1-183 |
| 1-185 |
| 1-186 |
| 1-187 |
| 1-188 |
| 1-189 |
| 1-190 |
| 1-191 |
| 1-192 |
| 1-194 |
| 1-196 |
| 1-197 |
| 1-198 |
| 1-199 |
| 1-200 |
| 1-201 |
| 1-202 |
| 1-204 |
| 1-205 |
| 1-206 |
| 1-207 |
| 1-208 |
| 1-209 |
| 1-210 |
| 1-213 |
| 1-214 |
| 1-215 |
| 1-216 |
| 1-217 |
| 1-221 |
| 1-222 |
| 1-223 |
| 1-224 |
| 1-225 |
| 1-226 |
| 1-227 |
| 1-231 |
| 1-232 |
| 1-233 |
| 1-234 |
| 1-235 |
| 1-237 |
| 1-239 |
| 1-240 |
| 1-241 |
| 1-242 |
| 1-243 |
| 1-245 |
| 1-246 |
| 1-247 |
| 1-249 |
| 1-250 |
| 1-251 |
| 1-252 |
| 1-253 |
| 1-254 |
| 1-255 |
| 1-256 |
| 1-257 |
| 1-258 |
| 1-259 |
| 1-264 |
| 1-267 |
| 1-268 |
| 1-269 |
| 1-271 |
| 1-273 |
| 1-279 |
| 1-280 |
| 1-281 |
| 1-283 |
| 1-284 |
| 1-285 |
| 1-292 |
| 1-293 |
| 1-294 |
| 1-301 |
| 1-302 |
| 1-303 |
| 1-305 |
| 1-311 |
| 1-312 |
| 1-313 |
| 1-314 |
| 1-315 |
| 1-316 |
| 1-317 |
| 1-318 |
| 1-319 |
| 1-320 |
| 1-321 |
| 1-322 |
| 1-324 |
| 1-326 |
| 1-327 |
| 1-328 |
| 1-329 |
| 1-330 |
| 1-331 |
| 1-332 |
| 1-333 |
| 1-337 |
| 1-338 |
| 1-339 |
| 1-340 |
| 1-341 |
| 1-342 |
| 1-343 |
| 1-345 |
| 1-350 |
| 1-356 |
| 1-357 |
| 1-358 |
| 1-359 |
| 1-360 |
| 1-361 |
| 1-362 |
| 2-16 |
| 3-12 |
| 3-13 |
| 3-14 |
| 3-15 |
| 3-16 |
| 3-20 |
| 3-22 |
| 3-23 |
| 3-24 |
| 3-26 |
| 4-6 |
| 4-8 |
| 4-9 |
| 4-11 |
| 4-13 |
| 5-1 |

(Test Example 4) Efficacy Test Against *Tetranychus urticae* Rroot Dipping Treatment)

The emulsion (I) was diluted with water so that the concentration of the compound of the present invention was 31 ppm. The roots of kidney bean seedlings whose roots had been washed in advance were immersed in the diluent. Four days later, 10 female adults of *Tetranychus urticae* were inoculated and placed in a thermostatic chamber with a temperature of 25° C. and a humidity of 60%. After 14 days from inoculation, the number of surviving mites was investigated and the control rate was obtained by the following formula.

Control rate (%)=100−{(Nt)/(Nc)×100}

Nt: Number of surviving mites in the treated group; Nc: Number of surviving mites in the untreated group The compounds in Table 9 were tested for efficacy (root dipping treatment) against *Tetranychus urticae*. All compounds showed a control rate of 90% or more.

TABLE 9

| Compound No. |
| --- |
| 1-70 |
| 1-74 |
| 1-115 |
| 1-161 |
| 1-163 |
| 1-170 |

(Test Example 5) Efficacy Test Against *Tetranychus urticae* (Soil Irrigation Treatment)

The emulsion (I) was diluted with water so that the concentration of the compound of the present invention was 500 ppm. A cell-planted kidney bean seedling was subjected to a plant foot irrigation treatment with 4 ml of the above diluent, and placed in a thermostatic chamber with a temperature of 25° C. and a humidity of 60%. Four days later, the above kidney bean seedling was re-planted in a No. 3 pot, and after inoculating 10 female adults of *Tetranychus urticae*, placed in a thermostatic chamber with a temperature of 25° C. and a humidity of 60%. After 14 days from inoculation, the number of surviving mites was investigated and the control rate was obtained by the following formula.

Control rate (%)=100−{(Nt)/(Nc)×100}

Nt: Number of surviving mites in the treated group; Nc: Number of surviving mites in the untreated group The compounds in Table 10 were tested for efficacy (soil irrigation treatment) against *Tetranychus urticae*. All compounds showed a control rate of 90% or more.

TABLE 10

| Compound No. |
| --- |
| 1-115 |
| 1-161 |
| 1-163 |

Since those randomly selected from among the compounds of the present invention exert the above-mentioned effects, it can be understood that the compounds of the present invention including the compounds that are not exemplified are compounds having the effects of pest control, in particular, insecticidal, acaricidal and ectoparasiticidal effects and the like, which causes no phytotoxicity to plant bodies, with little toxicity to animals and fish and little impact on the environment.

INDUSTRIAL APPLICABILITY

It is possible to provide a cyclic amine compound which is excellent in pest control activity, in particular, insecticidal activity and/or acaricidal activity, excellent in safety and can be synthesized in an industrially favorable manner, and a pest control agent containing this agent as an active ingredient.

The invention claimed is:

1. A compound represented by a formula (II), or a salt thereof:

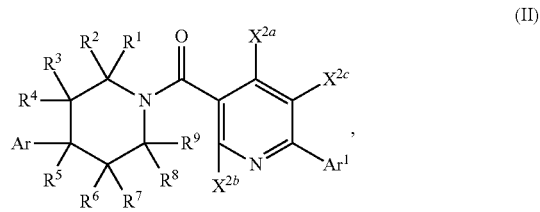

wherein $Ar^1$ is a substituted or unsubstituted $C_{6-10}$ aryl group;

$X^{2a}$ and $X^{2b}$ independently represent a hydrogen atom, a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, an imino (substituted or unsubstituted $C_{1-6}$ alkylthio) methyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a nitro group, a cyano group, or a group represented by a formula: "$R^cO-N=CR^d-$" (wherein $R^c$ is a hydrogen atom, a substituted or unsubstituted $C_{1-6}$ alkyl group, or a substituted or unsubstituted $C_{1-6}$ alkylcarbonyl group, $R^d$ is a hydrogen atom, a substituted or unsubstituted $C_{1-6}$ alkyl group, or an amino group);

$X^{2c}$ represents a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, an imino (substituted or unsubstituted $C_{1-6}$ alkylthio) methyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a nitro group, a cyano group, or a group represented by a formula: "$R^cO-N=CR^d-$" (wherein $R^c$ is a hydrogen atom, a substituted or unsubstituted $C_{1-6}$ alkyl group, or a substituted or unsubstituted $C_{1-6}$ alkylcarbonyl group, $R^d$ is a hydrogen atom, a substituted or unsubstituted $C_{1-6}$ alkyl group, or an amino group);

$R^1$ to $R^4$ and $R^6$ to $R^9$ each independently represent a hydrogen atom, a substituted or unsubstituted $C_{1-6}$ alkyl group, a substituted or unsubstituted $C_{1-6}$ alkoxy group, a substituted or unsubstituted $C_{1-6}$ alkoxycarbonyl group, a hydroxyl group, or a halogeno group; $R^1$ and $R^9$ may form a $C_{2-6}$ alkylene group together, $R^3$ and $R^6$ may form a $C_{2-6}$ alkylene group together, and $R^2$ and $R^3$ may form a $C_{3-6}$ alkylene group together;

$R^5$ represents a hydrogen atom, a substituted or unsubstituted $C_{1-6}$ alkyl group, a substituted or unsubstituted $C_{1-6}$ alkoxy group, a substituted or unsubstituted $C_{1-6}$ alkylcarbonyl group, a substituted or unsubstituted $C_{1-6}$ alkoxycarbonyl group, a substituted or unsubstituted $C_{1-6}$ alkylaminocarbonyl group, a substituted or unsubstituted $C_{1-6}$ alkylcarbonyloxy group, a substituted or unsubstituted $C_{1-6}$ alkoxycarbonyloxy group, a substituted or unsubstituted phenyl group, a hydroxyl group, a halogeno group, or a cyano group; and $R^3$ and $R^5$ may form a $C_{1-6}$ alkylenedioxy group together; and Ar is a substituted or unsubstituted heteroaryl group selected from a group consisting of a pyrazolyl group, an oxazolyl group, an isoxazolyl group, a thiazolyl group, a triazolyl group, an oxadiazolyl group, a thiadiazolyl group, a pyridyl group, a pyrimidinyl group, and a pyridazinyl group, wherein a substituted group on the "heteroaryl group" represented by Ar is selected from a halogeno group, a substituted or unsubstituted $C_{1-6}$ alkyl group, a hydroxyl group, a substituted or unsubstituted $C_{1-6}$ alkoxy group, a substituted or unsubstituted $C_{1-6}$ alkoxycarbonyl group, a substituted or unsubstituted $C_{3-8}$ cycloalkyl group, a substituted or unsubstituted $C_{6-10}$ aryl group, a cyano group and an oxy $C_{1-6}$ haloalkyleneoxy group, wherein a substituted group on the "$C_{1-6}$ alkyl group", "$C_{2-6}$ alkenyl group", "$C_{2-6}$ alkenyloxy group", "$C_{2-6}$ alkynyl group", "$C_{1-6}$ alkoxy group", "$C_{1-6}$ alkylamino group", "$C_{1-6}$ alkylcarbonyl group", "$C_{1-6}$ alkylcarbonylamino group", "$C_{1-6}$ alkoxycarbonyl group", "$C_{1-6}$ alkylaminocarbonyl group", "$C_{1-6}$ alkylaminocarbonyloxy group", "$C_{1-6}$ alkylcarbonyloxy group", "$C_{1-6}$ alkylthio group", "$C_{1-6}$ alkylsulfinyl group", "$C_{1-6}$ alkylsulfonyl group", "$C_{1-6}$ alkoxysulfonyl group", "$C_{1-6}$ alkylaminothiocarbonyl group", "imino ($C_{1-6}$ alkylthio) methyl group" or "$C_{1-6}$ alkylaminosulfonyl group" described above is selected from a halogeno group; a $C_{1-6}$ alkoxy group; a $C_{1-6}$ haloalkoxy group; and a cyano group, wherein a substituted group on the "$C_{3-8}$ cycloalkyl group", "$C_{6-10}$ aryl group", and "$C_{6-10}$ aryloxy group" is selected from a halogeno group; a $C_{1-6}$ alkyl group; a $C_{1-6}$ haloalkyl group; a $C_{1-6}$ alkoxy group; a $C_{1-6}$ haloalkoxy group; and a cyano group.

2. The compound according to claim 1, or a salt thereof, wherein a group that can be substituted on a $C_{6-10}$ aryl group represented by $Ar^1$ is a halogeno group, a substituted or unsubstituted $C_{1-6}$ alkyl group, a substituted or unsubstituted $C_{2-6}$ alkenyl group, a substituted or unsubstituted $C_{2-6}$ alkenyloxy group, a substituted or unsubstituted $C_{2-6}$ alkynyl group, a hydroxyl group, a substituted or unsubstituted $C_{1-6}$ alkoxy group, an amino group, a substituted or unsubstituted $C_{1-6}$ alkylamino group, a formyl group, a substituted or unsubstituted $C_{1-6}$ alkylcarbonyl group, a substituted or unsubstituted $C_{1-6}$ alkylcarbonylamino group, a carboxyl group, a substituted or unsubstituted $C_{1-6}$ alkoxycarbonyl group, a carbamoyl group, a substituted or unsubstituted $C_{1-6}$ alkylaminocarbonyl group, a substituted or unsubstituted $C_{1-6}$ alkylaminocarbonyloxy group, a substituted or unsubstituted $C_{1-6}$ alkylcarbonyloxy group, a mercapto group, a substituted or unsubstituted $C_{1-6}$ alkylthio group, a substituted or unsubstituted $C_{1-6}$ alkylsulfinyl group, a substituted or unsubstituted $C_{1-6}$ alkylsulfonyl group, a substituted or unsubstituted $C_{1-6}$ alkoxysulfonyl group, a thiocarbamoyl group, a substituted or unsubstituted $C_{1-6}$ alkylaminothiocarbonyl group, a substituted or unsubstituted $C_{1-6}$ alkylaminosulfonyl group, a substituted or unsubstituted $C_{3-8}$ cycloalkyl group, a substituted or unsubstituted $C_{6-10}$ aryl group, a substituted or unsubstituted $C_{6-10}$ aryloxy group, a nitro group, a cyano group, a pentafluorosulfanyl group, or a group represented by a formula: "$R^aO-N=CR^b-$" (wherein $R^a$ is a hydrogen atom or a substituted or unsubstituted $C_{1-6}$ alkyl group, and $R^b$ is a hydrogen atom or a substituted or unsubstituted $C_{1-6}$ alkyl group), and wherein a substituted group on each group described above is the same as that defined in the formula (II).

3. The compound according to claim 1 represented by a formula (III), or a salt thereof:

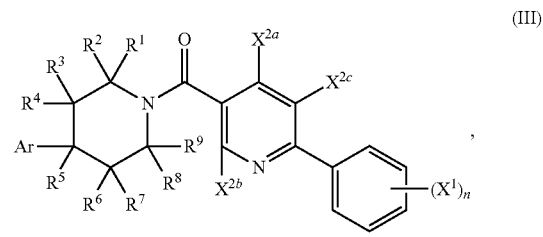

(III)

wherein $R^1$ to $R^4$, $R^6$ to $R^9$, $R^5$ and Ar are the same as those defined in the formula (II);

$X^1$ has the same meaning as that defined in the group that can be substituted on a $C_{6-10}$ aryl group represented by $Ar^1$ of the formula (II);

n represents an integer of 0 to 5; when there are 2 or more $X^1$ groups, $X^1$ groups may be the same as or different from each other; two $X^1$ groups may form a divalent organic group together;

$X^{2a}$, $X^{2b}$, and $X^{2c}$ are the same as those defined in the formula (II), and wherein a substituted group on each group described above is the same as that defined in the formula (II).

4. A composition comprising at least one selected from the group consisting of the compounds according to claim 1 and a salt thereof as an active ingredient, and an inert carrier.

5. A pharmaceutical product for treating a disease or condition to which a sodium channel inhibitor is applied, the pharmaceutical product comprising at least one selected from the group consisting of the compounds according to claim 1 and salts thereof as an active ingredient.

6. The composition of claim 4, wherein the composition has a pest control activity.

7. The composition of claim 4, wherein the composition has an insecticidal or acaricidal activity.

8. The composition of claim 4, wherein the composition has an ectoparasite controlling or eliminator activity.

\* \* \* \* \*